US007989630B2

(12) United States Patent
Pike et al.

(10) Patent No.: US 7,989,630 B2
(45) Date of Patent: Aug. 2, 2011

(54) RADIOTRACERS FOR IMAGING P-GLYCOPROTEIN FUNCTION

(75) Inventors: Victor W. Pike, Bethesda, MD (US); Robert B. Innis, Rockville, MD (US); Sami S. Zoghbi, Great Falls, VA (US); Neva Lazarova, Toronto (CA)

(73) Assignee: National Institutes of Health Represented by the Secretary of the Department of Health and Human Services, National Institutes of Health, Washington, DC (US)

( * ) Notice: Subject to any disclaimer, the term of this patent is extended or adjusted under 35 U.S.C. 154(b) by 378 days.

(21) Appl. No.: 12/112,994

(22) Filed: Apr. 30, 2008

(65) Prior Publication Data

US 2009/0274624 A1 Nov. 5, 2009

(51) Int. Cl.
*C07D 211/52* (2006.01)
*A61K 31/451* (2006.01)

(52) U.S. Cl. ........................................ 546/217; 514/327
(58) Field of Classification Search .................. 546/217; 514/327
See application file for complete search history.

(56) References Cited

FOREIGN PATENT DOCUMENTS

| WO | WO 03/037340 A1 | 5/2002 |
|----|-----------------|--------|
| WO | WO 2004/075926 A1 | 9/2004 |
| WO | WO 2005/080992 A2 | 9/2005 |
| WO | WO 2006/036994 A2 | 4/2006 |

OTHER PUBLICATIONS

Zoghbi, et. al. "[11C]Loperamide and its N-desmethyl radiometabolite are avid substrates for brain Pglycoprotein efflux" Journal of Nuclear Medicine, May 1, 2007, 48 (Supplement 2):248P, Neurosciences: Basic Science Basic Science Posters, abstract 1149.*
Lazarova, et. al. "Synthesis and 11C-labeling of N-Desmethyl-loperamide as a prospectively advantageous PET radiotracer for assessing brain P-gp function." Journal of Nuclear Medicine, May 1, 2007, 48 (Supplement 2):300P, Neurosciences: Basic Science Basic Science Posters, abstract 1329.*
Choo, Edna F. et al.; "Differential in Vivo Sensitivity to Inhibition of P-glycoprotein located in Lymphocytes, Testes, and the Blood-Brain Barrier"; 2006, *The Journal of Pharmacology and Experimental Therapeutics*, vol. 317, No. 3, pp. 1012-1018.
Croucher, Martin J. et al.; "Inhibition of the development of electrical kindling of the prepyriform cortex by daily focal injections of excitatory amino acid antagonists"; 1988, *European Journal of Pharmacology*, vol. 152, pp. 29-38.
Ganbmann, B. et al.; "Simultaneous Determination of Loperamide and its Desmethylated Metabolites in Plasma and Urine by High-Performance Liquid Chromatography—Atmospheric-Pressure Ionization Mass Spectrometry"; 2001, *Chromatographia*, vol. 53, pp. 656-660.
He, Huaibing et al.; "Quantitation of loperamide and N-demethyl-loperamide in human plasma using electrospray ionization with selected reaction ion monitoring liquid chromatography—mass spectrometry"; 2000, *Journal of Chromatography*, vol. 744, pp. 323-331.
Heykants, J.J. P. et al.; "The Excretion and Metabolism of the Antidiarrhoel Loperamide in the Wistar Rat"; 1977, *European Journal of Drug Metabolism and Pharmacokinetics*, No. 2, pp. 81-91.
Johansen, Sys Stybe et al.; "Liquid chromatography—tandem mass spectrometry determination of lopermide and its main metabolite desmethylloperamide in biological specimens and application to forensic cases"; 2004, *Journal of Chromatography*, vol. B811, pp. 31-36.
Kalgutkar, Amit S. et al.; "Identification of an N-methyl-4-Phenylpyridinium-like Metabolite of the Antidiarrheal Agent Loperamide in Human Liver Microsomes: Underlying Reason(s) for the lack of Neurotoxicity Despite the Bioactivation Event"; 2004, *Drug Metabolism and Disposition*, vol. 32. No. 9, pp. 943-952.
Mikus, Gerd et al.; "Reduction of Saquinavir Exposure by Coadministration of Lopermide"; 2004, *Clin. Pharmacokinet*, vol. 43, No. 14, pp. 1015-1024.
Miyazaki, Hisashi et al.; "Disposition and metabolism of h [$^{14}$C]loperamide in rats"; 1979, *European Journal of Metabolism and Pharmacokinetics*, vol. 4, pp. 199-206.
Miyazaki, Hisashi et al.; "Loperamide in Rat Intestines: A Unique Disposition"; 1982, *Life Sciences*, vol. 30, pp. 2203-2206.
Mukwaya, Geoffrey et al.; "Interaction of Ritonavir-Boosted Tipranavir with Loperamide Does Not Result in Loperamide-Associated Neurologic Side Effects in Healthy Volunteers"; 2005, *Antimicrobial Agents and Chemotherapy*, vol. 49, No. 12, pp. 4903-4910.
Niemi, Mikko et al.; "Itraconazole, gemfibrozil and their combination markedly raise the plasma concentrations of loperamide"; 2006, *European Journal of Clinical Pharmacology*, vol. 62, pp. 463-472.
Sadeque, Abu J. M. et al.; "Increased drug delivery to the brain by P-glycoprotein inhibition"; 2000, *Clinical Pharmacology and Therapeutics*, pp. 231-237.
Schinkel, Alfred H. et al.; "P-Glycoprotein in the Blood-Brain Barrier of Mice Influences the Brain Penetration and Pharmacological Activity of Many Drugs"; 1996, *J. Clin. Invest.*, vol. 97, No. 11, 2517-2524.
Sklerov, Jason e tal.; "Tissue Distributin of Loperamide and N-Desmethylloperamide Follow a Fatal Overdose"; 2005, *Journal of Analytical Toxicology*, vol. 29, pp. 750-754.
Tayrouz, Yorki et al.; "Ritonavir increases loperamide plasma concentrations without evidence for P-glycoprotein involvement"; 2001, *Clinical Pharmacology and Therapeutics*, vol. 70, No. 5, pp. 405-414.
Yoshida, Koji et al.; "Metabolites of Loperamide in Rats"; 1979, *Biomedical Mass Spectrometry*, vol. 6, No. 6, pp. 253-259.

(Continued)

*Primary Examiner* — Janet Andres
*Assistant Examiner* — David K O Dell
(74) *Attorney, Agent, or Firm* — Cantor Colburn LLP

(57) ABSTRACT

P-glycoprotein transporter (P-gp) acts as a pump at the blood-brain barrier to exclude a wide range of xenobiotics (e.g., toxins, drugs, etc.) from the brain and is also expressed in a tumor in response to exposure to established or prospective chemotherapeutics (a phenomenon known as multidrug resistance). This invention concerns the preparation and use of radiotracers for imaging P-gp function in vitro and in vivo. Radiotracers of the present invention are avid substrates for P-gp and have structures based on N-Desmethyl-loperamide.

2 Claims, 13 Drawing Sheets

OTHER PUBLICATIONS

Weiss, Johanna; Evaluation of Inhibitory Potencies for Compounds Inhibiting P-Glycoprotein but without maximum effects: $F_2$ values 2006, *Drug Metabolism and Disposition*, vol. 34, No. 2, pp. 203-207.

Zoghbi, Sami S. et al., $^{11}$C-Loperamide and its *N-Desmethyl* Radiometabolite Are Avid Substrates for Brain Permeability—Glycoprotein Efflux; 2008, *Journal of Nuclear Medicine*, pp. 649-656.

Klasner, B.D. et al., "Small animal 18F-FDG PET in vivo imaging of the penumbra in mice.", Neurosciences, p. 248P, abstract 1148, 1 page, 2007.

Lazarova, N. et al., "Synthesis and 11C-labeling of N-Desmethyl-loperamide as a prospectively advantageous PET radiotracer for assessing brain P-gp function.", Neurosciences, p. 300P, abstract 1329. 1 page, 2007.

Liow, J.S. et al., "P-glycoprotein Function Imaged with [11C]N-Desmethyl-Loperamide in Monkey", NIMH, 1 page, first published online in 2008.

Seneca, N., "Inhibition of Metabolism of [11C]Loperamide in Mouse by the Potent CYP3A4 Inhibitor, Ketoconazole", NeuroImage 2008, vol. 412, Supplement 2 (T100), 1 page.

Zoghbi, S.S., "[11C]N-Desmethyl-Loperamide is an Improved Radiotracer with Potential for Measuring Brain P-gp Function", NeuroImage 2008, vol. 412, Supplement 2 (T106), 1 page.

\* cited by examiner

RADIOTRACERS FOR IMAGING P-GLYCOPROTEIN FUNCTION

STATEMENT AS TO RIGHTS TO INVENTIONS MADE UNDER FEDERALLY SPONSORED RESEARCH OR DEVELOPMENT

This invention was made with government support under project # Z01-MH-002795-04 funded by the Intramural Research Program of the National Institutes of Health (National Institute of Mental Health). The government has certain rights in this invention.

FIELD OF THE INVENTION

The present invention relates generally to radiotracers and radiolabeled compounds that are substrates for P-glycoprotein (P-gp). Compounds of the present invention are useful for labeling and diagnostic imaging of P-gp functionality for clinical research, diagnostics and for drug discovery and development. The radiotracers of the present invention are secondary amides and resist metabolism that might generate other undesirable radioactive P-gp substrates, inhibitors or brain-penetrant radiometabolites. Radiotracers of the present invention permit precise accurate quantification of P-gp function in vitro and in vivo.

BACKGROUND OF THE INVENTION

The human multidrug resistance protein family is composed of a number of well characterized members (See, e.g., Borst et al., 2000, *J Natl Cancer Inst* 92:1295-1302). Originally implicated in the resistance of tumor cells to chemotherapeutic agents, the multidrug resistance protein P-glycoprotein (P-gp), an ATP-driven transmembrane efflux pump and a product of the multiple drug resistance 1 (MDR1) gene, belongs to the ATP-binding cassette (ABC) family of proteins. P-gp is an ATP-dependent drug transporter that is predominantly found in the apical membranes of a number of epithelial cell types in the body, including the luminal membrane of the brain capillary endothelial cells that make up the blood-brain barrier. While humans have only one drug-transporting P-gp (MDR1), mice have two, mdr1a (also called mdr3) and mdr1b (also called mdr1) (Gros et al., 1986, *Cell* 47:371-380; Hsu et al., 1989, *J Biol Chem* 264:12053-12062; Devault et al., 1990, *Mol Cell Biol* 10:1652-1663). The tissue distributions of these proteins suggest that the mouse isoforms together perform the same function(s) as the single human MDR1 protein. P-gp is expressed in the human intestine, blood-brain barrier, liver, kidneys, testes and other tissues (Matheny et al., 2001, *Pharmacology* 21(7):778-796; Nolnar et al., 1997, *Anticancer Res* 17(1A):481-486; Bradbury, 1993, *Exp Physiol* 78:453-472; Sugawara, 1990, *Acta Pathol Jpn* 40:545-553; Cordon-Cardo et al., 1990, *J Histochem Cytochem* 9:1277-1287).

Expression of P-gp, localized to cell membranes may affect the bioavailability and biodistribution of drug molecules that are substrates for this transporter. Drugs that inhibit P-gp can alter the absorption, metabolism, disposition, and elimination of co-administered drugs and can enhance bioavailability or cause unwanted drug-drug interactions.

Over the last decade, a large number of structurally diverse compounds has been shown to be transported out of cells by P-gp, leading to a much lower availability of these compounds in their intended tissues than would be expected from the physical properties of the compounds (Schinkel et al., 1996, *J Clin Invest* 97:2517-2524) which only share the properties of being small (usually <2 kDa) hydrophobic amphipathic molecules that are usually not negatively charged.

Classes of small molecule therapeutics that are substrates of P-gp include anticancer, immunosuppressive, cardiac, anti-histamine and a number of anti-infective types including compounds effective against human immunodeficiency virus (HIV). The activity of P-gp also decreases the intracellular availability of a variety of anticancer drugs, leading to the development of resistance to them. The same appears to be true for HIV protease and non-nucleoside reverse transcriptase inhibitors (Fellay et. al., 2002, *Lancet* 359:30-36). For example, P-gp limits the intestinal absorption of digoxin, talinolol and cyclosporine after oral dosing, limits the central nervous system penetration of human immunodeficiency virus protease inhibitors, and excretes paclitaxel (taxol) into the intestine (Lown et al., 1997, *Clin Pharmacol Ther* 62:248-260; Sparreboom et al., 1997, *Proc Natl Acad Sci USA* 94:2031-2035; Kim et al., 1998, *J Clin Invest* 101:289-294; Schwarz et al., 2000, *Int J Clin Pharmacol Ther* 38:61-167). Apical expression of P-gp in tissues such as liver, kidney and intestine results in reduced drug absorption from the gastrointestinal tract and enhanced drug elimination into bile and urine. Moreover, expression of this glycoprotein in the endothelial cells of the blood-brain barrier prevents entry of certain drugs into the central nervous system.

The major documented cause of the multidrug resistance of cancers is the overexpression of P-gp, which is capable of pumping structurally diverse anti-tumor drugs from cells (Houseman et al., *A Molecular Genetic Approach to the Problem of Drug Resistance in Chemotherapy,* 504-517 (1987) (Academic Press, Inc.); Fine and Chabner, *Multidrug Resistance,* in *Cancer Chemotherapy* 8,117-128 (Pinedo and Chabner eds. 1986)). Increased expression of the gene encoding P-gp is found in many malignant cells, including leukemia, lymphoma, sarcoma and carcinoma (Cordon-Cardo et al., 1990, *J Histochem Cytochem* 9:1277-1287). Active P-gp is believed to function as a "hydrophobic vacuum cleaner" which expels hydrophobic drugs from targeted cells. Such drugs include many anti-cancer drugs and cytotoxic agents, such as vinca alkaloids, anthracyclines, epipodophyllotoxins, taxanes, actinomycins, colchicine, puromycin, toxic peptides (e.g., valinomycin), topotecan, and ethidium bromide (See, Pastan and Gottesman, 1987, *New England J Med* 316(22): 1388-1393). Thus, tumor cells expressing elevated levels of the multiple drug transporter accumulate far less anti-tumor agents intracellularly than tumor cells having low levels of this transporter. The degree of resistance of certain tumor cells has been documented to correlate with both elevated expression of the drug transporter and reduced accumulation of the anti-tumor drugs (Gottesman and Pastan, 1988, *J Biol Chem* 263,12163; Fojo et al., 1985, *Cancer Res* 45:3002).

Noninvasive, nuclear imaging techniques can be used to obtain basic and diagnostic information about the physiology and biochemistry of living subjects in general, including experimental animals, normal humans and patients, and for P-gp function in particular, including experimental animals, normal humans and patients. These techniques, including PET (positron emission tomography) and SPECT (single photon emission computed tomography) rely on the use of imaging instruments that can detect radiation emitted from radiotracers administered to living subjects. The information obtained can be reconstructed to provide planar and tomographic images that reveal the distribution and/or concentration of the radiotracer as a function of time.

PET is a noninvasive imaging technique that offers the highest spatial and temporal resolution of all nuclear medicine imaging modalities and has the added advantage that it can allow for true quantitation of tracer concentrations in tissues. The technique involves the use of radiotracers, labeled with positron-emitting radionuclides, that are designed to have in vivo properties that permit measurement of parameters regarding the physiology or biochemistry of a variety of processes in living tissue. SPECT is a nuclear medicine tomographic imaging technique using gamma rays arising from administered radiotracers. It is very similar to conventional nuclear medicine planar imaging using a gamma camera. However, SPECT is able to provide true 3D information.

Radiotracers can be labeled with positron- or gamma-emitting radionuclides. The most commonly used positron-emitting radionuclides are $^{15}O$, $^{13}N$, $^{11}C$ and $^{18}F$, which are usually accelerator-produced and have a half life of 2, 10, 20 and 110 minutes, respectively. The most widely used gamma-emitting radionuclides are $^{18}F$, $^{99m}Tc$, $^{201}Tl$ and $^{123}I$.

Several radiotracers have been developed for PET that are ligands for specific neuroreceptor subtypes such as [$^{11}C$]raclopride and [$^{18}F$]fallypride for dopamine $D_2/D_3$ receptors, [$^{11}C$]WAY-100635 for serotonin 5-HT$_{1A}$ receptors, [$^{11}C$]McN 5652 and [$^{11}C$]DASB for serotonin transporters, [$^{18}F$]altanserin and [$^3H$]ketanserin for serotonin 5-HT$_{2A}$ receptors, or enzyme substrates (e.g., 6-FDOPA for the enzyme, aromatic amino acid decarboxylase) (e.g., Ehrin et al., 1985, *Int J Appl Radiat Isot* 36(4):269-73; Mukherjee et al., 1997, *Synapse* 27(1):1-13; Suehiro et al., 1993, *Life Sci* 53(11):883-92; Houle et al., 2000, *Eur J Nucl Med.* 27(11):1719-22; Meyer et al., 2004, *Am J Psychiatry* 161(5):826-35; Simon et al., 2007, *NeuroImage* 34:1317-1330; Lemaire et al., 1991, *J Nucl Med* 32(12):2266-72; Biver et al., 1997, *Nucl Med Biol* 24(4):357-60; Pike et al., 1995, *Eur J Pharmacol* 283(1-3):R1-3; Gunther et al., 1995, *Nucl Med Biol* 22(7):921-7). These agents permit the visualization of neuroreceptor or enzyme pools in the context of a plurality of neuropsychiatric and neurologic illnesses.

A number of PET and SPECT radiotracers have been developed to demonstrate the presence of P-gp in tissue, but none of these are applied to drug development or currently used as routine clinical diagnostic tool (Del Vecchio et al., 2000, *Cancer Biother Radiopharm* 15:327-337; Hendrikse and Vaalburg, 2002, *Methods* 27:228-233; Levchenko et al., 2000, *J Nucl Med* 41:493-501). Although these imaging tools have their utility, their sensitivity and therefore their scope for research purposes is limited. At most, a 2-3 fold increase of uptake in the P-gp expressing tissue (brain/tumor) is observed at an assumed 100% inhibition dose. This means that if small changes (e.g., <20%) in P-gp functionality suffice for co-treatment in, for example, tumor therapy, current imaging tools may not be sensitive enough to establish the change in P-gp functionality with sufficient confidence and may therefore not be suitable for establishing the required dose of a P-gp inhibitor or competitive substrate.

The most widely examined radiotracers for P-gp imaging include [$^{11}C$]colchicine (Levchenko et al., 2000, *J Nucl Med* 41:493-501), [$^{11}C$]verapamil (Elsinga et al., 1996, *J Nucl Med* 37:1571-1575; Takano et al., 2006, *J Nucl Med* 47:1427-1433), [$^{11}C$]daunorubicin (Elsinga et al., 1996, *J Nucl Med* 37:1571-1575; Takano et al., 2006, *J Nucl Med* 47:1427-1433), [$^{18}F$]paclitaxel (Kurdziel et al., 2003, *J Nucl Med* 44:1330-1339), [$^{94m}Tc$]sestamibi (Bigott et al., 2005, *Mol Imaging* 4:30-39), and [$^{11}C$]loperamide (Passchier et al., 2003, *Mol Imaging Biol* 5:121 (abstract); Wilson et al., 2005, *J Labelled Compd Radiopharm* 48:S142 (abstract)) for PET, and [$^{99m}Tc$]sestamibi (Piwnica-Worms et al., 1993, *Cancer Res* 53:977-984) for SPECT (Del Vecchio et al., 1997, *Eur J Nucl Med* 24:150-159). All of these radiotracers suffer from one or more limitations, such as (i) difficult radiosynthesis (e.g., [$^{94m}Tc$]sestamibi), (ii) troublesome metabolism resulting in significant contamination by radiometabolites (e.g., [$^{11}C$]verapamil), or (iii) low sensitivity, i.e., a low signal to noise ratio because of modest increase of brain uptake after P-gp inhibition. These limitations have so far compromised their use for sensitive and quantitative assessment of P-gp function in vivo, especially in human subjects.

Loperamide, 4-(p-chlorophenyl)-4-hydroxy-N,N-dimethyl-α,α-diphenyl-1-piperidinebutyramide hydrochloride, a synthetic piperidine derivative, is a drug effective against diarrhea resulting from gastroenteritis or inflammatory bowel disease. In most countries loperamide is available generically and under brand names such as Lopex™, Imodium™, Dimor™ and Pepto Diarrhea Control™. Loperamide is an opioid receptor agonist and acts on the µ-opioid receptors in the myenteric plexus large intestines (Awouters et al., 1993, *Digestive Diseases and Sciences* 38:977-995). Loperamide does not cross the blood-brain barrier in significant amounts. Any loperamide molecules that do cross the blood-brain barrier are quickly exported from the brain by the P-gp (Sadeque et al., 2000, *Clin Pharmacol Therapeutics* 68:231-237).

Loperamide (free base) has the following formula (XV):

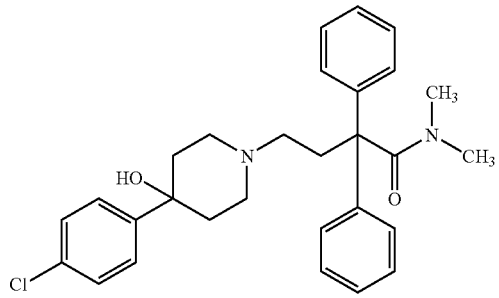

Pharmacokinetic studies have been performed in rats and human using [$^3H$]loperamide labeled at the metabolically unstable methyl groups of the tertiary amide, and in rats using [$^3H$]loperamide labeled at the position adjacent to the chlorine substitution (Heykants et al., 1974, *Arzneim.-Forsch* 24:1649; Heykants et al., 1977, *Eur J Drug Metab Pharmacokinet* 2:81-91). Metabolites of loperamide, such as, desmethyl-loperamide (dLop) and didesmethyl-loperamide have been described (Yoshida et al., 1979, *Biomedical Mass Spectrometry* Vol 6, No. 6. 253-259; Heykants et al., 1977, *European Journal of Drug Metabolism and Pharmacokinetics* 2:81-91; Miyazaki et al., 1982, *Life Sciences* 30:2203-2206). Oxidative N-dealkylation, including demethylation, seemed to be the major metabolic pathway.

As described herein, Applicants have performed PET studies in non-human primates using $^{11}C$-labeled loperamide having the formula (XVI):

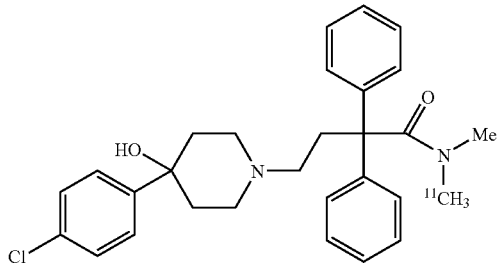

In these studies it was found that [$^{11}$C]loperamide was heavily metabolized and resulted in several undesirable radiometabolites which precluded any possibility of quantitative analysis of P-gp function with [$^{11}$C]loperamide and PET.

Modification of P-gp function is an important underlying mechanism of drug interactions in humans; both inhibition and induction of the protein having been reported as the cause of drug-drug interactions. Compounds which act as P-gp substrates potentially have an increased risk of pharmacokinetic problems in man. There is therefore considerable interest in the pharmaceutical field in determining, at an early stage, whether new drug candidates are potential P-gp substrates as this may significantly reduce their biological efficacy. Due to its importance in pharmacokinetics, P-gp transport screening has now become an integral part of the drug discovery process. However, existing technology for quantifying P-gp transport is generally low through-put, labor-intensive and expensive, characteristics which are far from optimal for meeting the demands of high-throughput screening of the pharmaceutical industry.

The P-gp transport system is complex and poorly understood in man in vivo. Highly sensitive radiotracers which could be used in vivo would be especially beneficial in elucidating P-gp's role in drug and toxin resistance, immunity, apoptosis or cell differentiation. The present invention provides effective new radiotracers and methods for imaging P-gp function. One of the radiotracers of the present invention, [$^{11}$C]N-desmethyl-loperamide, a metabolite of [$^{11}$C]loperamide, surprisingly was identified by the inventors to also be a P-gp substrate, and superior to [$^{11}$C]loperamide for imaging P-gp function.

BRIEF SUMMARY OF THE INVENTION

The present invention relates to novel radiotracers for use in imaging P-glycoprotein function.

In one aspect of the present invention radiotracers are provided. A preferred radiotracer of the present invention is a compound according to formula (I)

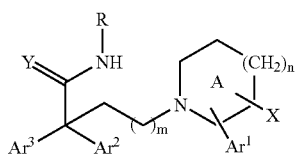

wherein Y is O or S; R is $C_1$-$C_6$ alkyl or $C_1$-$C_6$halo$_6$alkyl, X is selected from the group consisting of hydroxyl and halo; each $Ar^1$ $Ar^2$ and $Ar^3$ is independently aryl or heteroaryl, each of which is optionally substituted with from 1 to 3 substituents, independently selected from the group consisting of halo, hydroxy, amino, $C_1$-$C_6$alkoxy, $C_1$-$C_6$alkylthio, cyano, $C_1$-$C_6$haloalkyl and nitro; n is the integer 0, 1, 2 or 3; and m is the integer 1, 2 or 3, wherein one atom selected from the group consisting of carbon, hydrogen, nitrogen, oxygen and halogen atom comprises or is replaced by a detectable amount of a radioisotope selected from the group consisting of $^{11}$C, $^{13}$N, $^{15}$O, $^{18}$F, $^{76}$Br, and $^{123}$I. The invention also provides and all stereoisomers or pharmaceutically acceptable salts thereof in isolated and purified form. Preferred are the radioisotopes selected from the group consisting of $^{11}$C, $^{3}$H and $^{18}$F. Also preferred are compounds according to formula (I), wherein n=1, 2, or 3, preferably, n=1. Further, a preferred compound according to formula (I) is a compound wherein m=1.

Another preferred compound according to formula (I), is a compound wherein one atom from R comprises or is replaced by a detectable amount of a radioisotope selected from the group consisting of $^{11}$C and $^{3}$H, if $C_1$-$C_6$alkyl, or $^{11}$C, $^{3}$H and $^{18}$F, if $C_1$-$C_6$haloalkyl.

Another preferred compound according to formula (I), is a compound wherein R can also be $C_n(H_{2n+1})$ or $D_{2n+1})^{11}CH_2$ wherein n is the integer 0, 1, 2, 3, 4, 5 or 6. Further, a preferred compound according to formula (I), is a compound wherein R is selected from the group consisting of $^{11}CH_3$, $^{11}CD_3$ and $C^3H_3$ or wherein R is $C_1$-$C_6$haloalkyl.

Also preferred is a compound according to formula (I), wherein R is selected from the group consisting of $C_n(H_{2n}$ or $D_{2n})CH_2^{18}F$ and n is the integer 0, 1, 2, 3, 4, 5 or 6.

Further, this invention provides a compound according to formula (I), wherein R is selected from the group consisting of $CH_2^{18}F$ and $CD_2^{18}F$.

A preferred compound is a compound according to formula (I) wherein $Ar^1$ is phenyl, optionally substituted with from 1 to 3 substitutents independently selected from the group consisting of Cl, Br, F, hydroxy, $NH_2$, $NHCH_3$, $OCH_3$, $SCH_3$, CN, $CF_3$ and nitro.

Further, a preferred compound according to formula (I) wherein $Ar^1$ is pyridyl, optionally substituted with from 1 to 3 substitutents independently selected from the group consisting of Cl, Br, F, hydroxy, $NH_2$, $NHCH_3$, $OCH_3$, $SCH_3$, CN, $CF_3$ and nitro.

Another preferred compound according to formula (I) is a compound wherein $Ar^1$ is 4-chlorophenyl. Other preferred compounds according to formula (I) are compounds wherein either $Ar^2$ or $Ar^3$ are phenyl.

In some compounds according to formula (I), X is selected from the group consisting of hydroxy, Cl, Br and F.

Another preferred radiotracer of the present invention is a compound having the formula (IIa):

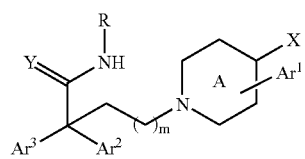

and all stereoisomers or pharmaceutically acceptable salts thereof, wherein Y, R, X, $Ar^1$, $Ar^2$, $Ar^3$, n and m are as defined above.

Another preferred radiotracer of the present invention is a compound having the formula (IIb):

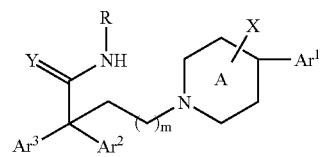

and all stereoisomers or pharmaceutically acceptable salts thereof, wherein Y, R, X, $Ar^1$, $Ar^2$, $Ar^3$, n and m are as defined above.

Another preferred radiotracer of the present invention is a compound having the formula (IIc):

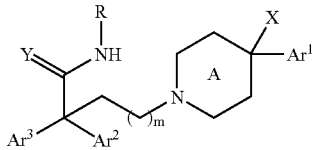

and all stereoisomers or pharmaceutically acceptable salts thereof, wherein Y, R, X, $Ar^1$, $Ar^2$, $Ar^3$, n and m are as defined above.

A preferred compound of the present invention is a compound having the formula (III)

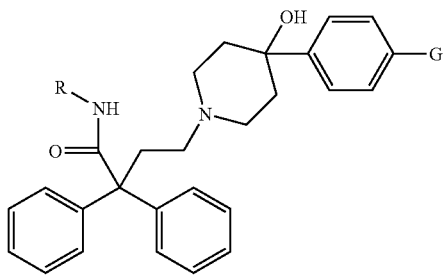

wherein R is $C_1$-$C_6$alkyl or $C_1$-$C_6$haloalkyl, wherein one carbon or halogen atom comprises a detectable amount of a radioisotope; G is selected from the group consisting of $R^1$, $OR^1$, $N(R^1)_2$, CN, $NO_2$, $SR^1$ and halogen; and $R^1$ is $C_1$-$C_6$ alkyl and all stereoisomers or pharmaceutically acceptable salts thereof. Preferred is the compound wherein R=$^{11}CH_3$. In another preferred compound, R=$^{11}CH_3$ and G is chlorine.

Another preferred radiotracer is a compound having the formula (III):

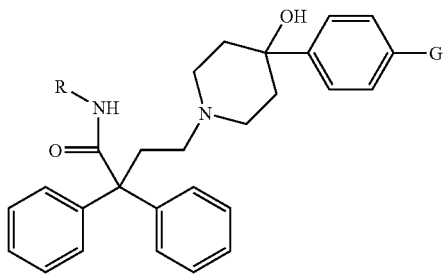

wherein R is $^{11}CH_3$ or R is $C_1$-$C_6$alkyl wherein one C is $^{11}C$ or R is substituted with a radiolabeled halogen atom; G is $R^1$, $OR^1$, $N(R^1)_2$, CN, $NO_2$, $SR^1$, or a halogen; and $R^1$ is $C_1$-$C_6$ alkyl. The invention also provides stereoisomers or pharmaceutically acceptable salts thereof.

In a preferred embodiment of the present invention, in the compound having formula (III), R is $^{11}CH_3$.

In another preferred embodiment of the present invention, in the compound having formula (III), R is $^{11}CH_3$ and G is chlorine.

The present invention further provides radiotracers having a $^{18}F$ radiolabel. Thus, in a preferred embodiment of the present invention, a radiotracer is a compound having the formula (III)

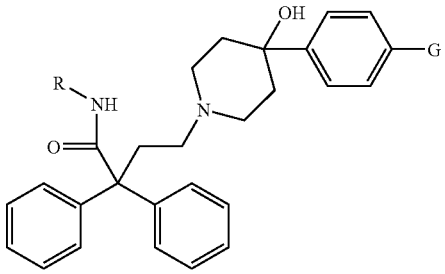

wherein R is $^{18}FH_2C$ or R is $C_1$-$C_6$alkyl wherein one C is substituted by $^{18}F$ or R is substituted with a radiolabeled halogen atom; G is $R^1$, $OR^1$, $N(R^1)_2$, CN, $NO_2$, $SR^1$, or a halogen; and $R^1$ is $C_1$-$C_6$ alkyl. The invention also provides stereoisomers or pharmaceutically acceptable salts thereof.

In a preferred embodiment of the present invention, in the compound having formula (III), R is $^{18}FH_2C$.

In another preferred embodiment of the present invention, in the compound having formula (III), R is $^{18}FH_2C$ and G is chlorine. In other compounds having formula (III), R is $^{18}F(CH_2)_2$ or $^{18}F(CH_2)_3$ and G is chlorine.

In a preferred embodiment of the present invention, the compounds are provided in an isolated and purified form.

In another aspect of the invention pharmaceutical compositions are provided. A preferred pharmaceutical composition comprises (i) a compound selected from the group consisting of a compound having the formula (I), a compound having the formula (IIa), a compound having the formula (IIb), a compound having the formula (IIc), And a compound having the formula (III) and (ii) a pharmaceutically acceptable carrier or excipient.

In a further aspect of the present invention kits or systems are provided. A preferred kit or system comprises (i) a compound selected from the group consisting of a compound having the formula (I), a compound having the formula (IIa), a compound having the formula (IIb), a compound having the formula (IIc), and a compound having the formula (III) and (ii) a preparation of a P-glycoprotein. Another preferred kit or system comprises any compound described herein.

In yet another aspect of the present invention, methods of producing a radiotracer are provided. The invention provides methods of producing a compound according to formula (I). In a preferred embodiment, this method comprises the steps of: (a) reacting a compound having the formula (IV)

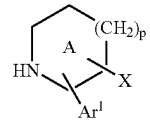

with a compound having the formula (V):

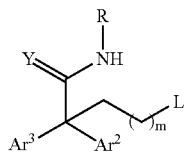

to form a product, (b) hydrolyzing the product from step (a), and (c) N-alkylating the product from step (b) to provide an N-alkyl group R, wherein L is a leaving group, R is $C_1$-$C_6$alkyl or $C_1$-$C_6$haloalkyl, and wherein carbon or halogen atom comprises a detectable amount of a radioisotope. Step (c) can be performed in the presence of [$^{11}$C]iodomethane or in the presence of [$^{11}$C]methyl triflate, or another $^{11}$C-alkylating agent. Preferably, L is a halogen.

Also provided herein are methods of producing a compound according to formula (III). In a preferred embodiment of the present invention, the method of producing a compound according to formula (III) comprises the steps of: (a) reacting a compound having the formula (VI)

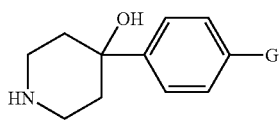

with a compound having the formula (VII):

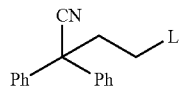

to form a product, (b) hydrolyzing the product from step (a), (c) N-alkylating the product from step (b) to provide an N-alkyl group R, wherein L is a leaving group, R is $C_1$-$C_6$alkyl or $C_1$-$C_6$haloalkyl, and wherein one carbon or halogen atom comprises a detectable amount of a radioisotope. Preferably, R is $^{11}$CH$_3$. Preferably, L is a halogen. Step (c) can be performed in the presence of [$^{11}$C]iodomethane or in the presence of [$^{11}$C]methyl triflate, or another $^{11}$C-alkylating agent.

In another preferred embodiment, a method of producing a compound having formula III comprises (a) reacting a compound having the formula (VI):

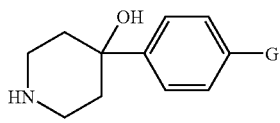

with a compound having the formula (VIII):

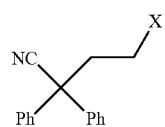

to form a product, (b) hydrolyzing the product, and (c) N-alkylating the hydrolyzed product to provide an N-alkyl group selected from $^{11}$CH$_3$ and R. In this method, X is a leaving group and R is $C_1$-$C_3$ alkyl and one C of the $C_1$-$C_3$ alkyl is $^{11}$C or R is substituted with a radiolabeled atom. Step (c) can be performed in the presence of [$^{11}$C]iodomethane or in the presence of [$^{11}$C]methyl triflate, or another $^{11}$C-alkylating agent. In a preferred method, X is a halogen.

The present invention also provides methods for using the compounds of the present invention. Any compound described herein can be used in the methods described herein.

Thus, in a further aspect of the present invention methods for measuring an interaction of a radiolabeled compound of the invention with a P-glycoprotein are provided. In a preferred embodiment of the present invention, this method comprises the steps of: (a) contacting a P-glycoprotein with a radiolabeled compound selected from the group consisting of a compound having the formula (I), a compound having the formula (IIa), a compound having the formula (IIb), a compound having the formula (IIc), and a compound having the formula (III) to produce a P-glycoprotein-radiolabeled compound complex and (b) measuring an interaction of the radiolabeled compound with the P-glycoprotein. A measurable signal is indicative of the amount of the radiolabeled compound interacting with the P-glycoprotein. The measurable signal is recorded, e.g., in an electronic or optical database.

In an additional aspect of the present invention methods for measuring an interaction of a test compound with a P-glycoprotein are provided. In a preferred embodiment of the present invention, this method comprises the steps of: (a) contacting a P-glycoprotein with a radiolabeled compound selected from the group consisting of a compound having the formula (I), a compound having the formula (IIa), a compound having the formula (IIb), a compound having the formula (IIc), and a compound having the formula (III) to produce a P-glycoprotein-radiolabeled compound complex, (b) measuring an interaction of the radiolabeled compound with the P-glycoprotein; wherein a first measurable signal is obtained, (c) contacting the P-glycoprotein-radiolabeled compound complex with a test compound under conditions whereby the interaction of the radiolabeled compound with the P-glycoprotein is prevented by the test compound, and (d) detecting a second measurable signal. A higher second measurable signal when compared to the first measurable signal is indicative of the test compound interacting with the P-glycoprotein.

In another preferred embodiment of the present invention, the method for measuring an interaction of a test compound with a P-glycoprotein comprises the steps of (a) contacting a P-glycoprotein preparation with a mixture comprising (i) a radiolabeled compound selected from the group consisting of a compound having the formula (I), a compound having the formula (IIa), a compound having the formula (IIb), a compound having the formula (IIc), and a compound having the formula (III) and (ii) a test compound to produce a P-glycoprotein-radiolabeled compound complex and a P-glycoprotein-test compound complex, (b) measuring the interaction of the radiolabeled compound with the P-glycoprotein to obtain a first measurable signal, and (c) comparing the first measurable signal to a second measurable signal obtained by contacting the P-glycoprotein with the radiolabeled compound in the absence of the test compound. A lower first measurable signal when compared to the second measurable signal is indicative of the test compound interacting with the P-glycoprotein.

The P-glycoprotein preparation can be a P-glycoprotein membrane preparation or a whole cell preparation. The P-glycoprotein may be bound to a solid support.

In a further aspect of the present invention, methods for assessing P-glycoprotein function in a subject having a neurological condition, such as Alzheimer's disease, Parkinson's disease, or dementia, and the like, are provided. In a preferred embodiment of the invention, this method comprises the steps of (a) administering a radiolabeled compound selected from the group consisting of a compound having the formula (I), a compound having the formula (IIa), a compound having the formula (IIb), a compound having the formula (IIc), and a compound having the formula (III) to the subject and (b) measuring transport of the radiolabeled compound across the blood brain barrier.

In yet another aspect of the present invention, methods for assessing multidrug resistance in a subject are provided. In a preferred embodiment of the present invention, this method comprises the steps of (a) administering a radiolabeled compound selected from the group consisting of a compound having the formula (I), a compound having the formula (IIa), a compound having the formula (IIb), a compound having the formula (IIc), and a compound having the formula (III) to the subject and (b) assessing transport of the radiolabeled compound across the blood brain barrier.

In another aspect of the present invention, methods of assessing treatment of or for a subject with multidrug resistance are provided. In a preferred embodiment of the present invention, this method comprises the steps of (a) administering a radiolabeled compound selected from the group consisting of a compound having the formula (I), a compound having the formula (IIa), a compound having the formula (IIb), a compound having the formula (IIc), and a compound having the formula (III) and a P-glycoprotein inhibitor to a subject and (b) determining transport of the compound across the blood brain barrier.

DETAILED DESCRIPTION OF THE INVENTION

Figure 1:
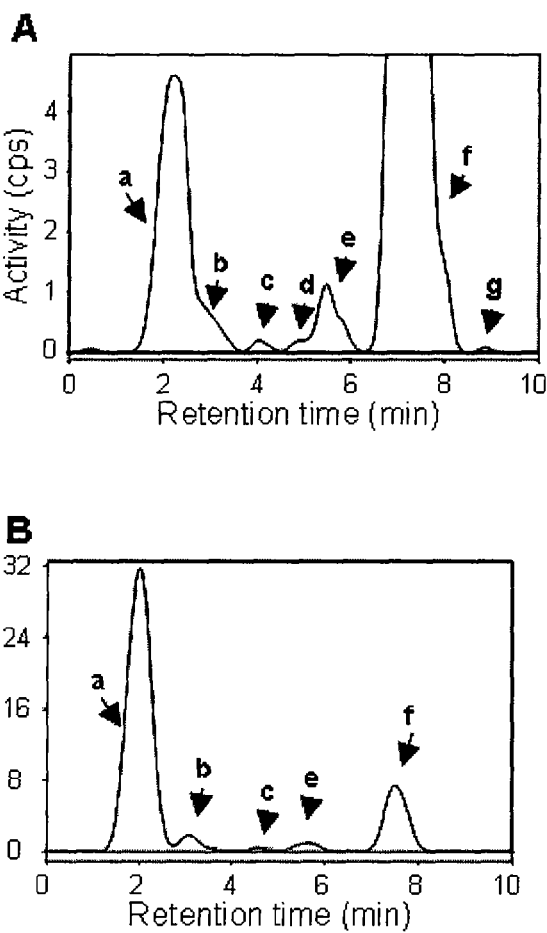
FIG. 1 depicts radiochromatograms of activity extracted from plasma of monkey (A) and mouse (B). Monkey plasma was obtained 15 min after intravenous injection of [$^{11}$C] loperamide, and mouse plasma at 30 min. Radiometabolites a, b, c, d, e were all more polar than [$^{11}$C]loperamide peak f, but the minor peak g was more lipophilic than parent. Details are described in Examples 4 and 8.

The present invention may be understood more readily by reference to the following detailed description of preferred embodiments of the invention, the Examples included therein, and to the Figures.

I. Definitions

Unless defined otherwise, all technical and scientific terms used herein have the meaning commonly understood by a person skilled in the art to which this invention belongs. The following references provide one of skill with a general definition of many of the terms used in this invention: Singleton et al., *Dictionary of Microbiology and Molecular Biology* (2nd ed. 1994); *The Cambridge Dictionary of Science and Technology* (Walker ed., 1988); *The Glossary of Genetics*, 5th Ed., Rieger et al. (eds.), Springer Verlag (1991); and Hale & Marham, *The Harper Collins Dictionary of Biology* (1991). As used herein, the following terms have the meanings ascribed to them unless specified otherwise.

It must be noted that, as used in the specification and the appended claims, the singular forms "a," "an" and "the" include plural referents unless the context clearly dictates otherwise. Thus, for example, reference to "a compound" includes mixtures of compounds, reference to "a pharmaceutical carrier" includes mixtures of two or more such carriers, and the like.

As used herein, the term "alkyl" refers to a straight or branched chain hydrocarbon radical, and can include di- and multivalent radicals, having the number of carbon atoms designated (i.e. $C_1$-$C_6$ means one to six carbons). Examples of saturated hydrocarbon radicals include groups such as methyl, ethyl, n-propyl, isopropyl, n-butyl, t-butyl, isobutyl, sec-butyl, homologs and isomers of, for example, n-pentyl, n-hexyl, n-heptyl, n-octyl, and the like.

As used herein, the term "alkenyl" refers to an unsaturated alkyl group one having one or more double bonds. Examples of alkenyl groups include vinyl, 2-propenyl, crotyl, 2-isopentenyl, 2-(butadienyl), 2,4-pentadienyl and 3-(1,4-pentadienyl), and the higher homologs and isomers.

As used herein, the term "alkynyl" refers to an unsaturated alkyl group one having one or more triple bonds. Examples of alkynyl groups include ethynyl (acetylenyl), 1-propynyl, 1- and 2-butynyl, and the higher homologs and isomers.

As used herein, the term "aryl" refers to an aromatic hydrocarbon having 5-12 carbon ring members, which can be a single ring or multiple rings (up to three rings) which are fused together or linked covalently. Non-limiting examples of aryl groups include phenyl, 1-naphthyl, 2-naphthyl, 4-biphenyl, and benzyl. Other aryl groups are also useful in the present invention, including heteroaryl groups in which the heteroatom may be nitrogen.

"Heteroaryl" refers to a cyclic or polycyclic aromatic radical that contain from one to five heteroatoms selected from N, O, and S, wherein the nitrogen and sulfur atoms are optionally oxidized, and the nitrogen atom(s) are optionally quaternized. A heteroaryl group can be attached to the remainder of the molecule through a heteroatom or through a carbon atom and can contain 5 to 10 carbon atoms. Non-limiting examples of heteroaryl groups include 1-pyrrolyl, 2-pyrrolyl, 3-pyrrolyl, 1-pyrazolyl, 3-pyrazolyl, 2-imidazolyl, 4-imidazolyl, pyrazinyl, 2-oxazolyl, 4-oxazolyl, 5-oxazolyl, 3-isoxazolyl, 4-isoxazolyl, 5-isoxazolyl, 2-thiazolyl, 4-thiazolyl, 5-thiazolyl, 2-furyl, 3-furyl, 2-thienyl, 3-thienyl, 2-pyridyl, 3-pyridyl, 4-pyridyl, 2-pyrimidyl and 4-pyrimidyl. If not specifically stated, substituents for each of the above noted aryl and heteroaryl ring systems are selected from the group of acceptable substituents described herein. "Substituted heteroaryl" refers to a unsubstituted heteroaryl group as defined above in which one or more of the ring members is bonded to a non-hydrogen atom such as described above with respect to substituted alkyl groups and substituted aryl groups. Representative substituents include straight and branched chain alkyl groups-$CH_3$, —$C_2H_5$, —$CH_2OH$, —OH, —$OCH_3$, —$OC_2H_5$, —$OCF_3$, —OC(=O)$CH_3$, —OC(=O)$NH_2$, —OC(=O)N($CH_3$)$_2$, —CN, —$NO_2$, —C(=O)$CH_3$, —$CO_2H$, —$CO_2CH_3$, —$CONH_2$, —$NH_2$,—N($CH_3$)$_2$, —$NHSO_2CH_3$, —NHCOCH$_3$, —NHC(=O)OCH$_3$,—NHSO—$_2CH_3$,—$SO_2CH_3$, —$SO_2NH_2$ and halo.

In each of the above embodiments designating a number of atoms e.g. "$C_{1-8}$" is meant to include all possible embodiments that have one fewer atom. Non-limiting examples include $C_{1-7}$, $C_{2-8}$, $C_{2-7}$, $C_{3-8}$, $C_{3-7}$ and the like.

Each of the terms herein (e.g., "alkyl," "heteroalkyl," "aryl" and "heteroaryl") is meant to include both "unsubstituted" and optionally "substituted" forms of the indicated radical, unless otherwise indicated. Typically each radical is substituted with 0, 1, 2 3 4 or 5 substituents, unless otherwise indicated. Examples of substituents for each type of radical are provided below.

"Substituted" refers to a group as defined herein in which one or more bonds to a carbon(s) or hydrogen(s) are replaced by a bond to non-hydrogen and non-carbon atom "substituents" such as, but not limited to, a halogen atom such as F, Cl, Br, and I; an oxygen atom in groups such as hydroxyl groups, alkoxy groups, aryloxy, and acyloxy groups; a sulfur atom in groups such as thiol groups, alkyl and aryl sulfide groups, sulfone groups, sulfonyl groups, and sulfoxide groups; a nitrogen atom in groups such as amino, alkylamines, dialkylamines, arylamines, alkylarylamines, diarylamines, alkoxyamino, hydroxyamino, acylamino, sulfonylamino, N-oxides, imides, and enamines; and other heteroatoms in various other groups. "Substituents" also include groups in which one or more bonds to a carbon(s) or hydrogen(s) atom is replaced by a higher-order bond (e.g., a double- or triple-bond) to a heteroatom such as oxygen in oxo, acyl, amido, alkoxycarbonyl, aminocarbonyl, carboxyl, and ester groups; nitrogen in groups such as imines, oximes, hydrazones, and nitriles. "Substituents" further include groups in which one or more bonds to a carbon(s) or hydrogen(s) atoms is replaced by a bond to a cycloalkyl, heterocyclyl, aryl, and heteroaryl groups. Representative "substituents" include, among others, groups in which one or more bonds to a carbon or hydrogen atom is/are replaced by one or more bonds to fluoro, chloro, or bromo group. Another representative "substituent" is the trifluoromethyl group and other groups that contain the trifluoromethyl group. Other representative "substituents" include those in which one or more bonds to a carbon or hydrogen atom is replaced by a bond to an oxygen atom such that the substituted alkyl group contains a hydroxyl, alkoxy, or aryloxy group. Other representative "substituents" include alkyl groups that have an amine, or a substituted or unsubstituted alkylamine, dialkylamine, arylamine, (alkyl)(aryl)amine, diarylamine, heterocyclylamine, diheterocyclylamine, (alkyl)(heterocyclyl)amine, or (aryl)(heterocyclyl)amine group. Still other representative "substituents" include those in which one or more bonds to a carbon(s) or hydrogen(s) atoms is replaced by a bond to an alkyl, cycloalkyl, aryl, heteroaryl, or heterocyclyl group.

The herein-defined groups may include prefixes and/or suffixes that are commonly used in the art to create additional well-recognized substituent groups. As examples, "alkylamino" refers to a group of the formula —$NR^aR^b$. Unless stated otherwise, for the following groups containing $R^a$, $R^b$, $R^c$, $R^d$ and $R^e$: $R^a$, and $R^b$ are each independently selected from H, alkyl, alkoxy, thioalkoxy, cycloalkyl, aryl, heteroaryl, or heterocyclyl or are optionally joined together with the atom(s) to which they are attached to form a cyclic group. When $R^a$ and $R^b$ are attached to the same nitrogen atom, they can be combined with the nitrogen atom to form a 5-, 6- or 7-membered ring. For example, —$NR^aR^b$ is meant to include 1-pyrrolidinyl and 4-morpholinyl.

$R^c$, $R^d$, $R^e$ and $R^f$ are each independently selected from alkyl, alkenyl, alkynyl, cycloalkyl, cycloalkenyl, aryl, heteroaryl, heterocyclyl or alkylenearyl as defined herein.

Typically, a particular radical will have 0, 1, 2 or 3 substituents, with those groups having two or fewer substituents being preferred in the present invention. More preferably, a radical will be unsubstituted or monosubstituted. Most preferably, a radical will be unsubstituted.

"Substituents" for the alkyl and heteroalkyl radicals (as well as those groups referred to as alkylene, alkenyl, heteroalkylene, heteroalkenyl, alkynyl, cycloalkyl, heterocyclyl) can be a variety of groups selected from: —$OR^a$, =O, =$NR^a$, =N—$OR^a$, —$NR^aR^b$, —$SR^a$, halogen, —$SiR^aR^bR^c$, —$OC(O)R^a$, —$C(O)R^a$, —$CO_2R^a$, —$CONR^aR^b$, —$OC(O)NR^aR^b$, —$NR^bC(O)R^a$, —$NR^a$—$C(O)NR^bR^c$, —$NR^a$—$SO_2NR^bR^c$, —$NR^bCO_2R^a$, —NH—$C(NH_2)$=NH, —$NR^aC(NH_2)$=NH, —NH—$C(NH_2)$=$NR^a$, —$S(O)R^a$, —$SO_2R^a$, —$SO_2NR^aR^b$, —$NR^bSO_2R$, —CN and —NO2, in a number ranging from zero to three, with those groups having zero, one or two substituents being particularly preferred.

In some embodiments, "substituents" for the alkyl and heteroalkyl radicals are selected from: —$OR^a$, =O, —$NR^aR^b$, —$SR^a$, halogen, —$SiR^aR^bR^c$, —$OC(O)R^a$, —$C(O)R^a$, —$CO_2R^a$, —$CONR^aR^b$, —$OC(O)NR^aR^b$, —$NR^bC(O)R^a$, —$NR^bCO_2R^a$, —$NR^a$—$SO_2NR^bR^c$, —$S(O)R^a$, —$SO_2R^a$, —$SO_2NR^aR^b$, —$NR^aSO_2R$, —CN and —NO2, where $R^a$ and $R^b$ are as defined above. In some embodiments, substituents are selected from: —$OR^a$, =O, —$NR^aR^b$, halogen, —$OC(O)R^a$, —$CO_2R^a$, —$CONR^aR^b$, —$OC(O)NR^aR^b$, —$NR^bC(O)R^a$, —$NR^bCO_2R^a$, —$NR^a$—$SO_2NR^bR^c$, —$SO_2R^a$, —$SO_2NR^aR^b$, —$NR"SO_2R$, —CN and —NO2.

Examples of substituted alkyl are: —$(CH_2)_3NH_2$, —$(CH_2)_3NH(CH_3)$, —$(CH_2)_3NH(CH_3)_2$, —$CH_2C(=CH_2)$ $CH_2NH_2$, —$CH_2C(=O)CH_2NH_2$, —$CH_2S(=O)_2CH_3$, —$CH_2$ $OCH_2NH_2$, —$CO_2H$. Examples of substituents of substituted alkyl are: $CH_2OH$, —OH, —$OCH_3$, —$OC_2H_5$, —$OCF_3$, —$OC(=O)CH_3$, —$OC(=O)NH_2$, —$OC(=O)N$ $(CH_3)_2$, —CN, —$NO_2$, —$C(=O)CH_3$, —$CO_2H$, —$CO_2CH_3$, —$CONH_2$, —$NH_2$, —$N(CH_3)_2$, —$NHSO_2CH_3$, —$NHCOCH_3$, —$NHC(=O)OCH_3$, —$NHSO—_2CH_3$, —$SO_2CH_3$, —$SO_2NH_2$, and halo.

Similarly, "substituents" for the aryl and heteroaryl groups are varied and are selected from: -halogen, —$OR^a$, —OC(O) $R^a$, —$NR^aR^b$, —$SR^a$, —$R^a$, —CN, —NO2, —$CO_2R^a$, —$CONR^aR^b$, —$C(O)R^a$, —$OC(O)NR^aR^b$, —$NR^bC(O)R^a$, —$NR^bC(O)2R^a$, —$NR^a$—$C(O)NR^bR^c$, —NH—$C(NH2)$ =NH, —$NR^aC(NH2)$=NH, —NH—$C(NH2)$=$NR^a$, —$S(O)$ $R^a$, —$S(O)2R^a$, —$S(O)2NR^aR^b$, —N3, —$CH(Ph)2$, perfluoroC1-8alkoxy, and perfluoroC1-8alkyl, in a number ranging from zero to the total number of open valences on the aromatic ring system; and where $R^a$, $R^b$ and $R^c$ are independently selected from hydrogen, C1-6alkyl and heteroalkyl, unsubstituted aryl and heteroaryl, (unsubstituted aryl)-C1-8alkyl, and (unsubstituted aryl)oxy-C1-8alkyl.

Two or three of the "substituents" on adjacent atoms of the aryl or heteroaryl ring may optionally be replaced with a substituent of the formula -T-C(O)—(CH2)q-U—, wherein T and U are independently —NH—, —O—, —CH2- or a single bond, and q is 0, 1 or 2. Alternatively, two of the substituents on adjacent atoms of the aryl or heteroaryl ring may optionally be replaced with a substituent of the formula -A-(CH2)r-B—, wherein A and B are independently —CH2-, —O—, —NH—, —S—, —S(O)—, —S(O)2-, —$S(O)2NR^{a-}$ or a single bond, and r is 1, 2 or 3. One of the single bonds of the new ring so formed may optionally be replaced with a double bond. Alternatively, two of the substituents on adjacent atoms of the aryl or heteroaryl ring may optionally be replaced with a substituent of the formula —(CH2)s-X—(CH2)t- -, where s and t are independently integers of from 0 to 3, and X is —O—, —$NR^{a-}$, —S—, —S(O)—, —S(O)2-, or —$S(O)2NR^{a-}$. The substituent $R^a$ in —$NR^{a-}$ and —S(O) $2NR^{a-}$ is selected from hydrogen or unsubstituted C1-6alkyl. Otherwise, R' is as defined above.

Unless indicated otherwise, the nomenclature of substituents that are not explicitly defined herein are arrived at by naming the terminal portion of the functionality followed by the adjacent functionality toward the point of attachment. For example, the substituent "arylalkyloxycarbonyl" refers to the group (aryl)-(alkyl)-O—C(O)—.

"Alkoxy" refers to —$OR^d$ wherein $R^d$ is alkyl as defined herein. Representative examples of alkoxy groups include methoxy, ethoxy, t-butoxy, trifluoromethoxy, and the like.

"Amino" refers to a monovalent radical —$NR^aR^b$ or divalent radical —$NR^a$—. The term "alkylamino" refers to the group —$NR^aR^b$ where $R^a$ is alkyl and $R^b$ is H or alkyl. The term "arylamino" refers to the group —$NR^aR^b$ where at least one $R^a$ or $R^b$ is aryl. The term "(alkyl)(aryl)amino" refers to the group —$NR^aR^b$ where $R^a$ is alkyl and $R^b$ is aryl. Additionally, for dialkylamino groups, the alkyl portions can be the same or different and can also be combined to form a 3-7 membered ring with the nitrogen atom to which each is attached. Accordingly, a group represented as —$NR^aR^b$ is meant to include piperidinyl, pyrrolidinyl, morpholinyl, azetidinyl and the like.

"Cyano" refers to —CN.

As used herein, the term "biological sample" refers to a sample of biological tissue or fluid that contains nucleic acids or polypeptides, e.g., of a breast cancer protein, polynucleotide or transcript. Such samples are typically from humans, but include tissues isolated from non-human primates (e.g., monkeys) or rodents (e.g., mice, and rats). Numerous types of biological samples can be used in the present invention, including, but not limited to, sections of tissues such as biopsy and autopsy samples, frozen sections taken for histologic purposes, blood, plasma, serum, sputum, stool, tears, mucus, hair, skin, etc. Biological samples also include explants and primary and/or transformed cell cultures derived from patient tissues. A "biological sample" also refers to a cell or population of cells or a quantity of tissue or fluid from an animal. Most often, the sample has been removed from an animal, but the term "biological sample" can also refer to cells or tissue analyzed in vivo, i.e., without removal from the animal.

"Cancer cell," "transformed" cell or "transformation" in tissue culture, refers to spontaneous or induced phenotypic changes that do not necessarily involve the uptake of new genetic material. Although transformation can arise from infection with a transforming virus and incorporation of new genomic DNA, or uptake of exogenous DNA, it can also arise spontaneously or following exposure to a carcinogen, thereby mutating an endogenous gene. Transformation is associated with phenotypic changes, such as immortalization of cells, aberrant growth control, nonmorphological changes, and/or malignancy (see, Freshney, *Culture of Animal Cells a Manual of Basic Technique* (3rd ed. 1994)). A preferred cancer cell is a cancer cell characterized by showing multidrug resistance to one or more chemotherapeutic drugs.

"Correlating an amount" means comparing an amount of a substance, molecule or marker (such as radiotracer) that has been determined in one sample to an amount of the same substance, molecule or marker determined in another sample. The amount of the same substance, molecule or marker determined in another sample may be specific for a given cancer or disorder.

The abbreviation "DAT" refers to dopamine transporter.

The abbreviation "DCPQ" refers to ((2R)-anti-5-{3-[4-(10,11-dichloromethanodibenzosuber-5-yl)piperazin-1-yl]-2-hydroxypropoxy}quinoline trihydrochloride.

Synonyms of the term "determining an amount" are contemplated within the scope of the present invention and include, but are not limited to, detecting, measuring, testing or determining, the presence, absence, amount or concentration of a molecule, such as a radiotracer or a radiometabolite of a radiotracer.

By "determining a functional effect" is meant assaying for a compound that increases or decreases a parameter that is indirectly or directly under the influence of that compound (e.g., a radiotracer), e.g., functional, enzymatic, physical and chemical effects. Such functional effects can be measured by any means known to those skilled in the art, e.g., changes in P-gp imaging, PET scanning, SPECT analysis, spectroscopic characteristics (e.g., fluorescence, absorbance, refractive index), hydrodynamic (e.g., shape), chromatographic, or solubility properties for the protein, measuring inducible markers or transcriptional activation of a P-gp; measuring binding activity, e.g., binding of a radiotracer to a P-gp, measuring cellular proliferation, measuring apoptosis, or the like. Determination of the functional effect of a compound on cancer can also be performed using assays known to those of skill in the art such as an in vitro assays, e.g., cell growth on soft agar; anchorage dependence; contact inhibition and density limitation of growth; cellular proliferation; cellular transformation; growth factor or serum dependence; tumor specific marker levels; invasiveness into Matrigel; tumor growth and metastasis in vivo; mRNA and protein expression in cells undergoing metastasis, and other characteristics of cancer cells. The functional effects can be evaluated by many means known to those skilled in the art, e.g., microscopy for quantitative or qualitative measures of alterations in morphological features, measurement of changes in P-gp RNA or protein levels. "Functional effects" include in vitro, in vivo, and ex vivo activities.

The abbreviation "DIPEA" refers to N,N-diisopropylethylamine.

The abbreviation "dLop" refers to N-desmethyl-loperamide. The abbreviation "Lop" refers to loperamide.

As used herein, the term "drug resistance" refers to the circumstance when a disease does not respond to a treatment drug. Drug resistance can be either intrinsic or acquired.

As used herein, the terms "effective amount" or "therapeutic amount" refers to the amount of an active compound, e.g., a compound of the present invention, such as a radiotracer, to provide an effect or effectiveness that is desirable and that is an intended effect associated with the administration of the active compound according to the invention.

As used herein, the term "halogen" refers to the elements including fluorine (F), chlorine (Cl), bromine (Br) and iodine (I).

"Hydroxy" or "hydroxyl" refers to the group —OH.

As used herein, an "inhibitor of a transporter" refers to a compound that binds to a MDR protein, such as MDR1, MDR2, or P-gp, and either completely blocks or merely slows transport of an active agent across biological barriers. An inhibitor of a transporter is expected to increase the efficacy of an active agent. A transporter inhibitor, e.g., reduces efflux across the cellular membrane of a cancer cell, increases influx into the cancer cell, and/or inhibits a host drug transporter.

Compounds that have the same molecular formula but differ in the nature or sequence of bonding of their atoms or the arrangement of their atoms in space are termed "isomers". Isomers that differ in the arrangement of their atoms in space are termed "stereoisomers". "Stereoisomer" and "stereoisomers" refer to compounds that exist in different stereoisomeric forms if they possess one or more asymmetric centers or a double bond with asymmetric substitution and, therefore, can be produced as individual stereoisomers or as mixtures. Stereoisomers include enantiomers and diastereomers. Stereoisomers that are not mirror images of one another are termed "diastereomers" and those that are non-superimposable mirror images of each other are termed "enantiomers". When a compound has an asymmetric center, for example, it is bonded to four different groups, a pair of enantiomers is possible. An enantiomer can be characterized by the absolute configuration of its asymmetric center and is described by the R— and S-sequencing rules of Cahn and Prelog, or by the manner in which the molecule rotates the plane of polarized light and designated as dextrorotatory or levorotatory (i.e., as (+) or (−)-isomers respectively). A chiral compound can exist as either individual enantiomer or as a mixture thereof. A mixture containing equal proportions of the enantiomers is called a "racemic mixture". Unless otherwise indicated, the description is intended to include individual stereoisomers as well as mixtures. The methods for the determination of stereochemistry and the separation of stereoisomers are well-known in the art (see discussion in Chapter 4 of ADVANCED ORGANIC CHEMISTRY, 4th edition J. March, John Wiley and Sons, New York, 1992) differ in the chirality of one or more stereocenters.

As used herein, a "label" or "radiolabel" is a composition detectable by spectroscopic, photochemical, biochemical, immunochemical, chemical, or other physical means. For example, useful radiolabels include, but are not limited to, $^{11}C$, $^{18}F$, $^{15}O$, $^{13}N$, $^{99m}Tc$, or $^{94m}Tc$ or other entities which can be made detectable, e.g., by incorporating a radiolabel into a compound.

As used herein, the term "multidrug resistance" refers to a specific type of drug resistance characterized by cross-resistance of a disease to more than one functionally and/or structurally unrelated drugs. The term "transporter-mediated multidrug resistance" refers to multidrug resistance due to the activity of a drug transporter protein.

The abbreviation "NET" refers to noradrenaline transporter.

"Nitro" refers to —$NO_2$.

The terms "optional" or "optionally" as used throughout the specification means that the subsequently described event or circumstance may but need not occur, and that the description includes instances where the event or circumstance occurs and instances in which it does not. For example, "heterocyclo group optionally mono- or di-substituted with an alkyl group means that the alkyl may but need not be present, and the description includes situations where the heterocyclo group is mono- or disubstituted with an alkyl group and situations where the heterocyclo group is not substituted with the alkyl group.

"Optionally substituted" means a ring which is optionally substituted independently with substituents. A site of a group that is unsubstituted may be substituted with hydrogen.

The abbreviation "PET" refers to positron emission tomography.

The abbreviation "P-gp" refers to P-glycoprotein. Nucleotide and amino acid sequences from mammalian P-gps, including mouse, rat, monkey, and human are known in the art and are accessible by, e.g., GenBank.

As used herein, the term "P-gp transporter-mediated multidrug resistance" or grammatical equivalents thereof refer to multidrug resistance due to the activity of a P-gp drug transporter protein.

The term "pharmaceutically acceptable" refers to compositions that are physiologically tolerable and do not typically produce an allergic or similar untoward reaction when administered to a subject, preferably a human subject. Preferably, as used herein, the term "pharmaceutically acceptable" means approved by a regulatory agency of a Federal or state government or listed in the U.S. Pharmacopeia or other generally recognized pharmacopeia for use in animals, and more particularly in humans.

As used herein, the term "prodrug" refers to compounds that readily undergo chemical changes under physiological conditions to provide the compounds of the present invention. Additionally, prodrugs can be converted to the compounds of the present invention by chemical or biochemical methods in an ex vivo environment. For example, prodrugs can be slowly converted to the compounds of the present invention when placed in a transdermal patch reservoir with a suitable enzyme or chemical reagent.

"Providing a biological sample" means to obtain a biological sample for use in methods described in this invention. Most often, this will be done by removing a sample of cells from a patient, but can also be accomplished by using previously isolated cells (e.g., isolated by another person, at another time, and/or for another purpose), or by performing the methods of the invention in vivo. Archival tissues, having treatment or outcome history, will be particularly useful.

The terms "purified," "isolated," or "biologically pure" refer to material that is substantially or essentially free from components that normally accompany it as found in its native state. Purity and homogeneity are typically determined using analytical chemistry techniques such as polyacrylamide gel electrophoresis or high performance liquid chromatography or mass spectrometry. A compound that is the predominant species present in a preparation is substantially purified. The term "purified" or "isolated" in some embodiments denotes that a compound gives rise to essentially one band or peak in an analytical analysis. Preferably, it means that the compound is at least 85% pure, more preferably at least 95% pure, and most preferably at least 99% pure. "Purify," "isolate" or "purification," or "isolation" in other embodiments means removing at least one contaminant from the composition to be purified. In this sense, purification does not require that the purified compound be homogenous, e.g., 100% pure.

As used herein, the term "radiotracer" refers to a compound into which a radionuclide suitable for PET or SPECT scanning is incorporated. Useful radionuclides are isotopes with short half-lives, such as $^{11}C$, $^{13}N$, $^{15}O$, $^{18}F$, $^{76}Br$, and $^{123}I$.

The abbreviation "RCY" refers to decay-corrected radiochemical yield.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, e.g., recombinant cells express genes that are not found within the native (non-recombinant) form of the cell or express native genes that are otherwise abnormally expressed, under expressed or not expressed at all. By the term "recombinant nucleic acid" herein is meant nucleic acid, originally formed in vitro, in general, by the manipulation of nucleic acid, e.g., using polymerases and endonucleases, in a form not normally found in nature. In this manner, operably linkage of different sequences is achieved. Thus, an isolated nucleic acid, in a linear form, or an expression vector formed in vitro by ligating DNA molecules that are not normally joined, are both considered recombinant for the purposes of this invention. It is understood that once a recombinant nucleic acid is made and reintroduced into a host cell or organism, it will replicate non-recombinantly, i.e., using the in vivo cellular machinery of the host cell rather than in vitro manipulations; however, such nucleic acids, once produced recombinantly, although subsequently replicated non-recombinantly, are still considered recombinant for the purposes of the invention. Similarly, a "recombinant protein" is a protein made using recombinant techniques, i.e., through the expression of a recombinant nucleic acid as depicted above.

By "resistant to chemotherapeutic agents," "resistant to chemotherapeutic drugs," or "resistant to chemotherapeutic compounds," herein is meant a tumor or cancer cell hat does not respond to treatment with a chemotherapeutic agent, i.e., is not killed by, or growth-inhibited by, such treatment.

The abbreviation "SA" refers to specific radioactivity.

As used herein, the term "salts" refers to salts of a compound which is prepared with relatively nontoxic acids or bases, depending on the particular substituents found on the compounds described herein. When compounds of the present invention contain relatively acidic functionalities, base addition salts can be obtained by contacting the neutral form of such compounds with a sufficient amount of the desired base, either neat or in a suitable inert solvent. Examples of pharmaceutically acceptable base addition salts include sodium, potassium, calcium, ammonium, organic amino, or magnesium salt, or a similar salt. When compounds of the present invention contain relatively basic functionalities, acid addition salts can be obtained by contacting the neutral form of such compounds with a sufficient amount of the desired acid, either neat or in a suitable inert solvent. Examples of pharmaceutically acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from relatively nontoxic organic acids like acetic, propionic, isobutyric, maleic, malonic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (see, for example, Berge et al., 1977, "Pharmaceutical Salts", *Journal of Pharmaceutical Science,* 66:1-19). Certain specific compounds of the present invention contain both basic and acidic functionalities that allow the compounds to be converted into either base or acid addition salts.

The neutral forms of a compound may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present invention.

As used herein, the term "solid support" refers to any insoluble material including particles (e.g., beads), fibers, monoliths, membranes, filters, plastic strips and the like.

As used herein, the term "solvates" refers to compounds of the present invention that are complexed to a solvent. Solvents that can form solvates with the compounds of the present invention include common organic solvents such as alcohols (methanol, ethanol, etc.), ethers, acetone, ethyl acetate, halogenated solvents (methylene chloride, chloroform, etc.), hexane and pentane. Additional solvents include water. When water is the complexing solvent, the complex is termed a "hydrate."

The abbreviation "SPECT" refers to single photon emission computed tomography.

The terms "subject" or "patient" refer to a mammal, preferably a human, in need of treatment for a condition, such as cancer, disorder, or disease or in need of a diagnostic evaluation.

The term "substantially free" or similar grammatical equivalents refers to a preparation of a compound of interest which does not include detectable amounts of impurities which would inhibit, block or interfere with a function or activity of the compound of interest.

As used herein, the terms "test compound" or "test agent" refer to any compound which may act as a substrate or inhibitor of a P-gp. A 'substrate' interacts with P-gp and is transported/excreted from the cell by it. An 'inhibitor' is bound to P-gp and inhibits binding and/or transportation/excretion of a P-gp substrate or ligand.

As used herein, a "tissue biopsy" refers to an amount of tissue removed from an animal for diagnostic analysis. In a patient with cancer, tissue may be removed from a tumor, allowing the analysis of cells within the tumor. "Tissue biopsy" can refer to any type of biopsy, such as needle biopsy, fine needle biopsy, surgical biopsy, etc.

As used herein, the term "transporter" refers to a protein for the carrier-mediated influx and efflux of drugs and endocytosis of biologically active molecules across a cell membrane barrier, including across a gut, liver, or blood-brain barrier. Preferably the transporter protein is a multidrug resistance protein (MDR), such as MDR1, MDR2, or P-gp.

As used herein, the terms "treat", "treating", and "treatment" include: (1) preventing a disease, such as cancer, i.e. causing the clinical symptoms of the disease not to develop in a subject that may be predisposed to the disease but does not yet experience any symptoms of the disease; (2) inhibiting the disease, i.e. arresting or reducing the development of the disease or its clinical symptoms; or (3) relieving the disease, i.e. causing regression of the disease or its clinical symptoms. Treatment means any manner in which the symptoms or pathology of a condition, disorder, or disease are ameliorated or otherwise beneficially altered. Preferably, the subject in need of such treatment is a mammal, more preferable a human.

"Tumor cell" refers to precancerous, cancerous, and normal cells in a tumor.

II. Radiotracers

P-gp acts as a pump at the blood-brain barrier to exclude a wide range of xenobiotics (e.g., toxins, drugs, etc.) from the brain and is also expressed in a tumors in response to exposure to established or prospective chemotherapeutics (a phenomenon known as multidrug resistance). This invention concerns the preparation and use of radiotracers for imaging P-gp function in vitro and in vivo. Radiotracers of the present invention are avid substrates for P-gp and have structures based on N-desmethyl-loperamide and N-desmethyl-loperamide-related compounds. Among others, these radiotracers possess favorable metabolic properties relative to other radiotracers, including those based on loperamide. The metabolic properties of the radiotracers of the present invention confer much greater specificity in the measurement of P-gp function with an imaging modality such as PET.

As described above, it is an objective of the present invention to provide novel radiotracers which are not limited in their use by the shortcomings of presently available radiotracers. Radiotracers of the present invention, also referred to as radioligands and radiolabeled compounds from time to time, are useful for assessing P-gp function, particularly in patient populations, and preferably in subjects having cancer who are candidates for cancer chemotherapy. Further, radiotracers of the present invention are useful in drug development and drug discovery, for example, in neuroscience to assess the interaction of drugs with P-gp at the blood-brain barrier. In addition, radiotracers of the present invention are also useful for clinical investigation of P-gp function in neuropsychiatric disorders.

A. Radiotracers

The present invention provides novel radiotracers for uses described herein. In one embodiment, a radiotracer of the present invention is a compound according to formula (I)

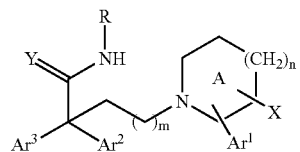

wherein Y is O or S; R is $C_1$-$C_6$ alkyl or $C_1$-$C_6$halo$_6$alkyl wherein one carbon or halogen atom comprises a detectable amount of a radioisotope selected from the group consisting of $^{11}C$ and $^{3}H$ or if haloalkyl, $^{11}C$, $^{3}H$ and $^{18}F$; X is selected from the group consisting of hydroxyl and halo; each $Ar^1$ $Ar^2$ and $Ar^3$ is independently aryl or heteroaryl, each of which is optionally substituted with from 1 to 3 substituents, independently selected from the group consisting of halo, hydroxy, amino, $C_1$-$C_6$alkoxy, $C_1$-$C_6$alkylthio, cyano, $C_1$-$C_6$haloalkyl and nitro; n is the integer 0, 1, 2 or 3; and m is the integer 1, 2 or 3. The invention also provides all stereoisomers or pharmaceutically acceptable salts thereof.

In a preferred embodiment of the compound according to formula (I), Y is O.

In another preferred embodiment of the compound according to formula (I), Y is S.

In yet another preferred embodiment of the compound according to formula (I) R is an alkyl, preferably a $C_1$-$C_6$alkyl.

In a preferred embodiment the radioisotope is a $^{11}C$. Thus, in a preferred embodiment of the compound according to formula (I), R is selected from the group consisting of $^{11}CH_3$, $^{11}CCD_3$, $C^3H_3$ and $C_n(H_{2n+1}$ or $D_{2n+1})^{11}CH_2$.

In yet another preferred embodiment of the compound according to formula (I) R is a haloalkyl.

In a preferred embodiment the radioisotope is a $^{18}F$. Thus, in a preferred embodiment of the compound according to formula (I), R is selected from the group consisting of $CH_2^{18}F$, $CD_2^{18}F$, or $C_n(H_{2n}$ or $D_{2n})CH_2^{18}F$.

In yet another preferred embodiment, the $Ar^1$ in the compound according to formula (I) is phenyl and optionally substituted with from 1 to 3 substitutents independently selected from the group consisting of Cl, Br, F, hydroxy, $NH_2$, $NHCH_3$, $OCH_3$, $SCH_3$, CN, $CF_3$ and nitro.

In another preferred embodiment, the $Ar^1$ in the compound according to formula (I) is pyridyl and optionally substituted with from 1 to 3 substitutents independently selected from the group consisting of Cl, Br, F, hydroxy, $NH_2$, $NHCH_3$, $OCH_3$, $SCH_3$, CN, $CF_3$ and nitro.

Further, a preferred compound according to the compound of formula (I) is a compound wherein $Ar^1$ is 4-chlorophenyl.

A preferred compound according to the compound of formula (I) is a compound wherein $Ar^2$ is phenyl.

A preferred compound according to the compound of formula (I) is a compound wherein X is Cl, Br, or F.

A preferred compound according to the compound of formula (I) is a compound wherein $Ar^2$ is phenyl.

A preferred compound according to the compound of formula (I) is a compound wherein n=1. In another preferred compound, n=1, 2, or 3.

Another preferred compound according to the compound of formula (I) is a compound wherein m=1.

Another preferred compound according to the compound of formula (I) is a compound having the formula (IIa)

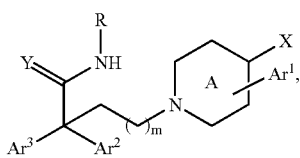

wherein Y, R, X, $Ar^1$, $Ar^2$, $Ar^3$, n and m are as defined above.

Another preferred compound according to the compound of formula (I) is a compound having the formula (IIb)

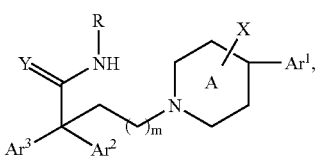

wherein Y, R, X, $Ar^1$, $Ar^2$, $Ar^3$, n and m are as defined above.

Another preferred compound according to the compound of formula (I) is a compound having the formula (IIc)

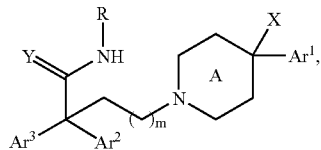

wherein Y, R, X, $Ar^1$, $Ar^2$, $Ar^3$, n and m are as defined above.

B. N-Desmethyl-loperamide (dLop)

N-Desmethyl-loperamide (dLop) is a known metabolite of loperamide (Yoshida et al. 1979, *Biomed Mass Spectrum* 6:253-259). Loperamide is an opiate agonist that is commonly used to treat diarrhea. It acts on opiate receptors in the gut to slow motility and thereby increase removal of water from stool. Loperamide has low pharmacological toxicity and is an avid substrate for P-gp at the blood-brain barrier (Choo et al, 2006, *J Pharmacol Exp Therap* 317:1012-1018; Examples herein). For example, despite high doses and high plasma concentrations in human subjects, loperamide almost completely lacks central nervous system effects, because P-gp efficiently blocks virtually all brain uptake. Loperamide is rapidly metabolized in mammals mainly by the dealkylation of the dimethyl amide moiety (Kalgutkar et al., 2004, *Drug Metab Dispos* 32:943-952; Yoshida et al., 1979, *Biomed Mass Spectrum* 6:253-259). Applicants predicted and showed herein that N-desmethyl-loperamide has adequate lipophilicity to enter brain if not inhibited by P-gp. Further, because N-desmethyl-loperamide (dLop) appears as a metabolite of loperamide, isolated dLop would be safe to administer to human subjects in tracer doses.

dLop (free base) has the following formula (III):

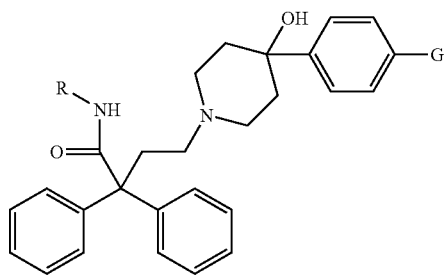

wherein R=$CH_3$ and G=Cl.

A preferred dLop is an isolated dLop, wherein the isolated dLop is substantially free of any dLop metabolites and substantially free of loperamide.

dLop can be used in a variety of methods. In a preferred embodiment of the present invention, dLop is radiolabeled and used as a radiotracer for imaging P-gp function in vitro and in vivo, as further described herein.

In another preferred embodiment of the present invention dLop is used as an anti-diarrheal drug, preferably in human subjects. dLop is similar to loperamide, which is also used as an anti-diarrheal drug, since dLop does not enter the brain and is a high affinity opiate receptor antagonist. Because dLop accumulates in a human body due to metabolism of loperamide into several metabolites, dLop will be safe in human subjects. When used as an anti-diarrheal drug, dLop is not labeled.

C. N-Desmethyl-Loperamide (dLop) is a Substrate for P-gp

P-gp prevents the brain uptake of drugs from several chemical classes and can transport substances while in the lipid bilayer, namely before they actually cross the membrane (Gottesmann et al., 2002, *Nat Rev Cancer* 2:48-58). Substrates for P-gp tend to have both lipophilic components and a positive charge. The lipophilicity causes drugs to be concentrated within the lipid bilayer and thereby exposed to this efflux transporter, which acts as a "hydrophobic vacuum cleaner" (Raviv et al., 1990, *J Biol Chem* 265:3975-3980).

Specifically, it was shown in rodents, monkeys, and humans that the dLop-based compounds of the present invention are avid substrates for P-gp.

Since dLop is a major metabolite of the over-the counter drug Imodium™ (i.e., loperamide), it is safe for administration to human subjects—even at much higher doses than will be given as a radiotracer.

D. N-Desmethyl-loperamide (dLop)-Related Compounds

In a preferred embodiment of the present invention a radiotracer is obtained by incorporating a radiolabel into a structure based on N-desmethyl-loperamide (dLop), referred to herein as a dLop-related compound. A dLop-related compound of the present invention has the following formula (III):

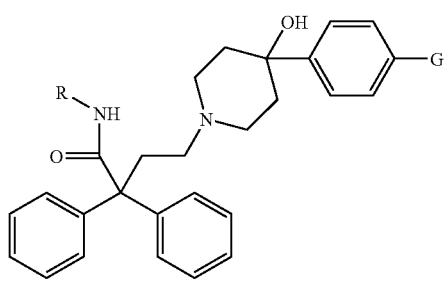

wherein R=$C_1$-$C_6$ alkyl group, preferably a $C_1$-$C_3$ alkyl group or an F-containing $C_1$-$C_6$ alkyl group, preferably an F-containing $C_1$-$C_3$ alkyl group and wherein G can be any halogen. As described herein, in compounds related to the compound according to formula (III), G can be at any position of the three aryl rings.

In another preferred embodiment, G is $R^1$, $OR^1$, $N(R^1)_2$ or a halogen; and $R^1$ is $C_1$-$C_6$ alkyl group, preferably a $C_1$-$C_3$ alkyl group, or an F-containing $C_1$-$C_6$ alkyl group, preferably an F-containing $C_1$-$C_3$ alkyl group.

In yet another embodiment, G can be any other simple substituents on any of the three aryl rings, including, but not limited to, $CH_3$, CN, $OCH_3$, $SCH_3$, $NO_2$, or $N(CH_3)_2$ and halogen.

A preferred dLop-related compound is an isolated dLop-related compound, wherein the isolated dLop-related compound is substantially free of any dLop metabolites and substantially free of loperamide.

E. Radiolabeled dLop and dLop-Related Compounds

The present invention provides radiolabeled dLop and radiolabeled dLop-related compounds wherein a radiolabel in an alkyl group can be attached to the amide nitrogen of dLop. Provided are also pharmaceutically acceptable salts thereof. Further provided are isomers thereof.

1. [$^{11}$C]dLop

A preferred radiolabeled compound of the present invention is [$^{11}$C]dLop having the following formula (IX):

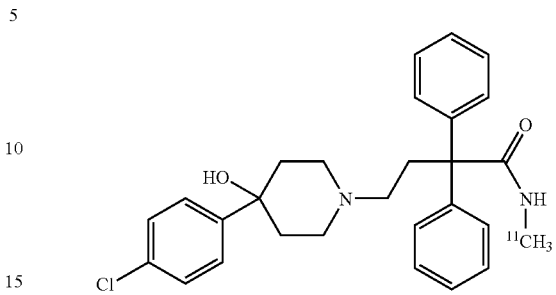

Radiolabeling of dLop in its single N-methyl group mostly avoids troublesome radiometabolites that may enter the brain when P-gp is blocked, absent, or dysfunctional and, thus, allows quantitative measurement of P-gp function. By contrast, radiolabeled loperamide when used as a radiotracer for P-gp function produces many troublesome radiometabolites interfering with quantitative measurement of P-gp function.

A preferred [$^{11}$C]dLop is an isolated [$^{11}$C]dLop. An isolated [$^{11}$C]dLop is substantially free of any [$^{11}$C]dLop metabolites and substantially free of [$^{11}$C]loperamide.

2. [$^{11}$C]dLop is Superior to [$^{11}$C]Loperamide as a Radiotracer

Metabolism of loperamide and N-desmethyl-loperamide occurs predominantly by demethylation (Yoshida et al., 1979, *Biomed Mass Spectrum* 6:253-259). However, while metabolism of [$^{11}$C]loperamide leads to several radiometabolites that would thwart a quantitative analysis of imaging P-gp function by PET, metabolism of [$^{11}$C]dLop leads only to single-carbon radiometabolites, such as [$^{11}$C]methanol. These radiometabolites will be oxidized and ultimately expired as [$^{11}$C] carbon dioxide; they should not accumulate in tissues accessed by the radiotracer to cause difficulty in biomathematical analysis of acquired PET data. Thus, [$^{11}$C]dLop is superior to [$^{11}$C]loperamide as a radiotracer.

3. Radiolabeled dLop-Related Compounds

The present invention provides radiolabeled dLop-related compounds. A radiolabeled dLop-related compound is also within the meaning of a radiotracer as used herein. A preferred radiotracer of the present invention is a compound according to formula (I)

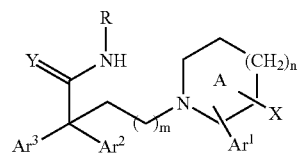

wherein Y is O or S; R is $C_1$-$C_6$ alkyl or $C_1$-$C_6$halo$_6$alkyl, X is selected from the group consisting of hydroxyl and halo; each $Ar^1$ $Ar^2$ and $Ar^3$ is independently aryl or heteroaryl, each of which is optionally substituted with from 1 to 3 substituents, independently selected from the group consisting of halo, hydroxy, amino, $C_1$-$C_6$alkoxy, $C_1$-$C_6$alkylthio, cyano, $C_1$-$C_6$haloalkyl and nitro; n is the integer 0, 1, 2 or 3; and m is the integer 1, 2 or 3, wherein one atom selected from the group consisting of carbon, hydrogen, nitrogen, oxygen and halogen atom comprises or is replaced by a detectable amount of a radioisotope selected from the group consisting of $^{11}$C, $^{13}$N, $^{15}$O, $^{18}$F, $^{76}$Br, and $^{123}$I. The invention also provides and all stereoisomers or pharmaceutically acceptable salts thereof in isolated and purified form. Preferred are the radioisotopes selected from the group consisting of $^{11}$C, $^{3}$H and $^{18}$F. Also preferred are compounds according to formula (I), wherein n=1, 2, or 3, preferably, n=1. Further, a preferred compound according to formula (I) is a compound wherein m=1.

Another preferred compound according to formula (I), is a compound wherein one atom from R comprises or is replaced by a detectable amount of a radioisotope selected from the group consisting of $^{11}$C and $^{3}$H, if $C_1$-$C_6$alkyl, or $^{11}$C, $^{3}$H and $^{18}$F, if $C_1$-$C_6$haloalkyl.

Another preferred compound according to formula (I), is a compound wherein R can also be $C_n(H_{2n+1})$ or $D_{2n+1})^{11}CH_2$ wherein n is the integer 0, 1, 2, 3, 4, 5 or 6. Further, a preferred compound according to formula (I), is a compound wherein R is selected from the group consisting of $^{11}CH_3$, $^{11}CD_3$ and $C^3H_3$ or wherein R is $C_1$-$C_6$haloalkyl.

Also preferred is a compound according to formula (I), wherein R is selected from the group consisting of $C_n(H_{2n}$ or $D_{2n})CH_2^{18}F$ and n is the integer 0, 1, 2, 3, 4, 5 or 6.

Further, this invention provides a compound according to formula (I), wherein R is selected from the group consisting of $CH_2^{18}F$ and $CD_2^{18}F$.

A preferred compound is a compound according to formula (I) wherein $Ar^1$ is phenyl, optionally substituted with from 1 to 3 substitutents independently selected from the group consisting of Cl, Br, F, hydroxy, $NH_2$, $NHCH_3$, $OCH_3$, $SCH_3$, CN, $CF_3$ and nitro.

Further, a preferred compound according to formula (I) wherein $Ar^1$ is pyridyl, optionally substituted with from 1 to 3 substitutents independently selected from the group consisting of Cl, Br, F, hydroxy, $NH_2$, $NHCH_3$, $OCH_3$, $SCH_3$, CN, $CF_3$ and nitro.

Another preferred compound according to formula (I) is a compound wherein $Ar^1$ is 4-chlorophenyl. Other preferred compounds according to formula (I) are compounds wherein either $Ar^2$ or $Ar^3$ are phenyl.

In some compounds according to formula (I), X is selected from the group consisting of hydroxy, Cl, Br and F.

Another preferred radiotracer of the present invention is a compound having the formula (IIa):

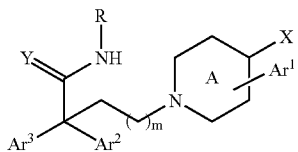

and all stereoisomers or pharmaceutically acceptable salts thereof, wherein Y, R, X, $Ar^1$, $Ar^2$, $Ar^3$, n and m are as defined above.

Another preferred radiotracer of the present invention is a compound having the formula (IIb):

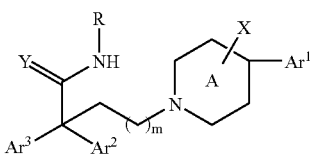

and all stereoisomers or pharmaceutically acceptable salts thereof, wherein Y, R, X, $Ar^1$, $Ar^2$, $Ar^3$, n and m are as defined above.

Another preferred radiotracer of the present invention is a compound having the formula (IIc):

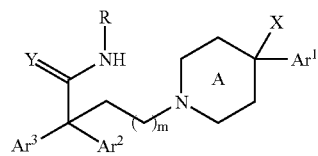

and all stereoisomers or pharmaceutically acceptable salts thereof, wherein Y, R, X, $Ar^1$, $Ar^2$, $Ar^3$, n and m are as defined above.

4. [$^{11}$C]dLop-Related Compounds

The present invention also provides [$^{11}$C]dLop-related compounds. A preferred [$^{11}$C]dLop-related compound is one having formula (III):

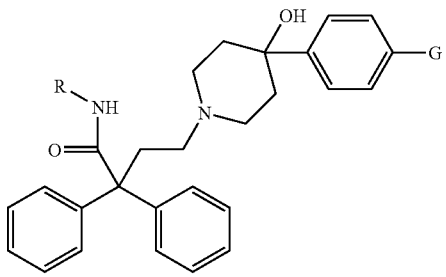

wherein R is a $C_1$-$C_6$ alkyl group wherein one C is $^{11}$C and wherein G is $R^1$, $OR^1$, $N(R^1)_2$, CN, $NO_2$, $SR^1$, or a halogen; and $R^1$ is $C_1$-$C_6$ alkyl. As described herein, in compounds related to the compound according to formula (III), G can be at any position of the three aryl rings.

Another preferred [$^{11}$C]dLop-related compound is one having formula (III):

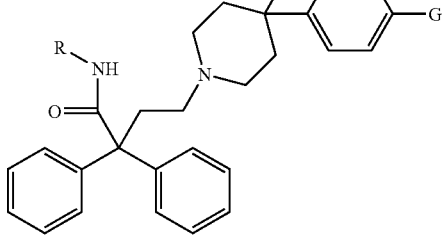

wherein R is a $C_1$-$C_6$ alkyl group wherein one C is $^{11}$C and wherein G is $R^1$, $OR^1$, $N(R^1)_2$, CN, $NO_2$, $SR^1$, or a halogen; and $R^1$ is $C_1$-$C_6$ alkyl. As described herein, in compounds related to the compound according to formula (III), G can be at any position of the three aryl rings.

Another preferred [¹¹C]dLop-related compound is one having formula (III):

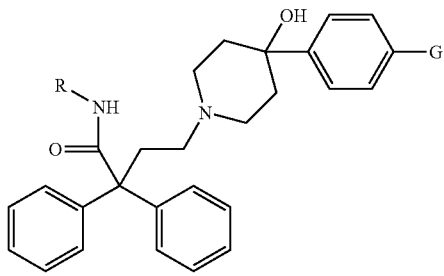

wherein R is a $C_1$-$C_3$ alkyl group wherein one C is $^{11}C$ and wherein G is $R^1$, $OR^1$, $N(R^1)_2$, CN, $NO_2$, $SR^1$, or a halogen; and $R^1$ is $C_1$-$C_6$ alkyl. As described herein, in compounds related to the compound according to formula (III), G can be at any position of the three aryl rings.

Another preferred [¹¹C]dLop-related compound is one having formula (III):

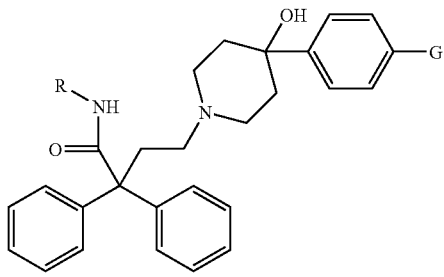

wherein R is a $C_1$-$C_3$ alkyl group wherein one C is $^{11}C$ and wherein G is $R^1$, $OR^1$, $N(R^1)_2$, CN, $NO_2$, $SR^1$, or a halogen; and $R^1$ is $C_1$-$C_6$ alkyl. As described herein, in compounds related to the compound according to formula (III), G can be at any position of the three aryl rings.

A preferred [¹¹C]dLop-related compound is one having formula (III):

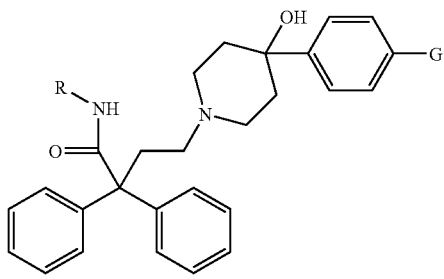

wherein R is a $C_1$-$C_6$ alkyl group wherein one C is $^{11}C$ and wherein, as described herein, G can be at any position of the three aryl rings.

Another preferred [¹¹C]dLop-related compound is one having formula (III):

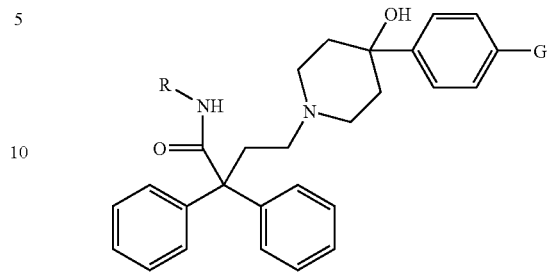

wherein R is a $C_1$-$C_6$ alkyl group wherein one C is $^{11}C$ and wherein G is any halogen at any position on any of the three aryl rings.

Another preferred [¹¹C]dLop-related compound is one having formula (III):

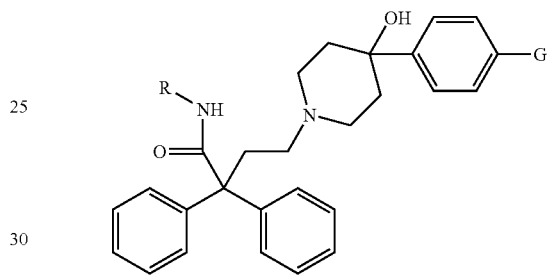

wherein R is a $C_1$-$C_3$ alkyl group wherein one C is $^{11}C$ and wherein G is any halogen at any position on any of the three aryl rings.

Another preferred [¹¹C]dLop-related compound is one having formula (III):

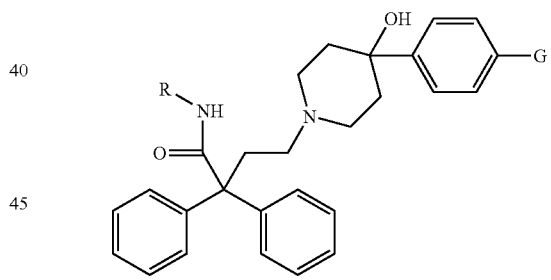

wherein R is a $C_1$-$C_3$ alkyl group wherein one C is $^{11}C$ and wherein, as described herein, G can be at any position of the three aryl rings.

Another preferred [¹¹C]dLop-related compound is one having formula (III).

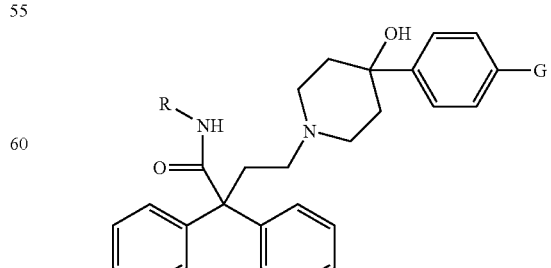

wherein R is $^{11}CH_3$ or R is $C_1$-$C_6$alkyl wherein one C is $^{11}C$ or R is substituted with a radiolabeled halogen atom, G is $R^1$, $OR^1$, $N(R^1)_2$, CN, $NO_2$, $SR^1$, or a halogen, and $R^1$ is $C_1$-$C_6$ alkyl. Stereoisomers or pharmaceutically acceptable salts thereof are also provided. A preferred [$^{11}C$]dLop-related compound is one wherein R is $^{11}CH_3$.

A preferred [$^{11}C$]dLop-related compound is an isolated [$^{11}C$]dLop-related compound. An isolated [$^{11}C$]dLop-related compound is substantially free of any [$^{11}C$]dLop metabolites and substantially free of [$^{11}C$]loperamide.

5. [$^{18}F$]dLop

The present invention further provides $^{18}F$-labeled radiotracers. A preferred $^{18}F$-labeled radiotracer of the present invention is [$^{18}F$]dLop having the following formula (X):

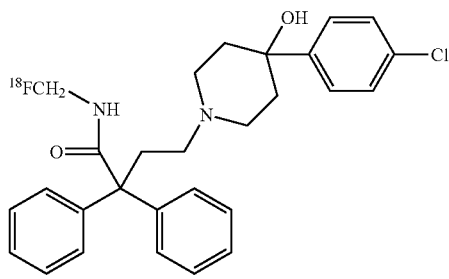

[$^{18}F$]dLop is a fluorine-18 labeled analogue of dLop, wherein the fluorine-18 is contained in the single N-methyl group.

A preferred [$^{18}F$]dLop is an isolated [$^{18}F$]dLop. An isolated [$^{18}F$]dLop is substantially free of any [$^{18}F$]dLop metabolites.

6. [$^{18}F$]dLop-Related Compounds

Another preferred radiolabeled compound of the present invention is an [$^{18}F$]dLop-related compound having the following formula (III):

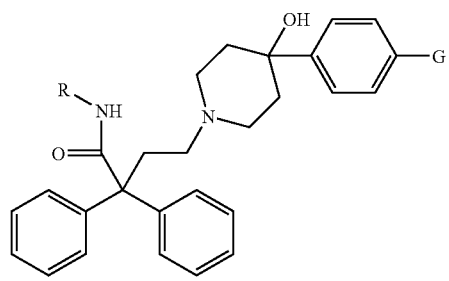

wherein R is $^{18}FH_2C$ or R is $C_1$-$C_6$ alkyl wherein one C is substituted by $^{18}F$ or R is substituted with a radiolabeled halogen atom; G is $R^1$, $OR^1$, $N(R^1)_2$, CN, $NO_2$, $SR^1$, or a halogen; and $R^1$ is $C_1$-$C_6$ alkyl. As described herein, G can be at any position of the three aryl rings.

Another preferred [$^{18}F$]dLop-related compound is one having formula (III).

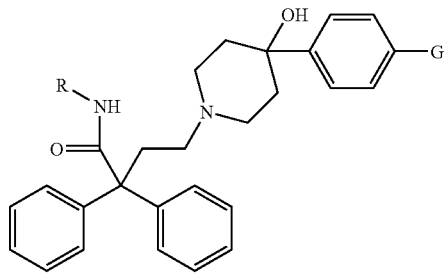

wherein R is $^{18}FH_2C$ or R is $C_1$-$C_6$alkyl wherein one C is substituted with $^{18}F$, G is $R^1$, $OR^1$, $N(R^1)_2$, CN, $NO_2$, $SR^1$, or a halogen, and $R^1$ is $C_1$-$C_6$ alkyl. Stereoisomers or pharmaceutically acceptable salts thereof are also provided. A preferred [$^{18}F$]dLop-related compound is one wherein R is $^{18}FH_2C$.

In a preferred embodiment of the present invention an [$^{18}F$]dLop-related compound has the following formula (XI):

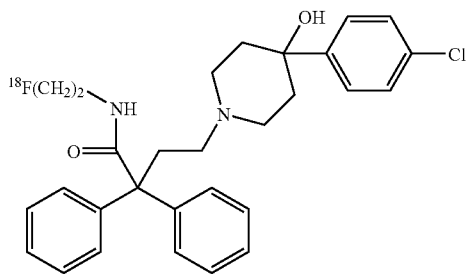

In another preferred embodiment of the present invention an [$^{18}F$]dLop-related compound has the following formula (XII):

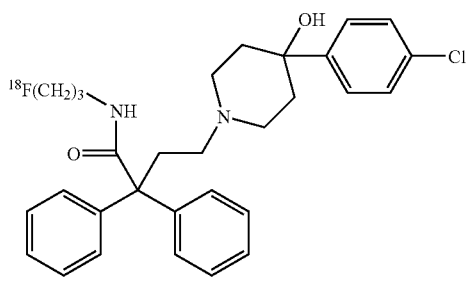

A preferred [$^{18}F$]dLop-related compound is an isolated [$^{18}F$]dLop-related compound. An isolated [$^{18}F$]dLop-related compound is substantially free of any [$^{18}F$]dLop metabolites.

7. Other Labeled dLop-Related Compounds

Other preferred labeled dLop-related compounds have the following formula (III):

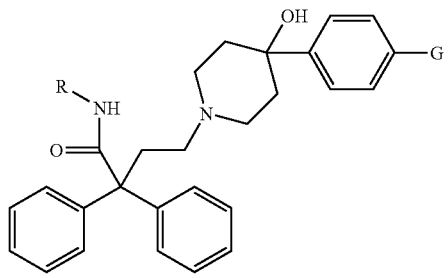

wherein R is a $C_1$-$C_6$ alkyl group wherein one C is substituted with a radioactive atom and wherein G is $R^1$, $OR^1$, $N(R^1)_2$ or a halogen; and $R^1$ is $C_1$-$C_6$ alkyl group, preferably a $C_1$-$C_3$ alkyl group. G can be at any position on any of the three aryl rings.

Other preferred labeled dLop-related compounds have the following formula (III):

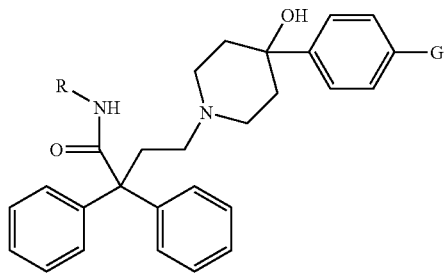

wherein R is a $C_1$-$C_3$ alkyl group wherein one C is substituted with a radioactive atom and wherein G is $R^1$, $OR^1$, $N(R^1)_2$ or a halogen; and $R^1$ is $C_1$-$C_6$ alkyl group, preferably a $C_1$-$C_3$ alkyl group. G can be at any position on any of the three aryl rings.

Preferred radioactive atoms for these dLop-related radiotracers are $^{15}O$, $^{13}N$, $^{99m}Tc$, $^{94m}Tc$, $^{123}I$, $^{125}I$, $^{76}Br$, and $^{77}Br$. $^{123}I$, $^{125}I$, $^{76}Br$, and $^{77}Br$ are more preferred radioactive atoms. The choice of radioactive atom to be incorporated into the compound having formula (III) will depend on the specific analytical, diagnostic, clinical research, or pharmaceutical application.

In addition, the salts, hydrates, solvates, isomers and prodrugs of the compounds of the present invention are also contemplated.

F. Synthesis of Radiolabeled dLop-Related Compounds, [$^{11}C$]dLop and [$^{11}C$]dLop-Related Compounds The present invention provides methods for producing radio-labeled dLop-related compounds, [$^{11}C$]dLop and [$^{11}C$]dLop-related compounds.

The invention provides methods of producing a compound according to formula (I). In a preferred embodiment, this method comprises the steps of: (a) reacting a compound having the formula (IV)

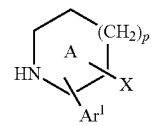

with a compound having the formula (V):

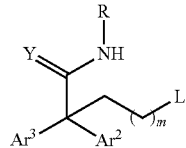

to form a product, (b) hydrolyzing the product from step (a), and (c) N-alkylating the product from step (b) to provide an N-alkyl group R, wherein L is a leaving group, R is $C_1$-$C_6$alkyl or $C_1$-$C_6$haloalkyl, and wherein carbon or halogen atom comprises a detectable amount of a radioisotope. Step (c) can be performed in the presence of [$^{11}C$]iodomethane or in the presence of [$^{11}C$]methyl triflate, or another $^{11}C$-alkylating agent. Preferably, L is a halogen. Preferably, p=1, 2, or 3.

Also provided herein are methods of producing a compound according to formula (III). In a preferred embodiment of the present invention, the method of producing a compound according to formula (III) comprises the steps of (a) reacting a compound having the formula (VI)

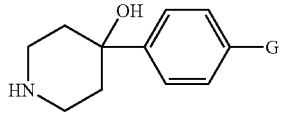

with a compound having the formula (VII):

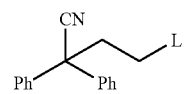

to form a product, (b) hydrolyzing the product from step (a), (c) N-alkylating the product from step (b) to provide an N-alkyl group R, wherein L is a leaving group, R is $C_1$-$C_6$alkyl or $C_1$-$C_6$haloalkyl, and wherein one carbon or halogen atom comprises a detectable amount of a radioisotope. Preferably, R is $^{11}CH_3$. Preferably, L is a halogen. Step (c) can be performed in the presence of [$^{11}C$]iodomethane or in the presence of [$^{11}C$]methyl triflate, or another $^{11}C$-alkylating agent.

In a preferred embodiment the method for producing [$^{11}C$]dLop or a [$^{11}C$]dLop-related compound comprises the following steps: (a) reacting a compound having the formula (VI):

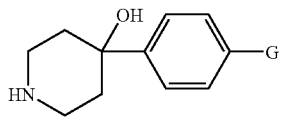

with a compound having the formula (VIII):

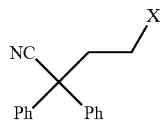

to form a coupled product in which X has been displaced by N, (b) hydrolyzing the nitrile product to amide; and (c) N-alkylating the hydrolyzed product to provide an N-alkyl group selected from $^{11}CH_3$ and R, wherein X is a leaving group and wherein R is $C_1$-$C_3$ alkyl and at least one C of the $C_1$-$C_3$ alkyl is $^{11}C$ or R is substituted with a radiolabeled atom.

In a preferred embodiment of this method, atom X in compound (VIII) is a halogen. In another preferred embodiment, atom X is another leaving group known in the art, such as OMes, OTf, or OTs.

In another preferred embodiment of this method, compound (VIII) is 4-(4-chlorophenyl)-4-hydroxylpiperidine. Exemplary compounds (VI) useful for the syntheses described herein are 4-bromo-2,2-diphenylbutyronitrile, 4-chloro-2,2-diphenylbutyronitrile, or 4-iodo-2,2-diphenyl-butyronitrile.

In a preferred embodiment, the N-alkylating of the hydrolyzed p4roduct (step c) is performed in the presence of $[^{11}C]$ iodomethane or alternatively $[^{11}C]$methyl triflate, or a related $^{11}C$-methylation agent.

A detailed protocol for the synthesis of $[^{11}C]$dLop and $[^{11}C]$dLop-related compounds is provided in Example 9.

One of skill in the art would appreciate that the conditions of the labeling reaction may be varied with respect to amount of precursor amide, solvent, base, temperature and time. For example, the reaction may be promoted thermally or by microwaves. The reaction may be performed in conventional automated radiosynthetic devices or in microfluidic devices.

G. Synthesis of $[^{18}F]$dLop and $[^{18}F]$dLop-Related Compounds

The longer half-life of fluorine-18 (110 min) compared to that of carbon-11 (20 min) permits production of high activities of $[^{18}F]$dLop and $[^{18}F]$dLop-related compounds from cyclotron-produced $[^{18}F]$fluoride ion commercially for widespread distribution and application at satellite clinical PET Centers. $^{18}F$-labeled radiotracers, other than those described herein, have been used commercially, including $[^{18}F]$fluoride ion and $[^{18}F]$FDG (e.g., see, web site PETNET Solutions).

The present invention provides methods for producing $[^{18}F]$dLop and $[^{18}F]$dLop-related compounds. In a preferred embodiment the method for producing $[^{18}F]$dLop or a $[^{18}F]$dLop-related compound comprises the N-alkylation of a precursor amide under basic conditions with an $^{18}F$-containing reagent, such as $^{18}F$-labeled fluoromethyl iodide, bromide or tosylate, or 2-fluoroethyl bromide, iodide or tosylate, which are already described herein as labeling agents that may be produced from $[^{18}F]$fluoride ion. As known in the art, such reactions may be promoted thermally in a variety of solvents and also by microwaves. They may be performed in conventional automated radiosynthesis devices or in microfluidic devices.

In a preferred embodiment of the present invention, the following scheme is used to synthesize $[^{18}F]$dLop or an $[^{18}F]$dLop-related compound:

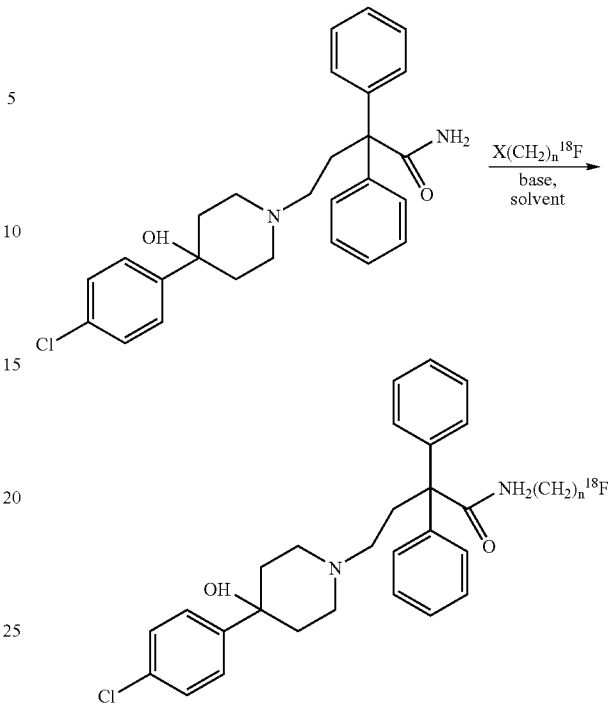

wherein n may be 1-3, X may be Cl, Br, I, OTs or OTf.

Compounds of the present invention may be isolated and purified, e.g., by high performance liquid chromatography (HPLC) or reverse phase HPLC (see, Examples). Any remaining organic solvents may be removed by any conventional means known in the art (e.g., in vacuo evaporation). One of skill in the art will recognize that additional methods exist for the preparation of the compounds and radiotracers of the present invention, for example by direct nucleophilic substitution of a leaving group (X) from the N-alkyl chain in an unprotected or protected precursor with $[^{18}F]$fluoride ion, where X=halogen or other suitable leaving group, such as tosylate, triflate or mesylate. Where the precursor is protected, the labeling step is followed by a deprotection step. Protecting groups and deprotection methods are well known to those skilled in the art.

In another aspect, the present invention provides a composition comprising a radiolabeled compound which is at least 75% purified, at least 80% purified, at least 85% purified, at least 90% purified, at least 91% purified, at least 92% purified, at least 93% purified, at least 94% purified, at least 95% purified, at least 96% purified, at least 97% purified, at least 98% purified, or at least 99% purified. A most preferred radiolabeled compound of the invention is at least 99% purified.

III. Methods

The present invention also provides methods of using the compounds of the invention. Numerous utilities for the radiotracers of the present invention are set forth herein. For example, the radiotracers can be used to (i) measure an interaction of a P-gp with the radiotracer, (ii) visualize a change in P-gp function in a mammal, (iii) measure an interaction of a test compound with a P-gp, (iv) perform P-gp imaging, including diagnostic imaging in a mammal, (v) perform diagnostic imaging of P-gp function in a biological sample, such as a cell or tissue, (vi) assess P-gp function in subjects having neurological conditions; (vii) assess multidrug resistance in subjects with cancer, (viii) detect or quantify a P-gp function, etc. Methods of the present invention can be practiced in vitro and in vivo.

A. Measuring an Interaction of P-Glycoprotein with a Radiotracer

1. Binding Assays

Several P-gp binding assays which also find use in the present invention, are described in WO2005/080992, which is hereby incorporated by reference in its entirety. For example, the human colon carcinoma cell line (Caco-2) transport assay (Anderle et al., 1998, *J Pharm Sci* 87:757-762; Gao et al., 2001, *Pharm Res* 18:171-176) which is the original screen for P-gp, is still widely used in industry because it provides a reliable and functional measure of how P-gp affects the permeability of a drug. However, the assay is limited by cost and throughput, culturing on filter supports and the need for LC-MS analysis of the transported compounds being required which is both time-consuming and expensive.

Doppenschmitt et al. (1998, *Pharm Res* 15:1001-1006; 1999, *J Pharmacol Exp Ther,* 288:348-35) have reported the use of a radioligand binding assay to characterize P-gp binding properties. Binding studies were performed on human Caco-2 cells to demonstrate that non-labeled substrates could be used to displace [$^3$H]verapamil or [$^3$H]vinblastine. However, while it was suggested that this assay could form the basis for a high-throughput screening tool, no studies were performed to translate these basic experiments into a robust screen. Furthermore, the non-homogeneous experimental procedures described in these papers were time-consuming and labor-intensive, requiring filtration to quantify binding.

Schinkel et al. (1996, *J Clin Invest* 97(11):2517-24) determined that loperamide was a transport substrate for the mouse mdr1a P-gp and its human homologue MDR1 and consequently did not pass the blood-brain barrier efficiently. Examples 3 and 11 herein provide assays useful for determining the binding and interaction of labeled and unlabeled loperamide, dLop, and dLop-related compounds to a variety of receptors and transporters, including, but not limited to, 5-HT$_{1A,1B,1D,1E,2A-C,3,5A,6,7}$, $\alpha_{1A,2A-2C}$, $\beta_{1,2}$, µ-, κ-, δ-opiate, D$_{1-5}$, H$_{1-3}$, M$_{1-5}$, $\sigma_{1,2}$, NET, SERT and DAT.

2. Measuring an Interaction of a Radiotracer with a P-Glycoprotein

The present invention provides methods for measuring an interaction of a compound of the present invention, in particular, radiolabeled compound, such as a radiotracer, with a P-gp. In one embodiment, the method for measuring an interaction of a radiolabeled compound with a P-gp comprises the steps of (a) contacting a P-gp with a radiolabeled compound to produce a P-gp-radiolabeled compound complex; and (b) measuring an interaction of the radiolabeled compound with the P-gp. A measurable signal is indicative of the amount of the radiolabeled compound interacting with the P-gp. The radiolabeled compound may be any radiotracer described herein, preferably a radiotracer selected from the group consisting of a compound having the formula (I), a compound having the formula (IIa), a compound having the formula (IIb), a compound having the formula (IIc), and compound having the formula (III).

The P-gp is contacted with a radiolabeled compound using an effective amount of the radiolabeled compound to achieve the desired effect.

The P-gp may be a P-gp in a mammal, a P-gp in a cell, preferably a mammalian cell, a P-gp in a P-gp preparation, or an isolated P-gp, preferably a recombinant P-gp.

The measurable signal may be recorded in, e.g., an electronic or optical database.

B. Measuring an Interaction of a Test Compound with P-gp In Vitro and In Vivo

1. Measuring Binding of a Test Compound to a P-gp

In another aspect of the present invention, a method for measuring an interaction of a test compound with a P-gp is provided. In a preferred embodiment of the present invention this method comprises the steps of (a) contacting a P-gp preparation with a radiolabeled compound, e.g. a radiotracer as described herein, to produce a P-gp-radiolabeled compound complex, (b) measuring an interaction of the radiolabeled compound with the P-glycoprotein; wherein a first measurable signal is obtained, (c) contacting the P-gp-radiolabeled compound complex with a test compound under conditions whereby the interaction of the radiolabeled compound with the P-gp is prevented by the test compound, and (d) detecting a second measurable signal. A higher second measurable signal when compared to the first measurable signal is indicative of the test compound interacting with the P-gp. A second measurable signal which is substantially the same as the first measurable signal is indicative that the test compound does not interact with the P-gp. The radiolabeled compound may be any radiolabeled compound described herein, preferably, a radiotracer selected from the group consisting of a compound having the formula (I), a compound having the formula (IIa), a compound having the formula (IIb), a compound having the formula (IIc), and compound having the formula (III).

The P-gp preparation is contacted with a radiolabeled compound using an effective amount of the radiolabeled compound to achieve the desired effect.

In another preferred embodiment of the present invention, the method for measuring an interaction of a test compound with a P-gp comprises the steps of (a) contacting a P-gp preparation with a mixture comprising (i) a radiolabeled compound, such as a radiotracer, and (ii) a test compound to produce a P-gp-radiolabeled compound complex and a P-gp-test compound complex, (b) measuring the interaction of the radiolabeled compound with the P-gp; wherein a first measurable signal is obtained, and (c) comparing the first measurable signal to a second measurable signal obtained by contacting the P-gp with the radiolabeled compound in the absence of the test compound. A lower first measurable signal when compared to the second measurable signal is indicative of the test compound interacting with the P-gp.

The first and second measurable signals may be recorded in, e.g., an electronic or optical database.

2. P-gp Preparation

Various P-gp preparations are useful in the above methods. In some embodiments, the P-gp preparation is a membrane preparation. Alternatively, the P-gp preparation is a whole cell preparation.

The P-gp preparation may be a mammalian cell expressing P-gp. For example the porcine kidney-derived cell line, LLC-PK1 (American Type Culture collection, Manassas, Va.; A.T.C.C. CL-101) expresses human P-gp. Other cells, in particular human cancer cell lines may be used in the methods of the present invention. Expression of P-gp can be confirmed by detecting the P-gp polypeptide and/or detecting P-gp mRNA using methods known in the art (e.g., Western blotting, immunoassays, Northern blotting and PCR; e.g., see Sambrook, Fritsch, and Maniatis, "*Molecular Cloning A Laboratory Manual,*" published by Cold Spring Harbor Laboratory Press, 2nd edition, 1989; Inis et al. (1990) *PCR Protocols, A Guide to Methods and Applications*, Academic Press, Inc. N.Y)).

In another embodiment, the P-gp preparation comprises an isolated P-gp, preferably a recombinantly produced P-gp. Nucleotide sequences and protein sequences for making recombinant P-gp are known in the art and are available, e.g., from GenBank. Further, methods for making and purifying recombinant proteins are known in the art.

In some embodiments the P-gp preparation is immobilized to a solid support or supports. A preferred support or supports is a collection of beads or particles. The solid support or supports can be selected from the group consisting of discrete particles (spherical or irregular), beads, fibers, filters, membranes, nanoparticles, and monoliths.

3. Test Compounds

Suitably, the test compound is a chemical compound. For example, the test compound may be a naturally occurring compound, such as a peptide or a nucleic acid. Typically, the test compound will be a drug or drug candidate. In general, drugs or drug candidates are low molecular weight organic compounds which have been specifically synthesized or optimized to evaluate their biological efficacy in a drug discovery/evaluation program. The test compound may also be an organic toxin, or a candidate for radiolabeling and development as an imaging agent.

A preferred test compound is a compound which is a suspected inhibitor of P-gp function.

Another preferred test compound is a compound which is a suspected substrate of P-gp.

In a preferred embodiment, a test compound is a radiotracer other than a radiolabeled dLop which may be evaluated for use as a radiotracer. In a preferred embodiment, P-gp functionality is determined in the presence of this radiotracer and a P-gp inhibitor, such as DCPQ or tariquidar.

C. Assessment of Multidrug Resistance in a Cancer Cell

In yet another aspect of the present invention, a method of assessing multidrug resistance in a cancer cell, is provided. In a preferred embodiment of the present invention, this method comprises the steps of (a) contacting a cancer cell with a radiolabeled compound, e.g., a radiotracer as described herein, and (b) assessing cellular uptake of the radiolabeled compound. A first measurable signal is obtained which is indicative of the extent of cellular uptake of the radiolabeled compound.

The cancer cell is contacted with a radiolabeled compound using an effective amount of the radiolabeled compound to achieve the desired effect.

In another embodiment of the present invention, a test compound is used to contact the cancer cell in addition to the radiolabeled compound. Contacting the cancer cell with the test compound can be done simultaneously with the radiolabeled compound or before or after the contacting with the radiolabeled compound. Upon contacting the cancer cell with the test compound a second measurable signal is obtained which can be compared to the first measurable signal. A higher second measurable signal is indicative that the test compound is an inhibitor or competitive substrate of P-gp function. The radiolabeled compound may be any radiolabeled compound described herein, preferably, a radiotracer selected from the group consisting of a compound having the formula (I), a compound having the formula (IIa), a compound having the formula (IIb), a compound having the formula (IIc), and compound having the formula (III).

A cell or cancer cell useful in the methods of the present invention is selected from the group consisting of colon cancer, melanoma, mesothelioma, lung cancer, renal cell carcinoma, breast cancer, prostate cancer, sarcoma, ovarian cancer, esophageal cancer, gastric cancer, hepatocellular cancer, nasopharyngeal cancer, pancreatic cancer, and glioma cell.

D. Imaging P-gp Function In Vivo

There is great interest and a need to image P-gp function in vivo. For example, P-gp may unpredictably restrict the brain entry of drugs that are in development for neuropsychchiatric disorders. A P-gp radiotracer would be useful to assess which developmental drug is a P-gp substrate or inhibitor in vivo. Further, a P-gp radiotracer would be useful for investigating how P-gp function may be compromised in various neuropsychiatric conditions. For example, compromised P-gp function may play a role in the unfolding of Alzheimer's disease. In addition, multidrug resistance is responsible for a high proportion of failure in chemotherapeutic treatment of cancer patients. Here, a P-gp radiotracer would be useful for detecting and assessing multidrug resistance in individual cancer patients in vivo (or in cells and tissue specimen obtained from such cancer patients) and for devising and directing more effective drug therapies. Thus, PET radiotracer to measure the function of P-gp may be useful, since several human disorders have been associated with abnormal function of this efflux transporter (see herein).

Hence, elucidation of the expression and function of P gp in human subjects in vivo could be of great importance in both drug development and medicine. Moreover, in the field of developing molecular imaging agents for use with positron emission tomography (PET) or single photon emission computed tomography (SPECT), the effect of P-gp is also frequently encountered, for example, in limiting the brain entry of some neuroreceptor radioligands (Liow et al., 2007, *Synapse* 96:96-105; Elsinga et al., 2005, *Mol Imaging Biol* 7:37-44). These same imaging modalities, with radiotracers based on P-gp substrates, have been proposed for examining P-gp function in vivo (for a review, see Elsinga et al., 2004, *Curr Pharm Design* 10: 1493-1503).

Methods of the present invention can be practiced in vivo, preferably in mammals. A preferred mammal is a monkey. A more preferred mammal is a human.

1. Assessment of P-Glycoprotein Function in Subjects Having Neurological Conditions In neurology, P-gp may, for example, be an obstacle to the brain penetration of anti-HIV drugs (Kim et al., 1998, *J Clin Invest* 101:289-94). Excessive function of P-gp may also be responsible for some cases of resistance to anti-epileptic medications, in this case by blocking passage of the medication across the blood-brain barrier (Siddiqui et al., 2003, *New Engl J Med* 348:1442-1448).

Further, decreased function of P-gp at the blood-brain barrier may decrease clearance of amyloid from brain to plasma and thereby predispose individuals to Alzheimer's disease (Vogelgesang et al., 2002, *Pharmacogenetics* 12:535-541). Thus, altered expression of P-gp may contribute to the progression of neurodegenerative disorders, such as Alzheimer's disease (Lam et al, 2001, *J Neurochem* 76:1121-1128; Cirrito et al., 2005, *J Clin Invest* 115:3285-3290; Vogelgesang et al., 2002, *Pharmacogenetics* 12:535-541), HIV encephalitis (Langford et al., 2004, *J Neuropath Exp Neurology* 63:1038-1046) and Parkinson's disease (Kortekaas et al., 2005, *Ann Neurol* 57:176-179).

In one aspect, the present invention provides a method of assessing P-gp function in a subject having a neurological condition. In a preferred embodiment of the present invention, this method comprises the steps of (a) administering a radiolabeled compound, e.g., a radiotracer as described herein, to the subject, and (b) measuring transport of the radiolabeled compound across the blood-brain barrier. The radiolabeled compound may be any of the radiolabeled compounds described herein, preferably, a radiotracer selected from the group consisting of a compound having the formula (I), a compound having the formula (IIa), a compound having the formula (IIb), a compound having the formula (IIc), and compound having the formula (III).

The radiolabeled compound is administered to the subject in an effective amount of the radiolabeled compound to achieve the desired effect.

The present invention provides radiotracers useful for the assessment of P-gp function in a subject having Alzheimer's disease, Parkinson's disease, dementia, epilepsy, stroke, brain tumor, or Acquired Immuno Deficiency Syndrome (AIDS), i.e., in a subject infected with the Human Immunodeficiency Virus-1 (HIV-1).

2. Assessment of Multidrug Resistance in Subjects with Cancer

P-gp is often highly expressed in tumors (Cordon-Cardo et al., 1990, *J Histochem Cytochem* 9:1277-1287). Overexpression of P-gp is partly responsible for multidrug resistance in some cancers, since P-gp blocks the entry of selective chemotherapies into the cytoplasm of the tumor (Gottesman et al., 2002, *Nat Rev Cancer* 2:48-58). Hence, P-gp can be a severe obstacle to the penetration of established or developmental drugs into the targeted organ or tumor (Schinkel et al., 1996, *J Clin Invest* 97:2517-2524). The present invention provides radiotracers useful for the assessment of multidrug resistance in a subject, preferably in a subject having cancer.

Reduced intracellular levels of anti-tumor agents in a tumor suppresses chemotherapeutic efficacy. Tumors having elevated levels of a multiple drug transporter, such as P-gp, require therapeutic doses of cancer suppressants far in excess of tumors exhibiting lower levels of drug transporters. Typical drugs that are affected by the multidrug resistance include ondasetron, dexamethasone, domperidone, loperamide, doxorubicin, neifinavir, indinevir, sugguinavir, erythromycin, digoxin, vinblastine, paclitaxel, invermectin, cyclosporin, vincristine, colchicines, actinomycin D, and others. Agents that inhibit the active efflux of anti-tumor agents by the drug transporter or agents that potentiate the efficacy of chemotherapeutic agents would enhance the activity of various anti-tumor agents on tumor cells. Known inhibitors of P-glycoprotein include ketoconazole, verapamil, quinidine, cyclosporin, digoxin, erythromycin and loperamide. Inhibition of P-gp function in P-gp-mediated multidrug resistance has been shown to lead to a net accumulation of anti-cancer agent in the cells. For example, verapamil a known calcium channel blocker was shown to sensitize MDR cells to vinca alkaloids in vitro and in vivo.

The ability of a drug transporter proteins, such as P-gp to actively transport therapeutic substances from cells, including both tumor and host cells, has impeded the development of therapies for a wide variety of disorders and conditions in multicellular hosts, particularly in humans. Thus, a continuing need exists for methods to increase the ability of clinicians to administer bioactive substances across biological membranes.

Interaction with a transporter, such as P-gp, can be studied using a variety of assays, including, but not limited to direct assays of drug transport in polarized cell systems and/or with indirect assays such as drug-stimulated ATPase activity or inhibition of the transport of fluorescent substrates.

The present invention provides a method of assessing multidrug resistance in a subject. In a preferred embodiment of the present invention, this method comprises the steps of (a) administering a radiolabeled compound, e.g., a radiotracer as described herein, to a subject and (b) assessing transport of the radiolabeled compound across a tumor.

In another aspect of the present invention, a method of assessing treatment for a subject with multidrug resistance is provided. In a preferred embodiment of the present invention, this method comprises the steps of (a) administering a radiolabeled compound, e.g., a radiotracer as described herein and a P-glycoprotein inhibitor to a subject and (b) determining transport of the compound across the blood brain barrier. The radiolabeled compound may be any of the radiolabeled compounds described herein, preferably, a radiotracer selected from the group consisting of a compound having the formula (I), a compound having the formula (IIa), a compound having the formula (IIb), a compound having the formula (IIc), and compound having the formula (III).

The radiolabeled compound is administered to the subject in an effective amount of the radiolabeled compound to achieve the desired effect.

Preferably, the subject is a human having cancer.

3. Positron Emission Tomography (PET)

A preferred method for imaging P-gp function in vivo and which can be used for methods described herein is Positron emission tomography (PET). PET is a nuclear medicine imaging technique which produces sequential three-dimensional image or map of functional processes in the body. The system detects pairs of gamma rays emitted indirectly by a positron-emitting radioisotope, which is introduced into the body on a biochemical or drug-like molecule. Images of radiotracer distribution in space are then reconstructed by computer analysis, often in modern scanners aided by results from a CT X-ray scan performed on the patient at the same time, in the same machine. The radiotracer, according to its design and distribution reports on some particular aspect of biochemistry or physiology e.g., receptor distribution, transporter distribution, blood flow, protein synthesis, glucose utilization.

To conduct the scan, typically, a short-lived radioisotope, which decays by emitting a positron, which also has been chemically incorporated into the radiotracer, is injected into the living subject (usually into blood circulation), placed in an imaging scanner. There is a waiting period while the radiotracer becomes concentrated in a tissue of interest.

As the radioisotope undergoes positron emission decay (also known as positive beta decay), it emits a positron, the antimatter counterpart of an electron. After traveling up to a few millimeters the positron encounters and annihilates with an electron, producing a pair of annihilation (gamma) photons moving in opposite directions. These are each detected when they reach a scintillator material in the scanning device, creating a burst of light which is detected by photomultiplier tubes or silicon avalanche photodiodes (Si APD). The technique depends on simultaneous or coincident detection of the pair of photons; photons which do not arrive in pairs (i.e., within a few nanoseconds) are ignored.

The most significant fraction of electron-positron decays result in two 511 keV gamma photons being emitted at almost 180 degrees to each other; hence it is possible to localize their source along a straight line of coincidence (also called formally the line of response or LOR). In practice the LOR has a finite width as the emitted photons are not exactly 180 degrees apart. If the recovery time of detectors is in the picosecond range rather than the 10's of nanosecond range, it is possible to calculate the single point on the LOR at which an annihilation event originated, by measuring the "time of flight" of the two photons. This technology is not yet common, but it is available on some new systems.

Radionuclides used in PET scanning are typically isotopes with short half-lives such as $^{11}$C (~20 min), $^{13}$N (~10 min), $^{15}$O (~2 min), and $^{18}$F (~110 min). These radionuclides are incorporated either into compounds or analogs of compounds normally used by the body such as glucose (or glucose analogues), water or ammonia, or into molecules that bind to receptors or other sites of drug action. Such labeled compounds are known as radiotracers. Some tracers distribute in tissues by partially following the metabolic pathways of their natural analogues; others interact with or bind with specificity in the tissues containing the particular receptor proteins for which they have affinity. It is important to recognize that PET technology can be used to trace the biodistribution of any compound (plus its radiometabolites) in living humans (and many other species as well), provided it can be radiolabeled with a PET isotope. The PET scanners can measure the distribution of radioactivity, but they cannot inform on the chemical species containing the radioactivity i.e., they cannot distinguish parent radiotracer from its radiometabolites in any field of view. Due to the short half-lives of most radioisotopes, the radiotracers must be produced using a cyclotron and radiochemistry laboratory that are in close proximity to the PET imaging facility. The half-life of $^{18}$F is long enough such that $^{18}$F-labeled radiotracers can be manufactured commercially at an offsite location.

PET scanning can involve whole body scanning or scanning of a tissue of interest, such as brain. Examples for each are presented herein.

IV. Pharmaceutical Compositions

In one aspect the present invention provides a pharmaceutical composition or a medicament comprising at least one compound of the present invention and optionally a pharmaceutically acceptable carrier. A pharmaceutical composition or medicament can be administered to a patient for the diagnosis or treatment of a condition, such as diarrhea, gastroenteritis, irritable bowel syndrome, cancer or a neuropsychiatric condition.

A. Formulation and Administration

The compounds of the present invention are useful in the manufacture of a pharmaceutical composition or a medicament comprising an effective amount thereof in conjunction or mixture with excipients or carriers suitable for either enteral or parenteral application.

Pharmaceutical compositions or medicaments for use in the present invention can be formulated by standard techniques using one or more physiologically acceptable carriers or excipients. Suitable pharmaceutical carriers are described herein and in "Remington's Pharmaceutical Sciences" by E. W. Martin. The compounds of the present invention and their physiologically acceptable salts and solvates can be formulated for administration by any suitable route, including via inhalation, topically, nasally, orally, parenterally, or rectally. Thus, the administration of the pharmaceutical composition may be made by intradermal, subdermal, intravenous, intramuscular, intranasal, intracerebral, intratracheal, intraarterial, intraperitoneal, intravesical, intrapleural, intracoronary or intratumoral injection, with a syringe or other devices. Transdermal administration is also contemplated, as are inhalation or aerosol administration. Tablets and capsules can be administered orally, rectally or vaginally.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a composition of the present invention, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

For oral administration, a pharmaceutical composition or a medicament can take the form of, for example, a tablet or a capsule prepared by conventional means with a pharmaceutically acceptable excipient. Preferred are tablets and gelatin capsules comprising the active ingredient, i.e., a composition of the present invention, together with (a) diluents or fillers, e.g., lactose, dextrose, sucrose, mannitol, sorbitol, cellulose (e.g., ethyl cellulose, microcrystalline cellulose), glycine, pectin, polyacrylates and/or calcium hydrogen phosphate, calcium sulfate, (b) lubricants, e.g., silica, talcum, stearic acid, its magnesium or calcium salt, metallic stearates, colloidal silicon dioxide, hydrogenated vegetable oil, corn starch, sodium benzoate, sodium acetate and/or polyethyleneglycol; for tablets also (c) binders, e.g., magnesium aluminum silicate, starch paste, gelatin, tragacanth, methylcellulose, sodium carboxymethylcellulose, polyvinylpyrrolidone and/or hydroxypropyl methylcellulose; if desired (d) disintegrants, e.g., starches (e.g., potato starch or sodium starch), glycolate, agar, alginic acid or its sodium salt, or effervescent mixtures; (e) wetting agents, e.g., sodium lauryl sulphate, and/or (f) absorbents, colorants, flavors and sweeteners.

Tablets may be either film coated or enteric coated according to methods known in the art. Liquid preparations for oral administration can take the form of, for example, solutions, syrups, or suspensions, or they can be presented as a dry product for constitution with water or other suitable vehicle before use. Such liquid preparations can be prepared by conventional means with pharmaceutically acceptable additives, for example, suspending agents, for example, sorbitol syrup, cellulose derivatives, or hydrogenated edible fats; emulsifying agents, for example, lecithin or acacia; non-aqueous vehicles, for example, almond oil, oily esters, ethyl alcohol, or fractionated vegetable oils; and preservatives, for example, methyl or propyl-p-hydroxybenzoates or sorbic acid. The preparations can also contain buffer salts, flavoring, coloring, and/or sweetening agents as appropriate. If desired, preparations for oral administration can be suitably formulated to give controlled release of the active composition.

For administration by inhalation the compounds may be conveniently delivered in the form of an aerosol spray presentation from pressurized packs or a nebulizer, with the use of a suitable propellant, for example, dichlorodifluoromethane, trichlorofluoromethane, dichlorotetrafluoroethane, 1,1,1,2-tetrafluorethane, carbon dioxide, or other suitable gas. In the case of a pressurized aerosol, the dosage unit can be determined by providing a valve to deliver a metered amount. Capsules and cartridges of, for example, gelatin for use in an inhaler or insufflator can be formulated containing a powder mix of the compound and a suitable powder base, for example, lactose or starch.

The compounds of the present invention can be formulated for parenteral administration by injection, for example by bolus injection or continuous infusion. Formulations for injection can be presented in unit dosage form, for example, in ampoules or in multi-dose containers, with an added preservative. Injectable compositions are preferably aqueous isotonic solutions or suspensions, and suppositories are preferably prepared from fatty emulsions or suspensions. The compositions may be sterilized and/or contain adjuvants, such as preserving, stabilizing, wetting or emulsifying agents, solution promoters, salts for regulating the osmotic pressure and/or buffers. Alternatively, the active ingredient can be in powder form for constitution with a suitable vehicle, for example, sterile pyrogen-free water, before use. In addition, they may also contain other therapeutically valuable substances. The compositions are prepared according to conventional mixing, granulating or coating methods, respectively, and contain about 0.1 to 75%, preferably about 1 to 50%, of the active ingredient.

Suitable formulations for transdermal application include an effective amount of a composition of the present invention with carrier. Preferred carriers include absorbable pharmacologically acceptable solvents to assist passage through the skin of the host. For example, transdermal devices are in the form of a bandage comprising a backing member, a reservoir containing the composition optionally with carriers, optionally a rate controlling barrier to deliver the composition to the skin of the host at a controlled and predetermined rate over a prolonged period of time, and means to secure the device to the skin. Matrix transdermal formulations may also be used.

Suitable formulations for topical application, e.g., to the skin and eyes, are preferably aqueous solutions, ointments, creams or gels well-known in the art. Such may contain solubilizers, stabilizers, tonicity enhancing agents, buffers and preservatives.

The compositions can also be formulated in rectal compositions, for example, suppositories or retention enemas, for example, containing conventional suppository bases, for example, cocoa butter or other glycerides.

Furthermore, the compositions can be formulated as a depot preparation. Such long-acting formulations can be administered by implantation (for example, subcutaneously or intramuscularly) or by intramuscular injection. Thus, for example, the composition can be formulated with suitable polymeric or hydrophobic materials (for example as an emulsion in an acceptable oil) or ion exchange resins, or as sparingly soluble derivatives, for example, as a sparingly soluble salt.

The compositions can, if desired, be presented in a pack or dispenser device that can contain one or more unit dosage forms containing the active ingredient. The pack can, for example, comprise metal or plastic foil, for example, a blister pack. The pack or dispenser device can be accompanied by instructions for administration.

In one embodiment of the present invention, a pharmaceutical composition or medicament comprises an effective amount of a compound of the present invention and another therapeutic agent, such as a chemotherapeutic agent. Examples of chemotherapeutic agents include, but are not limited to, daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine (CA), 5-azacytidine, hydroxyurea, deoxycoformycin, 4-hydroxyperoxycyclophosphor-amide, 5-fluorouracil (5-FU), 5-fluorodeoxyuridine (5-FUdR), methotrexate (MTX), colchicine, taxol, vincristine, vinblastine, etoposide, trimetrexate, teniposide, cisplatin and diethylstilbestrol (DES). See, generally, The Merck Manual of Diagnosis and Therapy, 15th Ed. 1987, pp. 1206-1228, Berkow et al., eds., Rahway, N.J.).

When used with a compound of the invention, such chemotherapeutic agent may be used individually (e.g., 5-FU and compound), sequentially (e.g., 5-FU and compound for a period of time followed by e.g., MTX and compound), or in combination with one or more other such chemotherapeutic agents (e.g., 5-FU, MTX and compound, or 5-FU, radiotherapy and compound). Administration may be by the same or different route of administration or together in the same pharmaceutical formulation.

In one aspect of the present invention, a therapeutically effective amount of a compound of the present invention is administered in combination with surgery, and optionally administration of another chemotherapeutic agent.

B. Dosing

In one embodiment of the present invention, a pharmaceutical composition or medicament is administered to a patient at a therapeutically effective dose to diagnose, prevent, treat, or control a neuropsychciatric condition, a neurological condition, or multidrug resistance. The pharmaceutical composition or medicament is administered to a patient in an amount sufficient to elicit an effective therapeutic or diagnostic response in the patient. An effective therapeutic or diagnostic response is a response that at least partially arrests or slows the symptoms or complications of the disease or permits diagnosis of the disease. An amount adequate to accomplish this is defined as "therapeutically effective dose."

The dosage of active compounds or compositions administered is dependent on the species of warm-blooded animal (mammal), the body weight, age, individual condition, surface area of the area to be treated and on the form of administration. The size of the dose also will be determined by the existence, nature, and extent of any adverse effects that accompany the administration of a particular compound in a particular subject. A unit dosage for administration to a mammal of about 50 to 70 kg may contain between about 5 and 500 mg of the active ingredient. Typically, a dosage of the compound of the present invention, is a dosage that is sufficient to achieve the desired effect.

Optimal dosing schedules can be calculated from measurements of compound accumulation in the body of a subject. In general, dosage is from 1 ng to 1,000 mg per kg of body weight and may be given once or more daily, weekly, monthly, or yearly. Persons of ordinary skill in the art can easily determine optimum dosages, dosing methodologies and repetition rates. One of skill in the art will be able to determine optimal dosing for administration of a radiotracer to a human being following established protocols known in the art, the disclosure herein, in particular, the experimental details where radiotracers were administered to monkeys.

Optimum dosages, toxicity, and therapeutic efficacy of some compounds may vary depending on the relative potency of individual compounds and can be determined by standard pharmaceutical procedures in cell cultures or experimental animals, for example, by determining the $LD_{50}$ (the dose lethal to 50% of the population) and the $ED_{50}$ (the dose therapeutically effective in 50% of the population). The dose ratio between toxic and therapeutic effects is the therapeutic index and can be expressed as the ratio, $LD_{50}/ED_{50}$. Compounds that exhibit large therapeutic indices are preferred. While compounds that exhibit toxic side effects can be used, care should be taken to design a delivery system that targets such compounds to the site of affected tissue to minimize potential damage to normal cells and, thereby, reduce side effects.

The data obtained from, for example, animal studies (e.g. rodents and monkeys herein) can be used to formulate a dosage range for use in humans. The dosage of compounds of the present invention lies preferably within a range of circulating concentrations that include the ED50 with little or no toxicity. The dosage can vary within this range depending upon the dosage form employed and the route of administration. For any small molecule compound used in the methods of the invention, the therapeutically effective dose can be estimated initially from cell culture assays. A dose can be formulated in animal models to achieve a circulating plasma concentration range that includes the IC50 (the concentration of the test compound that achieves a half-maximal inhibition of symptoms) as determined in cell culture. Such information can be used to more accurately determine useful doses in humans. Levels in plasma can be measured, for example, by high performance liquid chromatography (HPLC). In general, the dose equivalent of a small molecule compound is from about 1 ng/kg to 100 mg/kg for a typical subject.

As described herein, because dLop is a metabolite of an FDA-approved over-the-counter drug (loperamide), it should be safe to administer to humans.

The dosage of active compositions administered is also dependent on the nature of the agent. For example, a therapeutically effective amount of a compound of the present invention (i.e., an effective dosage) for, e.g., treatment of diarrhea, ranges from about 0.001 to 30 mg/kg body weight, preferably about 0.01 to 25 mg/kg body weight, more preferably about 0.1 to 20 mg/kg body weight, and even more preferably about 1 to 10 mg/kg, 2 to 9 mg/kg, 3 to 8 mg/kg, 4 to 7 mg/kg, or 5 to 6 mg/kg body weight. The compound can be administered one time per week for between about 1 to 10 weeks, preferably between 2 to 8 weeks, more preferably between about 3 to 7 weeks, and even more preferably for about 4, 5, or 6 weeks.

Exemplary doses of the compositions described herein, include milligram or microgram amounts of the composition per kilogram of subject or sample weight (e.g., about 1 microgram per-kilogram to about 500 milligrams per kilogram, about 100 micrograms per kilogram to about 5 milligrams per kilogram, or about 1 microgram per kilogram to about 50 micrograms per kilogram. It is furthermore understood that appropriate doses of a composition depend upon the potency of the composition with respect to the desired effect to be achieved. When one or more of these compositions is to be administered to an animal, a physician, veterinarian, or researcher may, for example, prescribe a relatively low dose at first, subsequently increasing the dose until an appropriate response is obtained. In addition, it is understood that the specific dose level for any particular animal subject will depend upon a variety of factors including the activity of the specific composition employed, the age, body weight, general health, gender, and diet of the subject, the time of administration, the route of administration, the rate of excretion, any drug combination, and the degree of expression or activity to be modulated.

In one embodiment of the present invention, a pharmaceutical composition or medicament comprising a compound of the present invention is administered, e.g., in a daily dose in the range from about 1 mg of compound per kg of subject weight (1 mg/kg) to about 1 g/kg. In another embodiment, the dose is a dose in the range of about 5 mg/kg to about 500 mg/kg. In yet another embodiment, the dose is about 10 mg/kg to about 250 mg/kg. In another embodiment, the dose is about 25 mg/kg to about 150 mg/kg. A preferred dose is about 10 mg/kg. The daily dose can be administered once per day or divided into subdoses and administered in multiple doses, e.g., twice, three times, or four times per day. However, as will be appreciated by a skilled artisan, compositions identified by methods of the present invention may be administered in different amounts and at different times. The skilled artisan will also appreciate that certain factors may influence the dosage and timing required to effectively treat a subject, including but not limited to the severity of the disease or disorder, previous treatments, the general health and/or age of the subject, and other diseases present. Moreover, treatment of a subject with a therapeutically effective amount of a composition can include a single treatment or, preferably, can include a series of treatments.

To achieve the desired therapeutic effect, compositions may be administered for multiple days at the therapeutically effective daily dose. Thus, therapeutically effective administration of compositions to treat a pathological condition or disease described herein in a subject requires periodic (e.g., daily) administration that continues for a period ranging from three days to two weeks or longer. Typically, compounds or compositions will be administered for at least three consecutive days, often for at least five consecutive days, more often for at least ten, and sometimes for 20, 30, 40 or more consecutive days. While consecutive daily doses are a preferred route to achieve a therapeutically effective dose, a therapeutically beneficial effect can be achieved even if the compounds or compositions are not administered daily, so long as the administration is repeated frequently enough to maintain a therapeutically effective concentration of the compound in the subject. For example, one can administer a compound or composition every other day, every third day, or, if higher dose ranges are employed and tolerated by the subject, once a week.

Following successful treatment, it may be desirable to have the subject undergo maintenance therapy to prevent the recurrence of the condition or disease treated.

V. Kits and Systems

For use in diagnostic, research, and therapeutic applications suggested above, kits and systems are also provided by the invention. In the diagnostic and research applications such kits and systems may include any or all of the following: assay reagents, buffers, a compound of the present invention, a P-gp preparation, a P-gp polypeptide, etc. A therapeutic product may include sterile saline or another pharmaceutically acceptable emulsion and suspension base.

In addition, the kits and systems may include instructional materials containing directions (i.e., protocols) for the practice of the methods of this invention. The instructions may be present in the subject kits in a variety of forms, one or more of which may be present in the kit. While the instructional materials typically comprise written or printed materials they are not limited to such. Any medium capable of storing such instructions and communicating them to an end user is contemplated by this invention. Such media include, but are not limited to electronic storage media (e.g., magnetic discs, tapes, cartridges, chips), optical media (e.g., CD ROM), and the like. Such media may include addresses to internet sites that provide such instructional materials.

A wide variety of kits, systems, and components can be prepared according to the present invention, depending upon the intended user of the kit and system and the particular needs of the user.

In a preferred embodiment of the present invention, the kit or system comprises a compound of the present invention, preferably an isolated radiolabeled dLop or dLop-related compound and (ii) a preparation of a P-glycoprotein.

The kits or systems according to the present invention may further comprise a reagent for assessing P-gp function Such reagents are described herein and are well known to those skilled in the art.

Additional kit embodiments of the present invention include optional functional components that would allow one of ordinary skill in the art to perform any of the method variations described herein.

Although the forgoing invention has been described in some detail by way of illustration and example for clarity and understanding, it will be readily apparent to one of ordinary skill in the art in light of the teachings of this invention that certain variations, changes, modifications and substitutions of equivalents may be made thereto without necessarily departing from the spirit and scope of this invention. As a result, the embodiments described herein are subject to various modifications, changes and the like, with the scope of this invention being determined solely by reference to the claims appended hereto. Those of skill in the art will readily recognize a variety of non-critical parameters that could be changed, altered or modified to yield essentially similar results. The headings used herein are for organizational purposes only and are not meant to be used to limit the scope of the description or the claims. As used throughout this application, the word "may" is used in a permissive sense (i.e., meaning having the potential to), rather than the mandatory sense (i.e., meaning must). Similarly, the words "include", "including", and "includes" mean including, but not limited to.

While each of the elements of the present invention is described herein as containing multiple embodiments, it should be understood that, unless indicated otherwise, each of the embodiments of a given element of the present invention is capable of being used with each of the embodiments of the other elements of the present invention and each such use is intended to form a distinct embodiment of the present invention.

The referenced patents, patent applications, and scientific literature, including accession numbers to GenBank database sequences, referred to herein are hereby incorporated by reference in their entirety as if each individual publication, patent or patent application were specifically and individually indicated to be incorporated by reference. Any conflict between any reference cited herein and the specific teachings of this specification shall be resolved in favor of the latter. Likewise, any conflict between an art-understood definition of a word or phrase and a definition of the word or phrase as specifically taught in this specification shall be resolved in favor of the latter.

As can be appreciated from the disclosure above, the present invention has a wide variety of applications. The invention is further illustrated by the following examples, which are only illustrative and are not intended to limit the definition and scope of the invention in any way.

VI. EXAMPLES

Example 1

General Methods (a) Reagents and Reactions

All reagents and organic solvents were ACS grade or higher and were used without further purification. 4 (4-chlorophenyl)-4-hydroxypiperidine, 4-bromo-2,2-diphenylbutyronitrile and N,N-di-isopropylethylamine (DIPEA) were purchased from Aldrich (Milwaukee, Wis.). DCPQ ((2R)-anti-5-{3-[4-(10,11-dichloromethanodibenzo-suber-5-yl) piperazin-1-yl]-2-hydroxypropoxy}quinoline trihydrochloride (Pfister et al., 1995, *Bioorg Med Chem Lett* 5:2473-2476) was a gift from Eli Lilly (Indianapolis, Ind.). Reactions were performed under argon atmosphere with standard Schlenk techniques.

For some studies, GlaxoSmithKline provided N-desmethyl-loperamide, the precursor for synthesis of $^{11}$C-loperamide. Eli Lilly provided DCPQ [(2R)-anti-5-{3-[4-(10,11-dichloromethanodibenzo-suber-5-yl)piperazin-1-yl]-2-hydroxypropoxy}quinoline trihydrochloride], which is a potent inhibitor of P-gp. DCPQ was previously reported as compound 14b (Pfister et al., 1995, *Bioorg Med Chem Lett* 5:2473-2476). Xenova Group, Ltd (UK), provided tariquidar, previously called XR9576 (Roe et al., 1999, *Bioorg Med Chem Lett* 9:595-600).

(b) Spectroscopic Analysis

Yields are recorded for chromatographically and spectroscopically ($^1$H and $^{13}$C NMR) pure materials. $^1$H NMR (400 MHz) and $^{13}$C NMR (100 MHz) spectra of all compounds were recorded on an Avance 400 spectrometer (Bruker; Billerica, Mass.). Chemical shifts are reported in δ units (ppm) downfield relative to the chemical shift for tetramethylsilane. Abbreviations br, s, d, t, and m denote broad, singlet, doublet, triplet, and multiplet, respectively.

Mass spectra were obtained on a Polaris-Q GC-MS instrument (Thermo Fisher Scientific Corp., Waltham, Mass.). LC-MS was performed on a LCQ Deca instrument (Thermo Fisher Scientific Corp.) equipped with a reverse-phase HPLC column (Synergi Fusion-RP, 4 µm, 150×2 mm; Phenomenex, Torrance, Calif.). The instrument was set up to perform electrospray ionization (spray voltage 5 kV, nitrogen sheath flow 65 units, auxiliary gas flow 10 units, capillary voltage 35 V, and capillary temperature 260° C.). For the characterization of synthesized compounds, the column was eluted at 150 µL/min, either isocratically or with a gradient between $H_2O$:MeOH:AcOH (90:10:0.5 by vol.) and MeOH:AcOH (100:0.5 v/v).

High resolution mass spectra (HRMS) were acquired at the Mass Spectrometry Laboratory, University of Illinois at Urbana Champaign (Urbana, Ill.) under electron ionization conditions with a double-focusing high resolution instrument (Autospec; Micromass Inc.). Samples were introduced through a direct insertion probe.

(c) Thin Layer Chromatography

Thin layer chromatography (TLC) was performed on silica gel layers (type 60 F254; EMD Chemicals, Gibbstown, N.J.), and compounds were visualized under UV light and by staining with Dragendorff's reagent.

(d) Melting Points

Melting points (M.p.) were measured with a Mel-Temp manual melting point apparatus (Electrothermal; Fisher Scientific, USA), and were uncorrected.

(e) Analysis of [$^{11}$C]dLop and its Metabolites

[$^{11}$C]N-Desmethyl-loperamide ([$^{11}$C]dLop, also referred to as [$^{11}$C]3; see scheme herein) and its radiometabolites in samples of biological material were analyzed on a Nova-Pak® C18 column (4 µm, 100×8 mm; Waters Corp., Milford, Mass.) housed within a radial compression module (RCM 100). The column was eluted with MeOH:$H_2O$:$Et_3$N (70:30:0.1 by vol.) at 2.0 mL/min, with eluate monitored with a flow through Na(Tl) scintillation detector (Bioscan, Washington, D.C.). Methanol (2 mL) was injected onto the column to show no residual radioactivity after each analysis run. Chromatographic data were corrected for physical decay to the time of HPLC injection, stored and analyzed by "Bio-Chrom Lite" software (Bioscan). The same HPLC method was applied for the determination of radiochemical purity, lipophilicity and radiochemical stability of [$^{11}$C]3 in various media.

(f) Measuring Carbon-11 or Fluorine-18

High activities of carbon-11 or fluorine-18 (>40 kBq, <40 MBq) were measured with a calibrated ionization chamber (Atomlab 300; Biodex Medical Systems, Shirley, N.Y.). Low activities of carbon-11 (<40 kBq) were measured in an automatic γ-counter (Model 1480 Wizard; Perkin-Elmer; Boston, Mass.) with an electronic window set between 360-1800 keV (counting efficiency, 51.84%). Measurements of carbon-11 were corrected for any significant background and for physical decay with a half-life of 20.385 min (Weber et al., 1989, *MIRD:Radionuclide Data and Decay Schemes*. New York: Society of Nuclear Medicine 447). Measurements of fluorine-18 were similarly corrected for its half-life of 10.9.7 min.

(g) Animals

P-gp knockout mice (mdr-1a(−/−)) Schinkel et al, 1994, *Cell* 77:491-502) (model; 001487-MM, double homozygotes) and wild type mice (mdr-1a(+/+)) (Model; FVB) were purchased from Taconic Farm (Germantown, N.Y.).

Healthy rhesus monkeys (*Macaca mulatta*) were used in this study. All animal experiments were performed in accordance with the Guide for Care and Use of Laboratory Animals (Clark et al., 1996, *Guide for the Care and Use of Laboratory Animals*, Washington D.C.: National Academy Press) and were approved by the National Institute of Mental Health Animal Care and Use Committee. Group data are expressed as mean±S.D.

Example 2

Synthesis of $^{11}$C Loperamide $^{11}$C-Loperamide (Wilson et al., 2005, *J Label Compd Radiopharm* 48:S142) was prepared automatically within a lead-shielded hot cell from cyclotron-produced $^{11}$C-carbon dioxide in a commercial apparatus (Mel Microlab; Bioscan, Washington D.C., USA). $^{11}$C-Carbon dioxide (51.8 GBq) was produced according to the $^{14}$N(p,α)$^{11}$C reaction by irradiating nitrogen that contained oxygen (1%) for 20 min at an initial pressure of 11 atmospheres with a proton beam (16.5 MeV; 45 μA) using a PETrace cyclotron (GE Healthcare, USA). The $^{11}$C-carbon dioxide was reduced to $^{11}$C-methane and further to $^{11}$C-iodomethane by repetitive high temperature direct iodinations (Larsen et al., 1997, *Appl Radiat Isot* 48:153-157). The $^{11}$C-iodomethane was then released from this apparatus in a stream of He (15 mL/min) into a PLC-controlled semi-robotic Synthia apparatus (Synthia, Uppsala University PET Centre, Uppsala, Sweden). The helium containing $^{11}$C-iodomethane was bubbled into a septum-sealed 1-mL vial containing a solution of N-desmethyl-loperamide (1.5 mg, 3.25 μmol) and KOH (5.0 mg, 89.3 μmol) in 400 μL anhydrous DMSO. When the radioactivity in the vial maximized, the reaction mixture was heated at 80° C. for 6 min and then diluted with $H_2O$ (500 μL). The crude material was injected onto a Luna C18 column (10 μm, 10×250 mm; Phenomenex, Torrance, Calif.) and then eluted at 8 mL/min with 0.1% TFA/MeCN (55:45 v/v). While the eluate was monitored for radioactivity and absorbance at 225 nm (Bioscan HC-003, pin diode for γ-detection; Beckman Gold 166 for UV absorbance), $^{11}$C-loperamide was collected ($t_R$=8.7 min) into a 10-mL round-bottom flask and evaporated to dryness. The residue was dissolved in EtOH (0.5 mL) and 0.9% NaCl (10 mL), which was then sterilized by membrane filtration (Millex MP, Millipore, Bedford, Mass., USA) to which sterile $NaHCO_3$ for injection (200 μL; 8.4% w/v, Hospira, Inc.) was added aseptically. The pH of the dose was 8.5.

Radiochemical purity was determined on a Prodigy $C_{18}$ column (4.6×250 mm, 10 μm; Phenomenex) eluted with 0.1% TFA/MeCN (50:50 v/v) at 2.5 mL/min ($t_R$=4.30 min). Identity was confirmed by co-injection with authentic loperamide and observation of its comobility (Beckman Gold 166 for UV absorbance; Bioscan HC-003, pin diode for γ-detection), and by LC-MS-MS analysis of associated carrier.

$^{11}$C-Loperamide was prepared from N-desmethyl-loperamide with an overall decay-corrected radiochemical yield of 11.3±1.4% and a radiochemical purity of more than 99% (n=13). The specific activity, decay corrected to the end of synthesis, was 42.6±23.9 GBq/μmol (n=13) with an average radioactivity of 1.7±0.6 GBq. The overall time of preparation was 37 min. The mass associated with the injected doses, as reported below, were calculated for time of injection.

Example 3

In Vitro Receptor Binding

The affinity of loperamide and dLop at three opiate receptors (delta, kappa, and mu) was measured using radiolabeled agonists for each receptor subtype. Detailed binding protocols are available on the web site for The National Institute of Mental Health Psychoactive Drug Screening Program.

Loperamide and dLop had high affinity and quite high selectivity for binding to opiate receptors over δ and κ subtypes (Table 1). Loperamide is an agonist; therefore its affinity was measured using agonist radiotracers.

Table 1 shows the affinity of loperamide and dLop for three cloned human opiate receptor subtypes:

| | Agonist | $K_i$ (nM)* | |
|---|---|---|---|
| Receptor | Radiotracer | Loperamide | dLop |
| μ | $^3$H-DAMGO | 0.31 ± 0.03 | 0.56 ± 0.05 |
| δ | $^3$H-DADLE | 116 ± 7 | 328 ± 22 |
| κ | $^3$H-U69,593 | 47 ± 4 | 73 ± 7 |

*$K_i$ (inhibition constants) values are the mean ± SD of four competitive binding experiments.

Example 4

Plasma Analysis of [$^{11}$C]Loperamide in Nonhuman Primates

An intravenous perfusion line, filled with 0.9% NaCl, was used for the [$^{11}$C]loperamide radiotracer injection. A blood sample (2 mL) was withdrawn before radiotracer administration to determine plasma protein binding, as previously described (Zoghbi et al., 2006, *J Nucl Med* 47:520-527). Eight arterial blood samples (0.5 mL each) were drawn into heparin-treated syringes at 15 s intervals until 2 min, followed by 1 mL aliquots at 3, 5, 10, 20, 30, 45, 60, 75, 90, and 120 min. Plasma $^{11}$C-loperamide was quantified using radiochromatography (HPLC; methanol:water:triethylamine, 75:25:0.1; by vol. at 2.0 mL/min) and γ-counting, as previously described (Zoghbi et al., 2006, *J Nucl Med* 47:520-527).

Plasma free fraction ($f_P$) was determined at baseline condition and after administration of DCPQ and tariquidar. Plasma free fraction was measured in triplicate using ultracentrifugation, as described previously (Gandelman et al., 1994, *J Pharm Sci* 83:1014-1019).

At least six radiometabolites were detected in monkey arterial plasma. Plasma samples at 15 min showed two major radiometabolite peaks (FIG. 1A). The most polar peak (a)

eluted at the void volume of the column (14.1%) and the other (e) immediately before the parent peak (2.6%) (FIG. 1A). The latter peak is almost certainly composed mainly of [$^{11}$C]dLop because of its coelution with authentic dLop under different elution conditions, and because this is the expected major metabolite of [$^{11}$C]loperamide. Three minor peaks (1.7% (b), 0.32% (c), and 0.24% (d)) were detected between the column void volume peak and dLop peaks (FIG. 1A). These three peaks were difficult to resolve at later time points without extending the time length of each radiochromatogram and compromising the global information of the arterial input function. Therefore, these three radiometabolites were combined and subsequently called "met B". One minor radiometabolite (0.1%, (g)) eluted after the parent peak and was presumably more lipophilic than loperamide (FIG. 1A).

Figure 2:
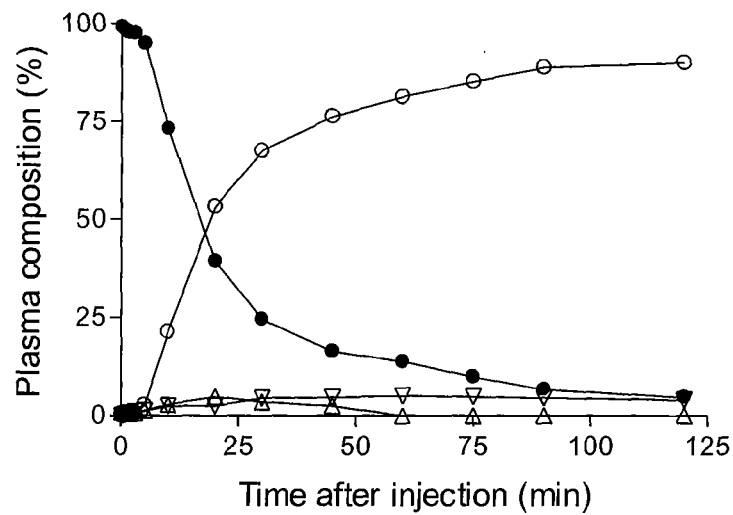
FIG. 2 depicts the time course of the composition of radioactivity extracted from arterial plasma after intrvenous injection of [$^{11}$C]loperamide in a monkey. Relative to peaks in FIG. 1, loperamide is f, dLop is e, the most polar is a, and pooled intermediates are b, c, and d. Data are shown for [$^{11}$C]loperamide (●); dLop (□), the most polar radiometabolite (○); and the 3 pooled intermediate radiometabolites (Δ). Details are described in Examples 4 and 8.

[$^{11}$C]Loperamide was stable in vitro for 30 min at room temperature in whole blood (93%) and plasma (99%). [$^{11}$C]Loperamide is rapidly metabolized in vivo and represented 50% of plasma radioactivity at about 20 min (FIG. 2). The recovery of radioactivity from the standards and all other plasma samples into CH$_3$CN was 92.5±6.9% (n=69), with no retention of radioactivity on the HPLC column.

Example 5

PET Imaging of [$^{11}$C]Loperamide in Nonhuman Primate

Three male rhesus monkeys (*Macaca mulatta*; 11.5±1.4 kg, with these and subsequent data expressed as mean±SD) were fasted overnight, immobilized with ketamine (10 mg/kg i.m.), intubated, placed on a ventilator, and anesthetized with 1.6% isoflurane in O$_2$. After injecting [$^{11}$C]loperamide (286±55 MBq i.v. in 4-5 mL; 0.76±0.3 nmol/kg), dynamic PET scans were acquired on either the HRRT (High Resolution Research Tomograph; Siemens, Knoxville, Tenn., USA) or the Advance PET tomograph (GE Healthcare, Waukesha, Wis.), both of which were cross-calibrated. Although these two cameras have different resolution, the regions of interest were large enough to mask this performance difference (Imaizumi et al., 2007, *Synapse* 61:595-605). For DCPQ, a baseline scan was performed in the morning and a P-gp blocked scan in the afternoon in the same animal, with injections separated by three hours. Three doses of DCPQ (1, 3, and 8 mg/kg i.v.) and one dose of tariquidar (8 mg/kg i.v.) were administered, each at 30 min before the radiotracer. For tariquidar only a blockade scan was acquired and compared to the baseline scans of three other animals.

PET images were co-registered to a magnetic resonance image template of a monkey brain. Tomographic images were analyzed with PMOD 2.7 (pixel-wise modeling computer software; PMOD Group, Adliswil, Switzerland). Regions of interest were drawn on coronal slices. Decay-corrected radioactivity was expressed as % standardized uptake value (% SUV), which normalizes for injected activity and body weight. % SUV=(% injected activity per cm3 brain)×(g body weight).

Figure 3:
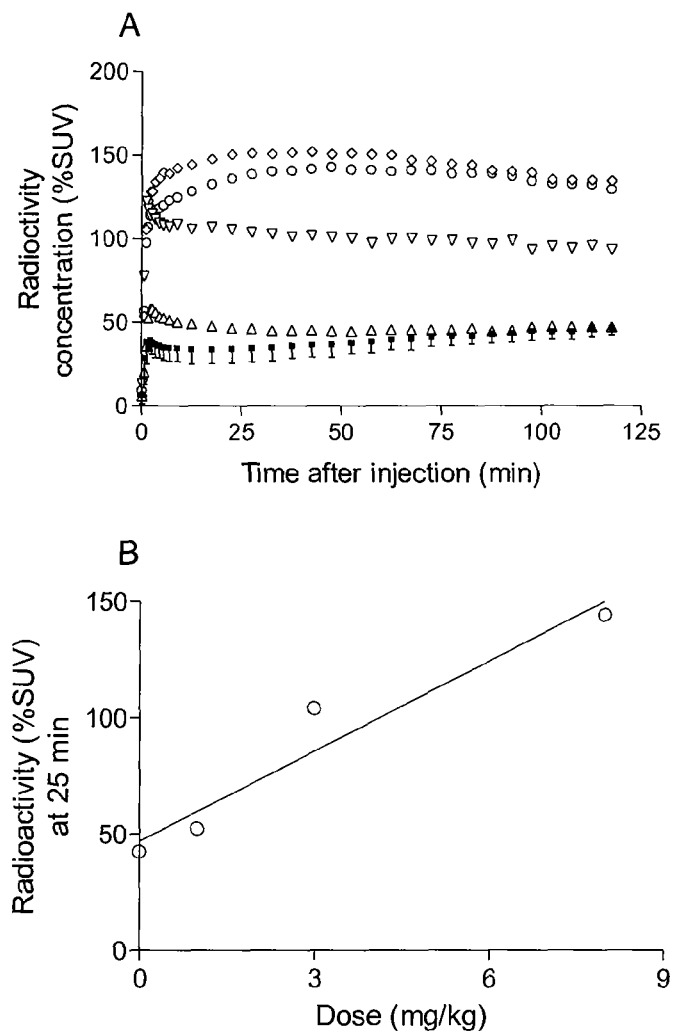
FIG. 3 depicts an effect of a P-gp inhibitor, DCPQ or tariquidar, on brain uptake of radioactivity in a monkey. (A) Brain radioactivity was measured at baseline (■). The unilateral error bars on the baseline study are the SD from 3 scans. Data are shown for 3 doses of DCPQ (1.0 (Δ), 3.0 (□), and 8.0 (◇) mg/kg) and 1 dose of tariquidar (8.0 mg/kg (○)). These P-gp inhibitors were injected intravenously 30 min before [$^{11}$C]loperamide. Peak radioactivity in brain increased 3.7 fold at a dose of 8.0 mg/kg for tariquidar or DCPQ. Concentrations of radioactivity in brain were corrected for their vascular component, assuming 5% of brain volume. (B) Relationship between DCPQ doses (0, 1, 3, and 8 mg/kg) and concentration of radioactivity (% SUV) at 25 min in monkey forebrain. Details are described in Examples 5 and 8.

Pre-administration of either of two P-gp inhibitors, DCPQ or tariquidar, caused brain activity to increase quickly after injection of [$^{11}$C]loperamide. Under baseline conditions in three monkeys, brain uptake was low (~40% SUV) and quite stable during the 120 min scan (FIG. 3A). Administration of DCPQ 30 min before the radiotracer quickly increased brain activity in a dose-dependent manner. The enhanced brain uptake was apparent within 1 to 3 min of radiotracer injection and relatively stable thereafter. The lowest dose (1 mg/kg) had minimal effect, but the higher doses (3 and 8 mg/kg) increased brain activity ~2.5 and ~3.5 fold, respectively (FIG. 3A). Increasing doses of DCPQ caused a linear increase of brain uptake at 25 min and showed no evidence of reaching a maximal effect at 8 mg/kg i.v. (FIG. 3B).

Figure 4:
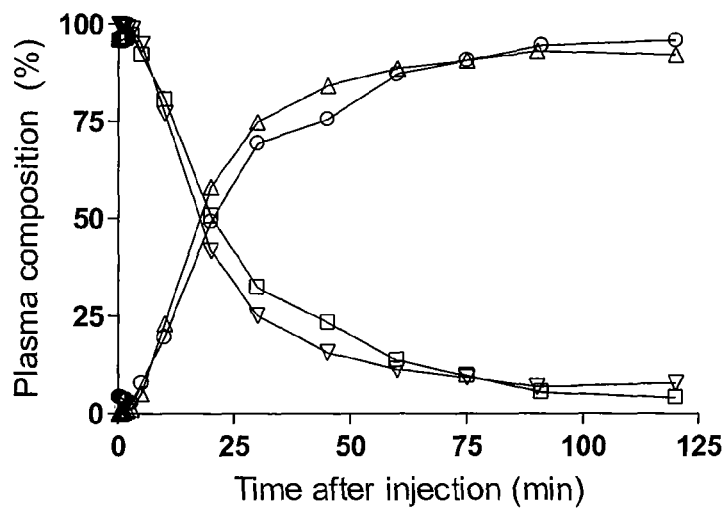
FIG. 4 depicts an effect of DCPQ on the composition of radioactivity in plasma after 2 injections of [$^{11}$C]loperamide into monkey. The baseline study was performed in the morning. DCPQ (8 mg/kg i.v.) was administered 30 min before the radiotracer to the same monkey in the afternoon. All radiometabolites were combined for each study. Data are shown for [$^{11}$C]loperamide at baseline (□) and after DCPQ (∇); total radiometabolites at baseline (○) and after DCPQ (Δ). Details are described in Examples 5 and 8.

P-gp is widely distributed in the body, including gastrointestinal tract, liver, and kidneys, and may significantly modulate metabolism and excretion of drugs. To determine whether the increase in brain activity following DCPQ occurred via a peripheral mechanism, parent radiotracer and radiometabolites were measured in arterial plasma at baseline and after P-gp blockade. At baseline and after DCPQ (8 mg/kg i.v.), the concentration of parent radiotracer quickly decreased and was 50% of total plasma activity at 17 and 20 min, respectively (FIG. 4). The maximal plasma concentration of [$^{11}$C]loperamide was also similar at baseline (446% SUV) and after DCPQ (408% SUV). As a measure of total exposure to brain, the area under the curve of plasma $^{11}$C-loperamide concentration versus time was calculated with a triexponential fit. The area to infinity was 359 at baseline and 417 kBq·min·mL$^{-1}$ after DCPQ. Thus, the almost 3.5 fold increase in forebrain activity could not be explained by a modest 16% increase in plasma exposure. Instead, the effect of DCPQ was likely due to inhibiting P-gp at the blood-brain barrier. To confirm this action, another P-gp inhibitor, tariquidar, whose chemical structure greatly differs from that of DCPQ, was injected. Tariquidar was equipotent with DCPQ when both were injected at 8.0 mg/kg i.v. (FIG. 3A).

Finally, increased brain uptake after P-gp inhibition was not caused by competitive binding of radiotracer from binding to plasma proteins. DCPQ had a slight but inconsistent effect on the plasma free fraction ($f_P$) of [$^{11}$C]loperamide. At 1.0 mg/kg DCPQ, $f_P$ increased 12%, but at the doses of 3.0 and 8.0 mg/kg, $f_P$ decreased 13% and 8.3%, respectively (Table 2). The plasma free fraction was negligibly affected by tariquidar (8 mg/kg).

Table 2 shows an effect of P-gp inhibitors on plasma free fraction ($f_P$) in monkey.

|  | Plasma free fraction ($f_P$) | | |
| --- | --- | --- | --- |
| P-gp Inhibitor (mg/kg) | Baseline | P-gp Inhibition | Δ |
| DCPQ (1.0) | 5.1 ± 0.2 | 5.7 ± 0.3 | +12% |
| DCPQ (3.0) | 1.6 ± 0.6 | 1.4 ± 0.5 | −13% |
| DCPQ (8.0) | 4.8 ± 1.7 | 4.4 ± 1.4 | −8.3% |
| Tariquidar (8.0) | 1.64 ± 0.56 | 1.71 ± 0.5 | +4.3% |

Values are the mean ± SD of at least three observations. The percent difference (Δ) was calculated relative to the baseline.

Example 6

PET Imaging Studies of [$^{11}$C]Loperamide in Mice

Three knockout (28±5 g; mdr-1a/b(−/−); model 001487-MM, double homozygotes) (Schinkel et al, 1996, *J Clin Invest* 97:2517-2524) and three wild type (31±2 g; mdr-1a/b (+/+); model FVB) mice were anesthetized with 1.5% isoflurane and injected via tail vein with [$^{11}$C]loperamide, 15.7±2.0 MBq (15.8±2.7 nmol/kg) and 16.8±2.1 MBq (15.7+ 2.7 nmol/kg), respectively. The volume of the injectate ranged between 0.1 and 0.15 mL which was infused over a period of 15 to 20 s. One knockout and one wild type mouse was paired and scanned simultaneously on the Advanced Technology Laboratory Animal Scanner (Seidel et al., 2003, *IEEE Trans Nucl Sci* 50:1347-1350), as previously described (Liow et al., 2007, *Synapse* 96:96-105). Serial dynamic images were acquired for 100 min, with frames of 6×20 s, 5×1 min, 4×2 min, 3×5 min, 3×10 min, and 2×20 min. 3D order subset expectation maximization algorithm was used to reconstruct data into 17 coronal slices, achieving a resolution of 1.6 mm full-width at half maximum (Johnson et al., 2002, *Mol Imag Biol* 4:S22 (abstract)). The small mouse brain causes little scatter and attenuation of the gamma emissions from carbon-11, and, thus, no correction for scatter or attenuation was performed.

Figure 5:
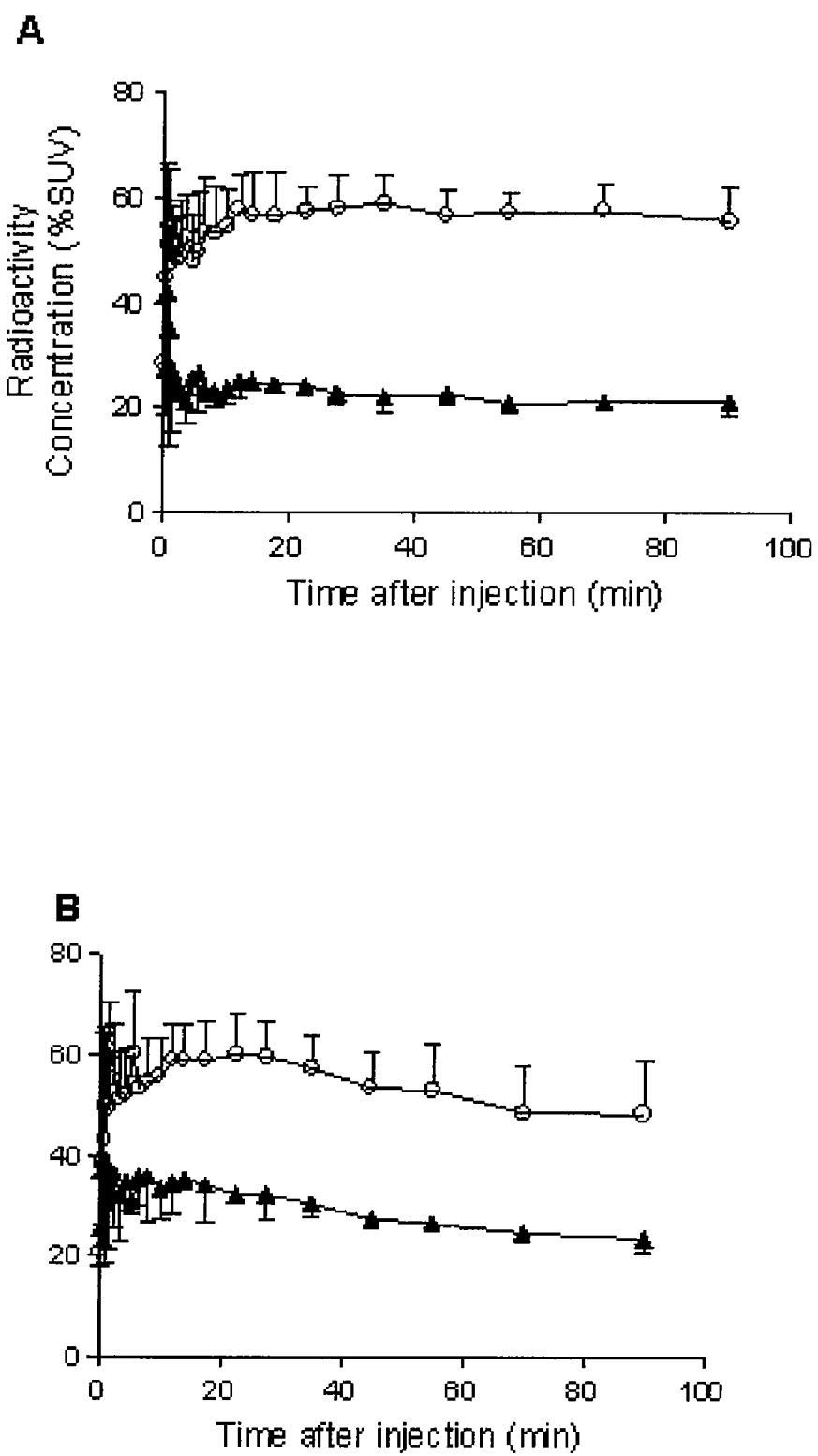
FIG. 5 depicts PET measurement of radioactivity in forebrain (A) and cerebellum (B) of P-gp knock-out (○) and wild type (▲) mice after administration of [$^{11}$C]loperamide. The unilateral error bars represent the SD for 3 knockout and 3 wild type mice. Details are described in Examples 6 and 8.

The effect of genetic disruption of P-gp in mice on brain radioactivity uptake after injecting [$^{11}$C]loperamide was similar to that of pharmacological inhibition in monkeys. The maximal activity in forebrain and cerebellum of knockout mice was quickly 2.7 and 1.9-fold higher, respectively, than that in wild type mice (FIG. 5).

Example 7

Ex Vivo Analysis of [$^{11}$C]Loperamide in Mouse Plasma and Brain

Five P-gp knockout (23.5±2.5 g) and five wild type (30.2±2.1 g) mice were anesthetized with 1.5% isoflurane in $O_2$, and [$^{11}$C]loperamide was injected via the tail vein. The knockout mice received 15.2±6 MBq (22.3±7 nmol/kg), and the wild type mice received 36.4±3 MBq (50.0±20 nmol/kg). At 30 min after radiotracer injection, anticoagulated blood was removed by cardiac puncture, and the brain was harvested. Plasma was separated from whole blood by centrifugation at 1,800 g for 1 min. Plasma samples were quantified for radioactivity as previously described (Zoghbi et al., 2006, *J Nucl Med* 47:520-527) in an automatic gamma counter. Forebrain and cerebellum were separately homogenized using a hand held tissue Tearor (model 985-370; BioSpec Products Inc.) in 1.5 times volume acetonitrile containing carrier loperamide, followed by homogenization with additional $H_2O$ (500 µL). The homogenates were measured in the y-counter to calculate the % recovery of radioactivity into the acetonitrile extracts. The homogenates were then centrifuged at 10,000×g for 1 min. The clear pre-filtered supernatant liquids were injected onto a radio-HPLC Novapak® $C_{18}$ column (4 µm, 100×8 mm; Waters Corp., Milford, Mass., USA) housed in a radial compression module RCM-100 and eluted with methanol:water:triethylamine (75:25:0.1; by vol.) at 2.0 mL/min. The eluate was monitored with an in-line flow-through Na(Tl) scintillation detector (Bioscan, Washington D.C., USA). Plasma parent and radiometabolite concentrations were calculated as the product of the radio-HPLC fraction of interest and the total plasma radioactivity concentration (dpm/mL). For simultaneous identification and quantification of radioactive dLop and loperamide, internal standards of both non-radioactive compounds were added to the tissue preparations for detection by UV absorbance.

In this experiment, at least four radiometabolites were detected in plasma, forebrain, and cerebellum of mice after intravenous injection of [$^{11}$C]loperamide. The radiochromatogram of plasma (FIG. 1B) showed a peak (a) that eluted at the void volume of the column. It was the most polar and designated radiometabolite A in Table 3. The next 3 minor peaks (b, c, and d) were combined and reported as radiometabolite B. Peak e was the most lipophilic radiometabolite and was found to coelute with added authentic dLop. The parent radiotracer (peak f) was the most lipophilic and eluted last. Furthermore, Peak (e) and reference dLop eluted at a retention time of 5.0 min (10 mL) using a mobile phase of methanol:water:triethylamine, 75:25:0.1; by vol. at 2.0 mL/min. The same two peaks remained associated after increasing the polarity of the mobile phase (HPLC; methanol:water:triethylamine, 70:30:0.1; by vol. at 2.0 mL/min) so that the retention time of peak e became 7.2 min (14.4 mL). At this extended retention time, peak (e) remained a single and symmetrical one. This evidence strongly indicates that this peak is $^{11}$C-dLop radiometabolite.

Table 3 shows the concentration of $^{11}$C-loperamide and its radiometabolites in the forebrain (A), and Plasma (B) of P-gp knockout (KO) and wildtype (WT) mice.

| Radiochemical Species | KO | WT | KO/WT Ratio |
|---|---|---|---|
| | Forebrain Concentration (% SUV)* | | |
| Radiometabolite [$^{11}$C]A | 1.3 ± 0.5 | 2.2 ± 0.7 | 0.6 |
| Radiometabolite [$^{11}$C]B | 0.3 ± 0.2 | 0.7 ± 0.3 | 0.4 |
| Radiometabolite [$^{11}$C]C | 1.6 ± 0.8 | 0.2 ± 0.1 | 8.0 |
| [$^{11}$C]dLop | 35.7 ± 9.9 | 2.3 ± 0.2 | 16 |
| Total | 38.9 ± 9.5 | 5.4 ± 1.2 | 7.0 |
| | Plasma Concentration (% SUV)* | | |
| Radiometabolite [$^{11}$C]A | 12.5 ± 5.7 | 16.9 ± 1.8 | 0.7 |
| Radiometabolite [$^{11}$C]B | 7.8 ± 7.7 | 5.5 ± 4.1 | 1.4 |
| Radiometabolite [$^{11}$C]C | 0.1 ± 0.1 | 0.1 ± 0.1 | 1.0 |
| [$^{11}$C]dLop | 1.7 ± 0.39 | 2.8 ± 0.2 | 0.6 |
| Total | 22.1 ± 5.3 | 25.3 ± 2.6 | 0.9 |

Three P-gp knockout and five wild type mice were killed 30 min after intravenous injection of $^{11}$C-loperamide.
*Values are mean ± SD.

The brain uptake of [$^{11}$C]loperamide and [$^{11}$C]dLop was markedly increased in P-gp knockout compared to wild type mice, confirming that both drugs are substrates for this efflux transporter. [$^{11}$C]Loperamide was increased 16-fold and [$^{11}$C]dLop 17-fold in forebrain and cerebellum (Table 3). The brain contained other radiometabolites (A and B) that were apparently not substrates and showed minimal differences between animals. These radiometabolites blunted differences between animals such that total radioactivity (i.e., of parent radiotracer and all radiometabolites) in forebrain of P-gp knockout mice was only fourfold greater than that of wild type mice (50.9±19.9% SUV vs. 12.5±1.5% SUV, Table 3). These direct ex vivo measurements of total radioactivity are the most relevant to compare with PET imaging, since PET detects radioactivity from all chemical species containing $^{11}$C. The direct measurements showed a 4-fold increase in forebrain total radioactivity of knockout compared to wild type animals (Table 3), whereas PET imaging found only 2.7-fold increase (FIG. 5).

Example 8

Comparative Studies using [$^{11}$C]Loperamide and [$^{11}$C]dLop

Using the $^{11}$C-labeled form, it was confirmed that loperamide is an avid substrate for P-gp at the blood-brain barrier in two species, mice and monkeys. Two structurally dissimilar inhibitors, DCPQ and tariquidar have high affinities to the P-gp of 5.3 nM (Ekins et al., 2002, *Mol Pharmacol* 61:974-

981) and 5.1 nM (Martin et al., 1999, *British J Pharmacol* 128:403-411), respectively. These inhibitors rapidly increased the brain activity in monkey. The enhanced uptake was fairly linear in the DCPQ dose range of 1 to 8 mg/kg i.v. and showed no evidence of a plateau or maximal effect. At the highest dose tested (8 mg/kg i.v.), both DCPQ and tariquidar were equipotent and increased brain activity ~3.5 fold. Comparable studies were performed in mice where P-gp knockout animals were used rather than pharmacological inhibition. PET imaging showed that the brains of knockout mice had about three-fold greater activity than those of wild type animals. This enhancement, however, was blunted by the limited anatomic resolution of PET. Ex vivo studies in these mice showed brain activity derived primarily from two compounds, the parent radiotracer $^{11}$C-loperamide and the radiopeak (e) (FIG. 1), which was deduced to be [$^{11}$C]dLop metabolite. Unlike PET, these ex vivo measurements were not confounded by limited resolution and its resulting partial volume errors. The concentrations of $^{11}$C-loperamide and [$^{11}$C]dLop at 30 min were elevated 16 and 17 fold in knockout compared to wild type mice.

In the light of these results, [$^{11}$C]dLop is a preferred radiotracer compared to [$^{11}$C]loperamide to assess P-gp function at the blood-brain barrier, since it will have one less contaminating radiometabolite. The structures of these two compounds clarify this point.

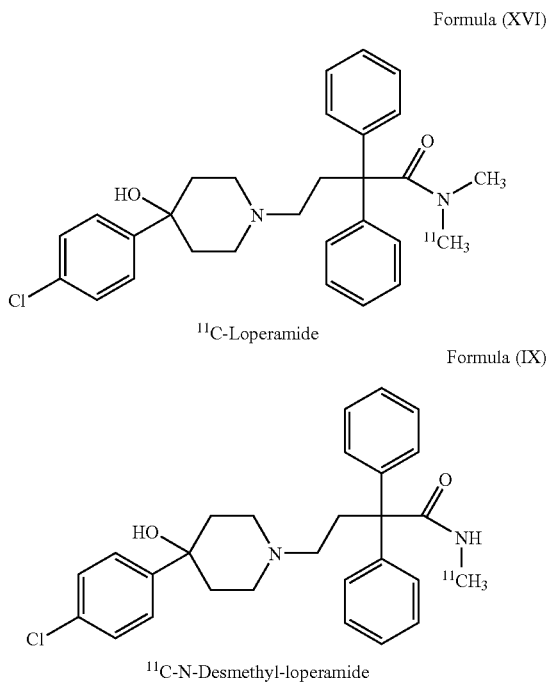

Formula (XVI)

$^{11}$C-Loperamide

Formula (IX)

$^{11}$C-N-Desmethyl-loperamide

When [$^{11}$C]loperamide is N-demethylated, it is anticipated that both $^{11}$C-methyl and $^{12}$C-methyl are equally likely to be removed and subsequently metabolized to $^{11/12}$C-labeled $CH_3OH$, $CH_2O$, $HCO_2H$, and $CO_2$. These compounds in the oxidation route have little entry in brain (Gunn et al., 2000, *Nucl Med* 41:605-611). In stark contrast to the metabolism of [$^{11}$C]loperamide, further N-demethylation of [$^{11}$C]dLop leads to radiometabolites, ultimately [$^{11}$C]$CO_2$, that has minimal brain entry. Thus, [$^{11}$C]loperamide is similar to many other P-gp substrate radiotracers mentioned in the Introduction by generating radiometabolites that confound PET measurements of brain activity. In this case, however, the confounding metabolite, [$^{11}$C]dLop, surprisingly was found to be a superior PET radiotracer.

Inactivation of P-gp function with either pharmacological inhibition in monkeys or genetic knockout in mice caused a rapid and sustained increase of brain activity after injection of [$^{11}$C]loperamide. The enhanced uptake was near maximal within a few min after injecting both monkeys and mice. The rapid effect of P-gp inhibition is consistent with this efflux pump blocking entry rather than facilitating removal of the radiotracer. Although both would have the same net effect, facilitating removal would likely be a slower process, first allowing entry, then diffusion in extracellular space, and finally removal from brain. In fact, the current model for P-gp function proposes that drugs are removed while in the membrane lipid bilayer (Gottesmann et al., 2002, *Nat Rev Cancer* 2:48-58)—i.e., before they enter the brain's extracellular space.

Compared to ex vivo measurements, PET brain imaging was confounded by limited anatomic resolution and contamination from [$^{11}$C]loperamide derived radiometabolites. The more accurate ex vivo measurements demonstrated markedly increased concentrations of [$^{11}$C]loperamide (16 fold) and [$^{11}$C]dLop (17 fold) in P-gp knockout compared to wild type brain. These high ratios reflect, in part, the thorough-ness of P-gp to block brain entry of these two compounds. That is, the denominator of the ratio (i.e., brain uptake in wild type mice) is extraordinarily low, which has significant implications for PET imaging. Although one can measure decreased P-gp function as increased tissue radioactivity, one would likely not be able to measure enhanced P-gp function, since tissue radioactivity is already at almost immeasurably low levels. For example, some cases of drug resistance in epilepsy may be caused by locally enhanced P-gp function, and thus drug removal, at the epileptogenic focus (Siddiqui et al., 2003, *New Engl J Med* 348:1442-1448). [$^{11}$C]Loperamide and [$^{11}$C]dLop would likely be unable to measure such increased P-gp function, since baseline activity is so low, at least in nonhuman primates. In this regard, a less avid P-gp substrate radiotracer would be superior to loperamide to measure enhanced P-gp function.

Did [$^{11}$C]loperamide and [$^{11}$C]dLop show measurable binding to opiate receptors in vivo? Mu opiate receptors have significantly higher densities in forebrain than cerebellum of mouse (Gunn et al., 2000, *J Nucl Med* 41:605-611). Thus, if the radiotracer has significant receptor binding greater than nonspecific levels, its concentration should be higher in forebrain than in cerebellum. The PET imaging data shown herein may not useful to address this question, because partial volume errors will cross-contaminate cerebellum and forebrain and because the PET measurements of total radioactivity are contaminated by several radiometabolites, particularly those derived from [$^{11}$C]loperamide. In contrast, the ex vivo data shown herein have no partial volume errors and can separately identify [$^{11}$C]loperamide and [$^{11}$C]dLop by radiochromatography. At 30 min after injection in knockout mice, the ratio of concentrations in forebrain to cerebellum was 1.5 for [$^{11}$C]loperamide (25.4% vs. 16.9%) and about 1 for [$^{11}$C]dLop (12.1% vs. 14.4%). One-way analysis of variance demonstrated that there was no significant brain regional differences ($\alpha$=0.05) in the distribution of either radiochemical species.

[$^{11}$C]Loperamide and its N-desmethyl metabolite, [$^{11}$C] dLop, are avid substrates for P-gp efflux at the blood-brain barrier. Surprisingly, [$^{11}$C]dLop has been found to have superior properties to the parent radiotracer for measuring P-gp function, since its further demethylation generates radiometabolites that have limited entry into brain.

Example 9

Synthesis and $^{11}$C Labeling of N-Desmethyl-Loperamide

[$^{11}$C]Loperamide (4-(4-(4-chlorophenyl)-4-hydroxypiperidin-1-yl)-N,N-dimethyl-2,2-diphenylbutanamide) is a µ-opiod receptor agonist and a P-gp efflux pump substrate which has been proposed for the study of P-gp function in vivo (see Examples above). [$^{11}$C]dLop has been identified as one of its major radiometabolites in vivo and only under conditions of P-gp inhibition readily enters rodent and monkey brain (Yoshida et al., 1979, *Biomed Mass Spectrum* 6:253-259; Examples above). Therefore, [$^{11}$C]dLop was considered a prospective PET radiotracer for assessing brain P-gp function with advantages over [$^{11}$C]loperamide, such as fewer radiometabolites and lack of receptor binding (see Examples above).

The preparation of [$^{11}$C]dLop required a convenient synthesis of the primary amide, compound 1 (see scheme below), a compound for which synthesis details were not yet documented (Wilson et al., 2005, *J Labelled Compd Radiopharm* 48:S142 (abstract); Stokbroekx et al., 1973, *J Med Chem* 16:782-786). The following scheme describes a preferred method to synthesize N-Desmethyl-loperamide (compound 3; see scheme below) and [$^{11}$C]dLop (compound [$^{11}$C]3; see scheme below):

Reaction i: 4-(4-(4-Chlorophenyl)-4-hydroxypiperidin-1-yl)-2,2-diphenylbutanenitrile (Compound 1)

The synthesis of compound 1 was accomplished by a new route in two steps from commercially available materials. Briefly, the amide precursor (4-(4-(4-chlorophenyl)-4-hydroxypiperidin-1-yl)-2,2-diphenylbutanenitrile; compound 1 in the scheme above) was obtained in 69% yield by alkylation of 4-(4-chlorophenyl)-4-hydroxylpiperidine with 4-bromo-2,2-diphenylbutyronitrile in the presence of DIPEA (diisopropylethyl amine; 2 eq.) in MeCN at 70° C. for 31 hours.

Specifically, 4-(4-Chlorophenyl)-4-hydroxypiperidine (2.12 g, 10.0 mmol) was suspended in acetonitrile (15 mL) and DIPEA (3.5 mL, 30 mmol) was added. 4-Bromo-2,2-diphenylbutyronitrile (3.00 g, 10.0 mmol) in acetonitrile (15 mL) was then added. The reaction mixture was stirred under argon at 70° C. for 31 h. After concentration under vacuum, the crude material was re-dissolved in dichloromethane and introduced onto a silica gel column. The product was eluted with ammonium hydroxide solution (2 M) in MeOH:CH$_2$Cl$_2$ (6:94 v/v) to yield compound 1 as a pale orange solid (3.10 g, 7.21 mmol, 69% yield). M.p. 108-109° C. (n=3). TLC (silica gel; CH$_2$Cl$_2$:2 M NH$_4$OH in MeOH (95:5 v/v); R$_f$=0.60. $^1$H NMR (CDCl$_3$): δ 7.36 (m, 14H), 2.76 (d, J=11.20 Hz, 2H), 2.65 (m, 4H), 2.48 (t, J=6.9 Hz, 2H), 2.08 (t, J=12.5 Hz, 2H), 1.68 (d, J=11.58 Hz, 2H), 1.60 (br s, 1H). $^{13}$C NMR (CDCl$_3$): δ 140.16, 132.95, 129.09, 128.57, 128.10, 126.95, 126.23, 122.27, 71.11, 54.93, 50.17, 49.71, 38.52, 36.80. LC-MS (M$^+$+1)=431.2. HRMS (M$^+$+1): found 431.1895; calc'd for C$_{27}$H$_{27}$ClN$_2$O, 431.1890. LC: 99.89%.

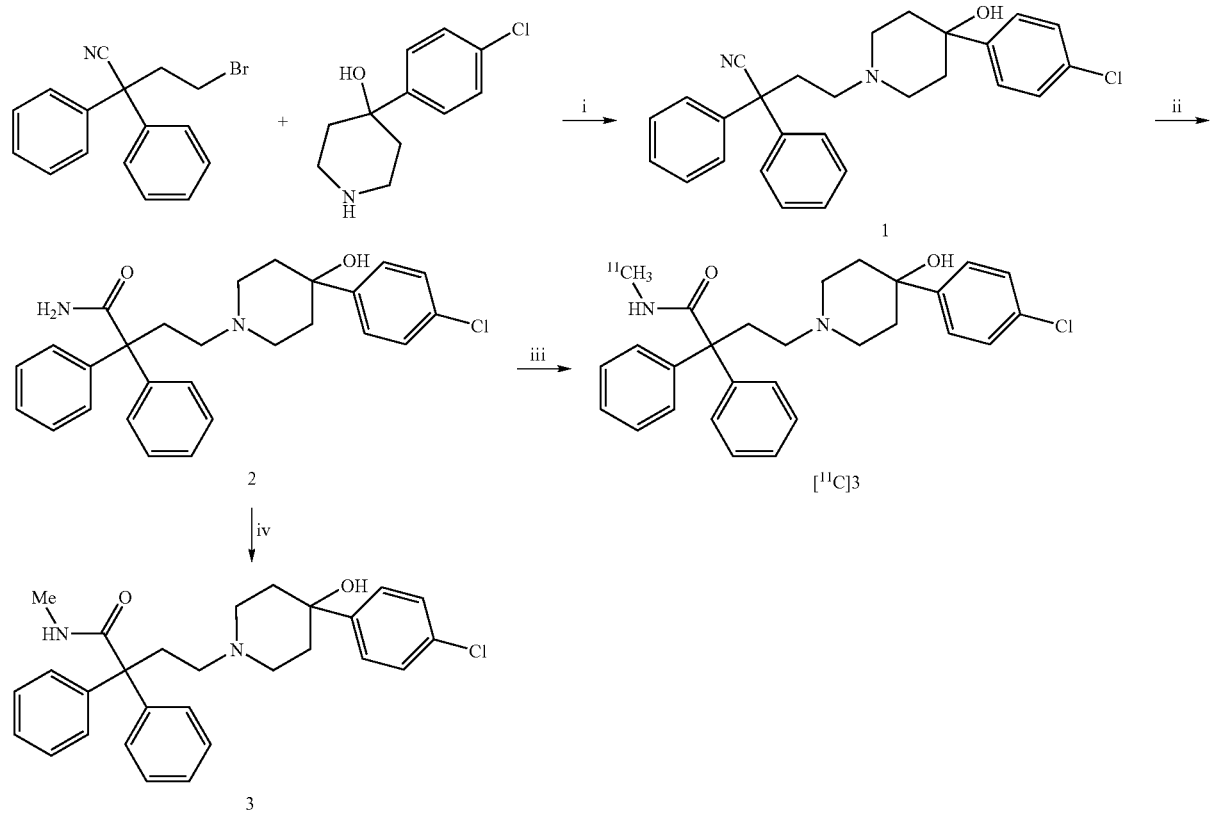

Reaction ii: 4-(4-(4-Chlorophenyl)-4-hydroxypiperidin-1-yl)-2,2-diphenylbutanamide (Compound 2)

Slow hydrolysis of the alkylation product (compound 1) with KOH in t-BuOH at 100° C. for 2-3 days gave the required precursor (4-(4-(4-chlorophenyl)-4-hydroxypiperidin-1-yl)-2,2-diphenylbutanamide; compound 2 in the scheme above) in about 37% yield. Intermediate nitrile and amide precursor were characterized by spectroscopic techniques including $^1$H and $^{13}$C NMR, and LC-MS.

Specifically, compound 1 (2.50 g, 6.00 mmol) was dissolved in t-butanol (20 mL) and potassium hydroxide (1.18 g, 21.0 mmol) was added. The reaction mixture was stirred at 100° C. for 3 days. After concentration under vacuum, the crude material was re-dissolved in dichloromethane and filtered through a pad of celite. Chromatography of the sample on a silica gel column eluted with ammonium hydroxide (2 M) solution in MeOH:$CH_2Cl_2$ (5:95 v/v) gave compound 2 as a pale yellow solid (1.09 g, 2.4 mmol, 37% yield). M.p.=208-210° C. (n=3). TLC (silica gel; $CH_2Cl_2$:2 M $NH_4OH$ in MeOH (95:5 v/v); $R_f$=0.45. $^1$H NMR ($CDCl_3$): δ 7.35 (d, J=4.80 Hz, 2 H), 7.26 (m, 12H), 6.49 (s, 1H), 5.51 (s, 1H), 2.77 (d, J=11.37 Hz, 2H), 2.61 (t, J=7.67 Hz, 2H), 2.33 (m, 4H), 2.03 (t, J=12.64 Hz, 2H), 1.70 (br s, 1H), 1.64 (d, J=11.91 Hz, 2H). $^{13}$C NMR ($CDCl_3$): δ 176.56, 143.26, 132.82, 128.69, 128.41, 127.06, 126.10, 70.90, 59.91, 54.92, 49.48, 38.28, 35.87. LC-MS ($M^+$+1) 449.2.

HRMS ($M^+$+1) found 449.2012; calc'd for $C_{27}H_{30}ClN_2O_2$ 449.1996. LC: 99.90%.

Slow hydrolysis of compound 1 to compound 2 with potassium hydroxide in t-butanol proved to be a key step; attempts to achieve this step with a multitude of other reagents were unsuccessful.

Reaction iii: Preparation of [$^{11}$C] 4-(4-(4-Chlorophenyl)-4-hydroxypiperidin-1-yl)-2,2-diphenyl-N-methyl-butanamide (Compound [$^{11}$C]3)

[$^{11}$C]N-Desmethyl-loperamide ([$^{11}$C] 4-(4-(4-chlorophenyl)-4-hydroxypiperidin-1-yl)-2,2-diphenyl-N-methyl-butanamide; shown as [$^{11}$C]3 in the scheme above) was prepared, ready for intravenous injection, from compound 2 in 18±2% (n=20) isolated decay-corrected radiochemical yield from cyclotron-produced [$^{11}$C]carbon dioxide.

Specifically, [$^{11}$C]iodomethane was prepared as follows: No-carrier-added [$^{11}$C]carbon dioxide (~38 GBq) was produced in a target of nitrogen gas (~164 psi) containing oxygen (1%) via the $^{14}$N(p,α)$^{11}$C reaction induced for 20 min with a 16 MeV proton beam (45 μA) from a PETrace cyclotron (GE; Milwaukee, Wis.). [$^{11}$C]Iodomethane was produced within a lead-shielded hot-cell from the [$^{11}$C]carbon dioxide via reduction to [$^{11}$C]methane and iodination within a MeI MicroLab apparatus (GE).

Specifically, [$^{11}$C]dLop was prepared as follows: radiochemistry was performed in a PLC-controlled semi-robotic Synthia apparatus (Synthia, Uppsala, Sweden), housed within the same lead-shielded hot-cell used to prepare [$^{11}$C] iodomethane. [$^{11}$C]Iodomethane in carrier helium (15 mL/min) was bubbled into a sealed 1 mL-vial containing compound 2 (1.0 mg, 2.23 μmol) and KOH (5.0 mg, 89.3 μmol) in DMSO (0.4 mL). When the radioactivity in the vial had maximized, the reaction mixture was heated at 80° C. for 5 min and then diluted with water (500 μL). The crude material was injected onto a Gemini C18 column (5 μm, 10×250 mm; Phenomenex) eluted at 6 mL/min with ammonium hydroxide solution (2 M) in MeOH:$CH_2Cl_2$ (62:38 v/v). Eluate was monitored for radioactivity (pin diode detector HC-003; Bioscan) and absorbance at 225 nm (Gold 166 detector; Beckman). [$^{11}$C]dLop ($t_R$=10.2 min) eluted after compound 2 ($t_R$=8.71 min) and was collected in a 10-mL round-bottom vial containing an aqueous solution (0.1 ml) of ascorbic acid (1 mg; USP grade). This was then rotary evaporated to dryness, diluted with sterile Saline for Injection (10 mL; USP grade), and filtered through a sterile filter (Millex MP, Millipore, Bedford, Mass.). The pH of the dose was 4.5.

[$^{11}$C]dLop was analyzed for radiochemical purity on a Luna $C_{18}$ column (5 μm, 10×250 mm; Phenomenex) eluted with 0.1% $CF_3CO_2H$:MeCN (40:60 v/v) at 2.5 mL/min ($t_R$=5.55 min), with eluate monitored for absorbance at 225 nm (Gold 166 detector, Beckman) and radioactivity (HC-003 pin diode detector; Beioscan) The identity of [$^{11}$C]dLop was confirmed by (i) LC-MS-MS of associated carrier, and (ii) observation of co-elution with added authentic dLop in a second radio-HPLC analysis.

Figure 6:
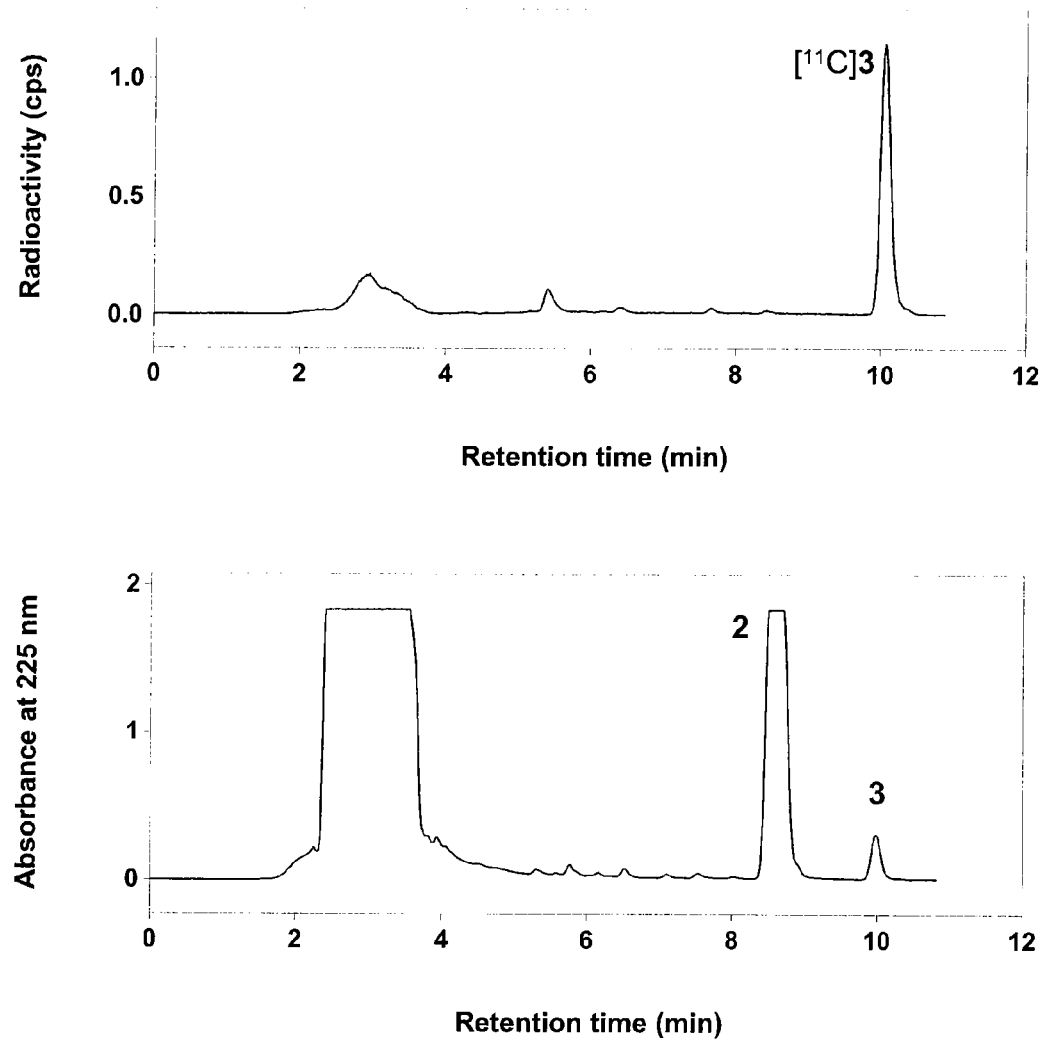
FIG. 6 depicts chromatograms from the HPLC separation of compound [$^{11}$C]dLop, ([$^{11}$C]3 in Figure). Details are described in Example 9.

The radiosynthesis required about 40 min. The obtained activity of [$^{11}$C]dLop averaged 1.9±0.8 GBq. Specific radioactivity, decay-corrected to the end of synthesis, averaged 152±48 GBq/μmol. Radiochemical purity exceeded 99% and the product was radiochemically stable for at least 1 h (by radio-HPLC analysis). [$^{11}$C]dLop was well separated with HPLC from precursor 2 and other impurities (FIG. 6). Thus, chemical impurities were low (and estimated as <1 nmol per batch, assuming that the impurities have the same extinction coefficient at 225 nm in the radio-HPLC analysis).

Purification by reverse phase HPLC gave [$^{11}$C]dLop in high radiochemical and chemical purity, and high specific activity. [$^{11}$C]N-Desmethyl-loperamide was radiochemically stable and readily formulated for intravenous injection. Formulated radiotracer was obtained in a radiosynthesis time of 35 min from the end of radionuclide production in up to 32% decay-corrected radiochemical yield with a specific activity of 3-3.5 Ci/μmol.

Thus, [$^{11}$C]dLop has been prepared effectively for use in imaging P-gp function and methods of the present invention as further described herein.

Reaction iv: 4-(4-(4-Chlorophenyl)-4-hydroxypiperidin-1-yl)-2,2-diphenyl-N-methyl-butanamide (Compound 3)

Methylation of compound 2 with iodomethane in the presence of KOH and DMSO at 80° C. for 24 hours resulted in compound 3 (4-(4-(4-chlorophenyl)-4-hydroxypiperidin-1-yl)-2,2-diphenyl-N-methyl-butanamide). The yield was low (about 3%), but adequate amounts were obtained to serve as a chromatographic reference material.

Specifically, compound 2 (0.5 g, 1.12 mmol) was dissolved in DMSO (3 mL) at 24° C. and potassium hydroxide (81.2 mg, 1.45 mmol) was added. The reaction was stirred at 80° C. for 24 h. The crude material was injected onto a Luna $C_{18}$ column (10 μm, 10×250 mm; Phenomenex, Torrance, Calif.) eluted at 8 mL/min with $CF_3CO_2H$(0.1%):MeCN (72:28 v/v). The collected fractions were then concentrated under vacuum and re-purified on a silica gel rotor (Chromatotron, Model 7924T, Harrison Research, Calif.) eluted with ammonium hydroxide solution (2 M) in MeOH:$CH_2Cl_2$ (5:95 v/v) to yield compound 3 as a pale yellow solid (16.5 mg, 0.036 mmol, 3.2% yield). M.p.=224-226° C. (n=3). TLC (silica gel; $CH_2Cl_2$:2M $NH_4OH$ in MeOH (95:5 v/v); $R_f$=0.45. $^1$H NMR ($CDCl_3$): δ 7.43 (d, J=9.2 Hz, 2 H), 7.30 (m, 12H), 6.62 (s, 1H), 2.80 (d, J=4.8 Hz, 3H), 2.66 (t, J=7.2 Hz, 2H), 2.39 (m, 4H), 2.08 (t, J=11.1 Hz, 2H), 1.72 (d, J=11.6 Hz, 2H), 1.60 (d, J=21.2 Hz, 2H). $^{13}$C NMR ($CDCl_3$): δ 174.79, 143.76, 132.79, 128.77, 128.42, 128.34, 126.91, 126.09, 70.96, 60.10, 58.47, 55.08, 49.50, 26.68. LC-MS, ($M^+$+1) 463.2. HRMS, found ($M^+$+1) 463.2144, calc'd for $C_{28}H_{32}ClN_2O_2$, 463.2152. LC: 99.90%.

Example 10

Pharmacological Screen of Compound 3, N-Desmethyl-Loperamide (dLop)

Loperamide has high affinity for μ-opiate receptors (Stahl, 1977, *Eur J Pharmacol* 46:199-205). [$^{11}$C]dLop was submitted to the National Institute of Mental Health Psychoactive Drug Screening Program (NIMH-PDSP) for assessment of binding affinity against a wide range of receptors and transporters (5-HT$_{1A,1B,1D,1E,2A-C,3,5A,6,7}$, $\alpha_{1A,2A-2C}$, $\beta_{1,2}$, μ-, κ-, δ-opiate, D$_{1,2,4,5}$, H$_{1-3}$, M$_{1-5}$, and σ$_{1,2}$, and noradrenaline, serotonin and dopamine transporters). Detailed assay protocols are available at the NIMH-PDSP web site.

At 10 μM concentration, [$^{11}$C]dLop was found to cause <50% inhibition of binding to 5-HT$_{1A,1B,1D,1E,2A,2B}$, $\beta_{1,2}$, D$_{1,2,5}$, M$_{1-5}$, κ- and δ-opiate receptors, and to the norepinephrine and dopamine transporters. Greater than 50% inhibition was observed at $\alpha_{1A,2A-C}$, D$_{3,4}$, H$_{1,3}$, μ-opiate and σ$_{1,2}$ receptors and the serotonin transporter. Corresponding K$_i$ values (nM) were $\alpha_{1A}$ (9.9), $\alpha_{2A}$ (1.0), $\alpha_{2B}$ (7.0), $\alpha_{2C}$ (2.4), D$_4$ (1.1), H$_1$ (4.2), H$_2$ (1.72), H$_3$ (9.3), μ-opiate (0.6), σ$_1$ (0.8), σ$_2$ (1.9) and serotonin transporter (6.2).

This pharmacological screen found that [$^{11}$C]dLop had high affinity for μ-opiate receptors (K$_i$=0.56 nM), and also quite high affinity (K$_i$=<10 nM) for $\alpha_{1A,2A-2C}$, D$_4$, H$_{1,3}$, and σ$_{1,2}$ receptors and for the serotonin transporter, but was devoid of high affinity for any of a wide battery of other receptors, transporters and binding sites. This pharmacological profile is similar to that of loperamide itself.

Example 11

PET Imaging of [$^{11}$C]N-Desmethyl-loperamide ([$^{11}$C]dLop) in Mouse Brain In an additional set of in vivo experiments to those described in Example 6, brains of mice were scanned with the Advanced Technology Laboratory Animal Scanner (AT-LAS). This small-animal PET camera has effective transaxial and axial fields of view of 6.0 and 2.0 cm, respectively (Seidel et al., 2003, *IEEE Trans Nucl Sci* 50:1347-1350). Mice were anaesthetized with 1.5% isoflurane in oxygen, and body temperatures maintained between 36.5 and 37.0° C. with a heating pad or lamp. Radiotracer was injected via a polyethylene cannula (PE-10; Becton Dickinson, Franclin Lakes, N.J.) secured in the mouse tail vein with tissue adhesive (Vetbond; 3M, St. Paul, Minn.).

On two occasions, one P-gp knockout mouse (19-23.8 g) and one wild type mouse (28.6-29.5 g) were placed in the camera gantry and each injected with a bolus of [$^{11}$C]dLop (21.1-27.9 MBq; SA 40.7-131 GBq/μmol). The injected radioactivities gave count rates within the linear range of scanner performance i.e. <300,000 singles per s. Scans were obtained from the time of injection for 100 min in the frame sequence 6×20 s, 5×1 min, 4×2 min, 3×5 min, 3×10 min, and 2×20 min. Data were corrected for random events and detector efficiency. Images were reconstructed with a 3D ordered-subset expectation maximization algorithm into 17 coronal slices with 3 iterations and 16 subsets, resulting in a resolution of about 1.6 mm full width at half maximum (Johnson et al., 2002, *Mol Imaging Biol* 4:S22 (abstract); Liow et al., 2003, *J Nucl Med* 44:162P (abstract). The reconstructed voxel size was 0.56×0.56×1.12 mm. No attenuation or scatter correction was applied. Images were analyzed with PMOD (pixel-wise modeling software; PMOD Group; Zurich, Switzerland). A region of interest was drawn for forebrain on coronal slices guided by a mouse brain stereotaxic atlas (Paxinos and Watson, 2001, *The Rat Brain in Stereotaxic Coordinates*, 6th Edition, Amsterdam, Boston, Elsevier). Brain uptake of radioactivity was corrected for decay and normalized for injected dose and body weight by expression as percent standardized uptake value (% SUV), defined as: % SUV=[(activity per g tissue)/injected activity]×g body weight×100.

PET scans of wild type mice administered with [$^{11}$C]dLop alone revealed only very low uptake of radioactivity into forebrain which quickly maximized and then washed out slowly (FIG. 7A). After the injection of [$^{11}$C]dLop into wild type mice, the brain uptake of radioactivity measured with PET reached a very low maximum between 2 and 4 min. These data are consistent with effective exclusion of the radiotracer from brain by P-gp at the blood-brain barrier.

In P-gp knockout mice, maximal brain uptake of radioactivity was higher and occurred between 8 and 20 min. The subsequent decrease in brain radioactivity from all mice was slow. At 30 min after radiotracer injection, forebrain radioactivity concentration was on average 3.7 fold higher in forebrain of P-gp knockout mice than of wild type mice (FIGS. 7A, 7B). Cerebellum gave similar results (data not shown). These results provide direct evidence that [$^{11}$C]dLop is a substrate for P-gp.

Example 12

Figure 7:
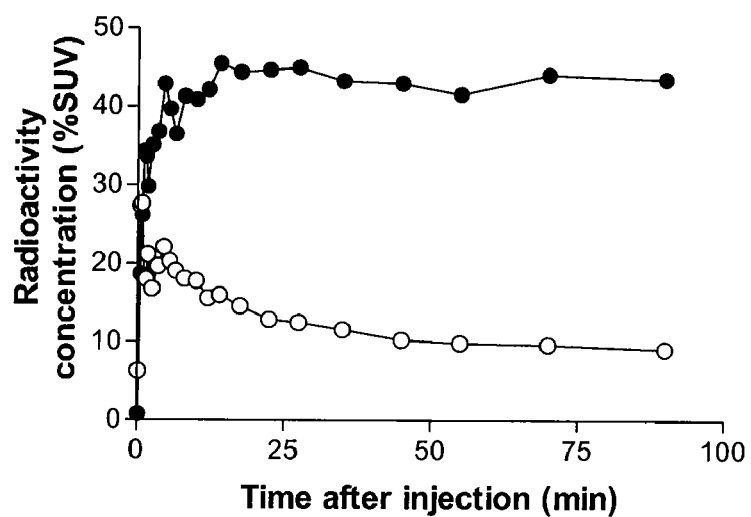
FIG. 7 depicts representative time-activity curves in forebrain of wild-type and P-gp knockout mouse measured with PET after the intravenous administration of compound [$^{11}$C]dLop. Key: wild type (○); knockout (●). Details are described in Example 12.

Measurement of [$^{11}$C]N-Desmethyl-loperamide ([$^{11}$C]dLop) and Radiometabolites in Mouse Brain and Plasma PET scans are unable to identify the chemical species being measured in the brain. Moreover, they are subject to partial volume effects due to the limited spatial resolution of the PET camera. In the above Example 12, the spatial resolution was ~1.6 mm full-width at half maximum; therefore small regions of mouse brain that contained relatively high levels of radioactivity would not be measured accurately. They would be underestimated while any neighboring regions of low activity would be overestimated. In order to measure radioactivity concentration in brain and plasma more accurately analytical measurements were made ex vivo at a single time point with a γ counter. The time chosen for these measurements was 30 min after [$^{11}$C]dLop injection, since the PET scans had already shown little loss of activity from brain over the preceding time span (FIG. 7). Radio-HPLC of brain tissue (FIG. 8) or plasma was also used to separate and measure unchanged radiotracer and its radiometabolites.

Thirty minutes after injection of [$^{11}$C]dLop into each of three wild type and three knockout mice, anti-coagulated blood (1 mL) was sampled by cardiac puncture. Plasma (~100-450 μL) was separated by centrifugation, deproteinized with acetonitrile (700 μL) and measured for radioactivity in an automatic γ-counter (Zoghbi et al., 2006, *J Nucl Med* 47:520-527). The animals were decapitated, and forebrains and cerebella removed for immediate radioanalysis (Zoghbi et al., 2006, *J Nucl Med* 47:520-527). Brain-tissue radioactivities were measured in the γ-counter. Brain tissue suspension, along with carrier compound 3, was homogenized in 1.5 times its volume of acetonitrile with a hand-held tissue Tearor (model 985-370; BioSpec Products Inc.). Water (500 μL) was added and the mixture homogenized again. Homogenates were then centrifuged at 10,000 g for 1 min. The resulting precipitates and supernatant liquids were measured for radioactivity to allow the recovery of activity into the acetonitrile supernatants to be calculated. Aliquots of the clear pre-filtered supernatant liquids were analyzed by radio-HPLC (see herein).

Recoveries of radioactivity from brain tissue and plasma into acetonitrile were between 87.0 and 97.1% (92.5±2.9%, n=18). Radioactive analytes were fully recovered from the HPLC column.

At 30 min after the administration of [$^{11}$C]dLop, the radioactivity concentrations found in plasma were low and very similar between knockout and wild type mice (Table 4). By contrast, radioactivity concentrations in the forebrains of knockout mice were more than 7 fold higher, than the very low concentrations found in wild type mice (Table 4).

TABLE 4

Radioactivity content in brain tissue and plasma and its distribution at 30 min after administration of [$^{11}$C]dLop to wild type and P-gp knockout mice. Values are mean ±SD (n = 3).

| Mice | Tissue | Total Radioactivity (% SUV) | Radioactivity distribution (%) | | | |
|---|---|---|---|---|---|---|
| | | | [$^{11}$C]dLop | [$^{11}$C]A | [$^{11}$C]B | [$^{11}$C]C |
| WT | Cerebellum | 5.6 | 45.5 ± 6.7 | 42.4 ± 2.4 | 8.2 ± 5.0 | 3.9 ± 2.1 |
| | Forebrain | 5.4 | 43.6 ± 5.5 | 41.4 ± 3.3 | 11.7 ± 2.4 | 3.3 ± 0.5 |
| | Plasma | 25.3 | 11.1 ± 0.7 | 67.5 ± 13.2 | 20.9 ± 13.6 | 0.5 ± 0.3 |
| KO | Cerebellum | 44.4 | 88.9 ± 4.2 | 3.5 ± 0.9 | 1.2 ± 0.7 | 6.4 ± 3.1 |
| | Forebrain | 38.9 | 91.3 ± 3.6 | 3.6 ± 1.9 | 0.8 ± 0.5 | 4.3 ± 2.3 |
| | Plasma | 22.1 | 7.9 ± 1.6 | 58.0 ± 27.5 | 33.7 ± 29.3 | 0.3 ± 0.2 |

Figure 8:
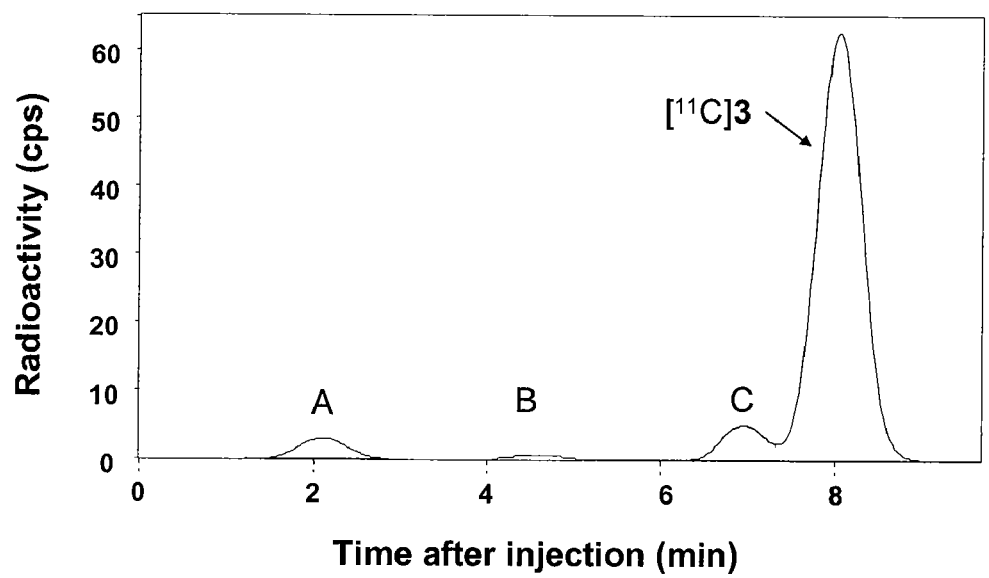
FIG. 8 depicts a radiochromatogram of radioactive species in P-gp knockout mouse forebrain at 30 min after the administration of [$^{11}$C]dLop ([$^{11}$C]3). Compound [$^{11}$C]dLop and radiometabolites [$^{11}$C]A, [$^{11}$C]B, and [$^{11}$C]C are indicated by [$^{11}$C]3, A, B, and C, respectively. See Examples 1 and 13 for chromatographic conditions and details.

Radio-HPLC of wild type or P-gp knockout plasma showed that a proportion of radioactivity consisted of radiometabolites, all of which were less lipophilic than parent radiotracer, [$^{11}$C]dLop. Three radiometabolites ([$^{11}$C]A-[$^{11}$C]C) were detected in mice plasma and brain tissue samples at 30 min after radiotracer injection (FIG. 8). Measurements in wild type and knockout mice gave very similar values for total radioactivity concentration in plasma and for the distribution of this radioactivity between radiotracer and radiometabolites. The concentrations of unchanged [$^{11}$C]dLop in plasma were on average very low and similar between wild type mice (2.8% SUV) and knockout mice (1.7% SUV) (Table 4). This was also true for the three metabolites.

Measurements on brain tissue confirmed the higher radioactivity content in the knockout mice. On average, [$^{11}$C]dLop was 43.6% of radioactivity in forebrains of wild type mice, while in the knockout mice this value increased to 91.3%. The ratio of radioactivity in knockout mice forebrain to that in wild type mice was seven, compared to the values of (~3.6-3.7) seen between 27.5 and 35 min in the PET experiments. The PET ratio is therefore in appreciable error.

Blood constitutes 4-5% of brain volume. The PET scans are uncorrected for blood radioactivity while the ex vivo measures do not include significant blood radioactivity. In this case, blood radioactivity was not a major source of error in the PET measurements because the blood levels of radioactivity were only about five-fold higher than in brain (in wild type mice) or appreciably lower (in knockout mice) (Table 4)

The several-fold higher uptake of radioactivity in the forebrains of knockout mice compared to those of wild type is predominantly explained by the greatly increased uptake of unchanged [$^{11}$C]dLop. The uptake of [$^{11}$C]dLop was about 16-fold higher in forebrains of knockout mice than in wild type mice (Table 4). As a result, about 90% of the radioactivity in knockout mouse brain is unchanged [$^{11}$C]dLop (Table 4). This result, obtained in a generally highly metabolic species, augers well for the potential to quantify brain P-gp function with PET and [$^{11}$C]dLop in rodents and higher species, including humans. By contrast, only ~50% of the radioactivity in P-gp knockout mouse brain after the administration of [$^{11}$C]loperamide was unchanged radiotracer, so precluding prospects for its use to quantify P-gp function. Hence, on the basis of these data, [$^{11}$C]dLop is a vastly better radiotracer than [$^{11}$C] loperamide.

In knockout mice, [$^{11}$C]C was the most prevalent radiometabolite in brain, despite its very low presence in plasma (FIG. 8, Table 4). Although this radiometabolite was 8-fold higher in concentration in the forebrains of knockout mice than of wild type mice, the absolute concentrations in knockout mice were very low compared to that of [$^{11}$C]dLop. The more polar radiometabolites, [$^{11}$C]A and [$^{11}$C]B, showed no higher uptake in knockout mice than in wild type mice (FIG. 8, Table 4).

The ratios of [$^{11}$C]dLop concentration in forebrain to that in plasma were close to unity for wild type mice but increased to over twenty for knockout mice (Table 4). Finally, the concentrations of [$^{11}$C]dLop and of the radiometabolites, [$^{11}$C] A-C, in cerebellum were very similar to those of forebrain in both wild type and knockout mice (data not shown)

Example 13

PET Imaging of [$^{11}$C]N-Desmethyl-loperamide ([$^{11}$C]dLop) in Monkey Brain Encouraged by the data obtained in mice, PET experiments in monkeys (similar to those described in Example 5) were pursued in which DCPQ at doses equal to or greater than 8 mg/kg i.v. could be used to block brain P-gp function. Structurally, DCPQ is very closely related to zosuquidar (LY335979), which shows selectivity for P-gp versus other efflux transporters, such as MRP1, MRP2, MRP3 or BCR.

The formulas of DCPQ (Formula XIII) and zosuquidar (Formula XIV) are shown below:

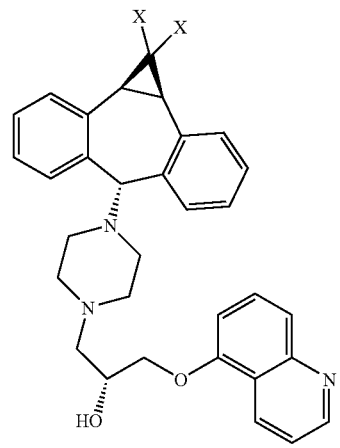

X = Cl, DCPQ
X = F, Zosuquidar

One male rhesus monkey (A; 8.4 kg) was fasted overnight, immobilized with ketamine (10 mg/kg, i.m.), intubated, placed on a ventilator, and anesthetized with 1.6% isoflurane in $O_2$. Body temperature was maintained between 36.5 and 37.0° C. After injecting compound [$^{11}$C]3 (211 MBq in 10 mL) through an intravenous perfusion line, filled with saline, dynamic PET scans of the brain were acquired on an HRRT camera (Siemens, Knoxville, Tenn.) for 120 min in 33 frames of duration increasing from 30 s to 5 min. Images were reconstructed using filtered back-projection in list mode 3D-OSEM algorithm (Carson et al., 2003, *Conference Record of the IEEE Nuclear Science Symposium and Medical Imaging Conference*; Portland, Oreg.), resulting in a resolution of 2.5 mm full-width at half maximum. Scatter and attenuation correction were applied. Images were analyzed with PMOD. Regions of interest were drawn on coronal slices for eight brain regions (frontal cortex, anterior cingulate, temporal cortex, parietal cortex, hippocampus, occipital cortex, putamen and cerebellum). Activity was decay-corrected to the time of injection and expressed as % SUV.

Three hours after the baseline scan, P-gp was blocked with DPCQ (8 mg/kg. i.v.) in the same monkey and the PET scanning repeated. For this purpose, DPCQ (67.3 mg, 0.120 mmol) was dissolved with the aid of sonication in sterile aqueous mannitol (5% w/v; 10 mL), diluted with sterile saline (10 mL) and finally passed through a sterile filter (Anatop 25; 0.2 μm, 25 mm; Whatman). This DCPQ solution (3.36 mg/mL; 19.76 mL) was infused into the monkey over 10 min. After 20 min the monkey was injected with [$^{11}$C]dLop (218 MBq).

Experiments were similarly performed in a single monkey (monkey B; 15.5 kg) to assess the effect of DCPQ at doses of 0, 4, 8 and 16 mg/kg (i.v.) on regional brain radioactivity uptake after the administration of [$^{11}$C]dLop. Time-radioactivity data were collected for the same eight brain regions as previously described. Injected activities in this series of experiments were 377, 340, 281 and 355 MBq, at specific activities of 160, 94.5, 131 and 183 GBq/μmol, respectively.

The baseline and P-gp blocked experiments were repeated in a third monkey (C; 12.45 kg) with naloxone (5 mg, i.v.) administered at 30 min after the second injection of [$^{11}$C] dLop and in another monkey (D; 15.72 kg) in which the dose of DCPQ was increased to 16 mg/kg (i.v.) and the naloxone was given as before. Injected activities in this sequence of experiments were 313, 283, 377, and 355 MBq, respectively.

A PET experiment was performed in monkey E (11.1 kg) in which P-gp was blocked with DCPQ (8 mg/kg, i.v.) as before and in which loperamide (1 mg/kg, i.v) was also given at 30 min after [$^{11}$C]dLop (315 MBq). Finally, This experiment was repeated in monkey F (9.5 kg), except that 3 (1 mg/kg, i.v.) was given instead of loperamide before administration of [$^{11}$C]dLop(370 MBq). This scan was terminated at 45 min.

After intravenous injection of [$^{11}$C]dLop into monkey under baseline conditions, the maximal uptake of radioactivity into brain regions was low but well retained (FIG. 9A). By contrast uptake of radioactivity into the pituitary was high. Temporal cortex showed highest uptake and cerebellum lowest (data for other cortical regions were intermediate and are not shown).

In the experiment in the same monkey in which DCPQ (8 mg/kg) was administered intravenously before [$^{11}$C]dLop, radioactivity uptake into all brain regions increased dramatically, while the uptake into pituitary was very similar to that in the baseline experiment (FIGS. 9A and 9B). In the experiment in which DCPQ had been pre-administered at a dose of 8 mg/kg to pre-block P-gp, radioactivity uptake reached a maximum within 30 min (FIG. 9B) Brain uptake of radioactivity varied regionally with putamen showing highest uptake and frontal cortex showing lowest. In this experiment, the ratio of maximal brain radioactivity to that in the baseline experiment was about five.

In both baseline and P-gp blocked experiments the uptake of radioactivity in the pituitary outside the blood-brain barrier was very high and similar (FIGS. 9A and 9B).

Figure 10:
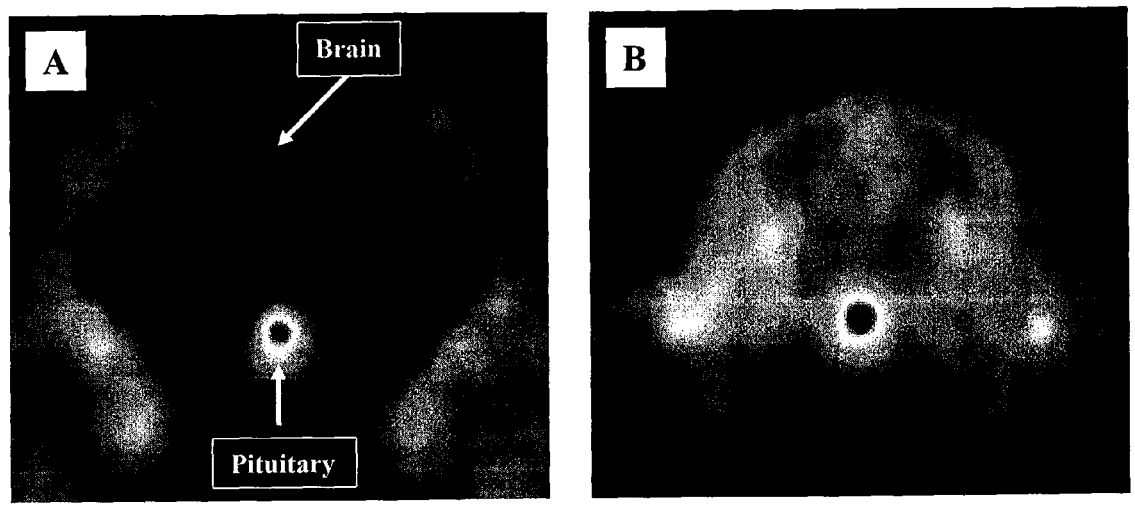
FIG. 10 depicts transaxial PET images obtained between 20 to 120 min after the intravenous administration of [$^{11}$C] dLop to monkey under baseline conditions (Panel A) and after P-gp inhibition with DCPQ (8 mg/kg, i.v.) (Panel B). Details are described in Example 14.

PET images of the brain and pituitary under baseline and P-gp blocked conditions dramatically portrayed these patterns (FIG. 10). PET images of monkey brain, obtained by summing data acquired between 20 and 90 min after intravenous injection of [$^{11}$C]dLop under baseline condition, confirmed uniformly very low uptake of radioactivity into brain (dark area in FIG. 10A), and very high uptake into pituitary (light area indicated by arrow in FIG. 10A). By contrast, radioactivity was taken up into all brain areas in the corresponding pre-block experiment, and also seen again in pituitary (compare FIGS. 5A and 5B). These data are consistent with [$^{11}$C]dLop behaving as a substrate for P-gp at the blood-brain barrier, but not at the pituitary which partially lies outside the blood-brain barrier.

Figure 20:
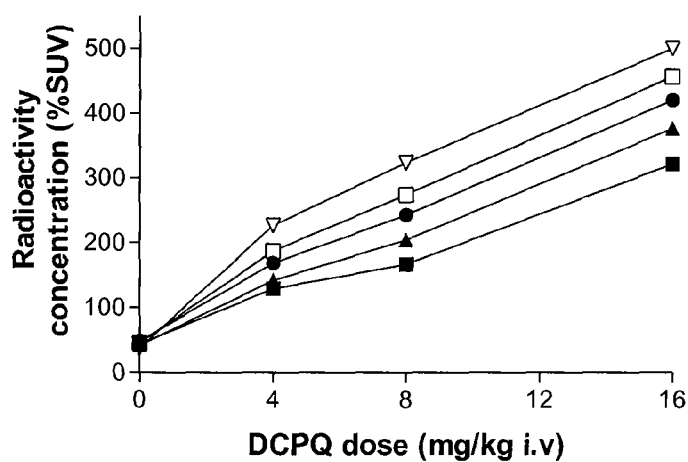
FIG. 20 depicts regional brain uptake of radioactivity after administration of [$^{11}$C]dLop—dependence on pre-administered dose of DCPQ. Key: frontal cortex (■); anterior cingulated (▲), hippocampus (●), occipital cortex (□), and cerebellum (▽). Temporal cortex, parietal cortex and putamen gave intermediate curves, but are not shown for figure clarity. Details are described in Example 13.

Regional brain uptakes of radioactivity after intravenous administration of [$^{11}$C]dLop, subsequent to various doses of DCPQ (0-16 mg/kg, i.v.) were measured in one monkey and increased almost linearly with dose of DCPQ (FIG. 20) Specifically, in experiments in a single monkey, in which the dose of DCPQ administered before [$^{11}$C]dLop was varied between 0 and 16 mg/kg, i.v., radioactivity uptake, averaged between 25 and 50 min, increased almost linearly with dose of DCPQ across all inspected brain regions (FIG. 20). Regional variation was considerable. Brain uptake of radioactivity varied regionally but quite consistently across doses of DCPQ. At the highest dose of DCPQ, regional radioactivity concentrations increased between seven-fold (in frontal cortex) and thirteen-fold (in cerebellum) relative to baseline values. This strongly indicates that [$^{11}$C]dLop has sensitivity to the degree of blockade of brain P-gp.

Figure 9:
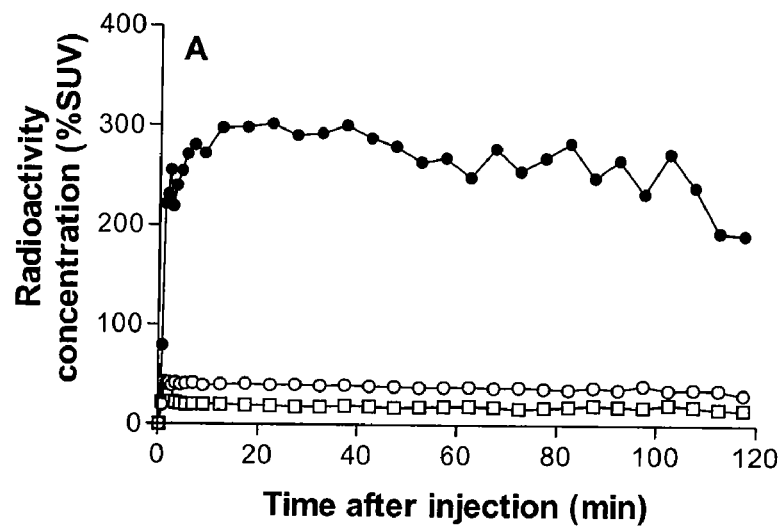
FIG. 9 depicts the regional uptake of radioactivity in monkey brain after the administration of [$^{11}$C]dLop under baseline conditions (Panel A), and at 30 min after the administration of DCPQ (8 mg/kg, i.v.) (Panel B). Key: frontal cortex (∇), temporal cortex (○), parietal cortex (◇), putamen (x), cerebellum (□) and pituitary (●). Details are described in Example 14.
Figure 9:
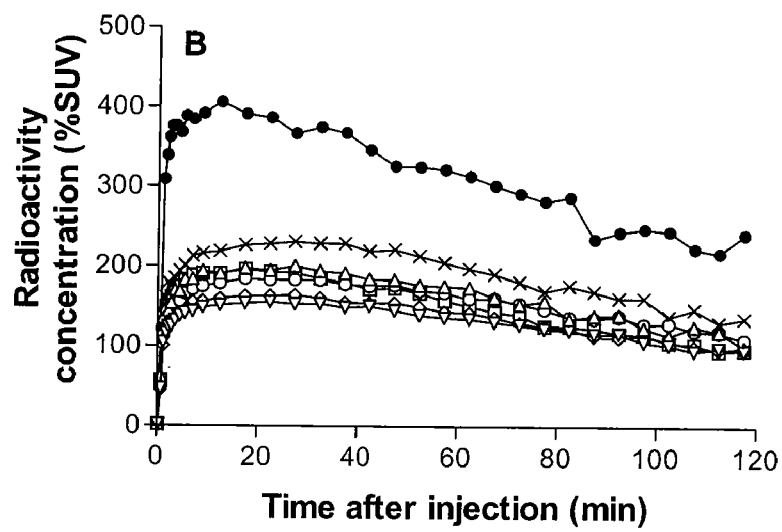

The time-activity curves under baseline and P-gp blocked conditions were characterized by fast initial uptake of radioactivity and then strong retention of radioactivity (FIG. 9). In addition, some regions like cerebellum consistently showed higher uptake than others (e.g., frontal cortex) at all doses of DCPQ (FIGS. 9B and 20). This variability may have been caused by regional differences in blood flow or in P-gp activity itself.

Figure 11:
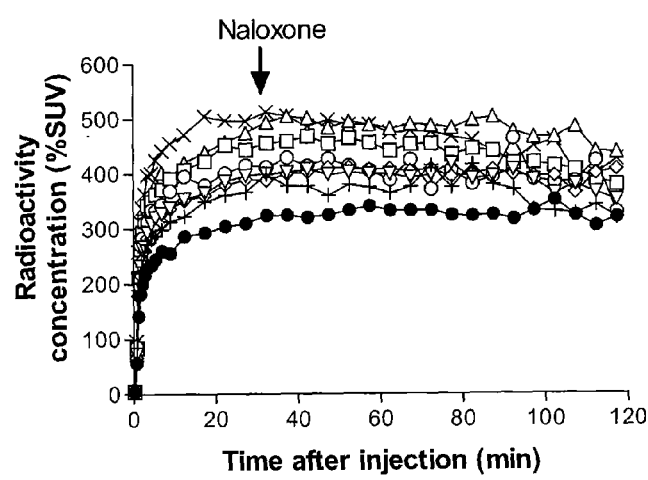
FIG. 11 depicts uptake of radioactivity into monkey brain regions after administration of [$^{11}$C]dLop at 30 min after administration of DCPQ (16 mg/kg), with naloxone (5 mg/kg, i.v.) given at 30 min after radioligand injection. Key: frontal cortex (●), anterior cingulate (+), temporal cortex (∇), parietal cortex (◇), hippocampus (*), occipital cortex (□), putamen (Δ) and cerebellum (x). Details are described in Example 14.
Figure 12:
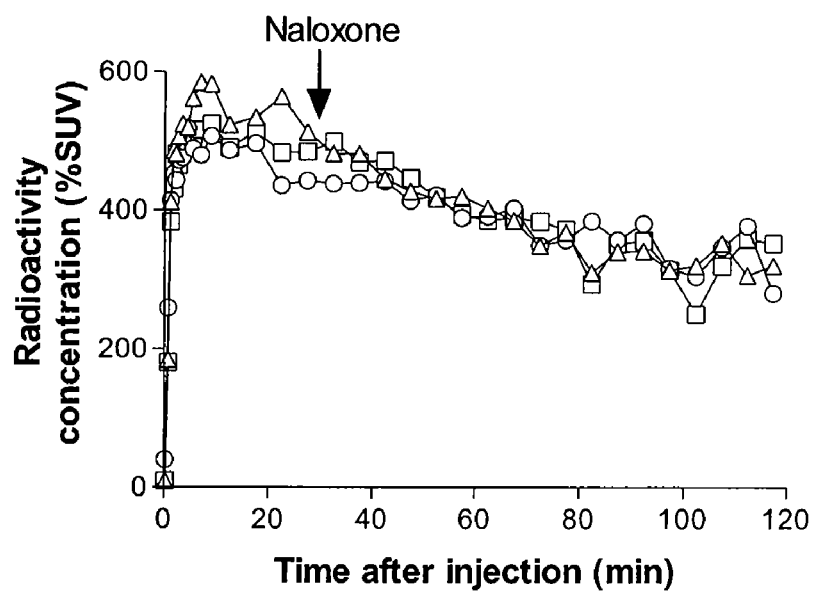
FIG. 12 depicts pituitary uptake of radioactivity after intravenous administration of [$^{11}$C]dLop to monkey under baseline conditions (○), under conditions in which P-gp was inhibited with DCPQ (8 mg/kg i.v.) with naloxone (5 mg/kg, i.v.) given at 30 min after radiotracer (□), and under conditions in which P-gp is inhibited with DCPQ (16 mg/kg, i.v.) with the naloxone given as before (Δ). Details are described in Example 14.

In the PET experiment in which P-gp was inhibited with DCPQ, and [$^{11}$C]dLop ([$^{11}$C]3) was added 20 thereafter, followed by administration of the opiate receptor antagonist, naloxone, 30 min after injection of [$^{11}$C]dLop, again high early uptake of radioactivity in all examined brain regions was observed. By visual inspection, naloxone had no effect on the rate of washout of radioactivity from these brain regions (c.f. FIG. 11 with FIG. 9B). The uptake of radioactivity into pituitary was unaffected by administration of DCPQ at either 8 mg/kg or 16 mg/kg i.v. before injection of [$^{11}$C]dLop (FIG. 12). Moreover, the administration of naloxone at 30 min after radiotracer injection had no effect on washout of radioactivity from pituitary compared to that in the baseline experiment (FIG. 12). Administration of either loperamide or dLop at 30 min after [$^{11}$C]dLop in DCPQ-treated monkeys had no discernible effect on the washout of radioactivity from brain (data not shown).

In view of the high affinity shown by dLop for a variety of receptors and the serotonin transporter, it was considered that the strong retention of radioactivity in all brain regions might represent tight binding to one or more of these sites. dLop showed highest affinity for μ-opiate receptors. Naloxone is a high-affinity μ-, κ- and δ-opiate receptor antagonist and has been used to displace PET radioligands, such as [$^{11}$C]diprenorphine (Jones et al., 1988, *J Neurosci Methods* 23:121-129; Shiue et al., 1991, *Nucl Med Biol* 18:281-288), [$^{11}$C]GR103545 (Talbot et al., 2005, *J Nucl Med* 46:484-494) and [$^{11}$C]methylnaltrindole (Mader et al., 2007, *J Nucl Med* 48:207-213), from opiate receptors in monkey and human brain in vivo. Therefore, it was attempted to displace radioactivity in brain with an injection of naloxone at 30 min after the administration of c[$^{11}$C]dLop to a P-gp-inhibited monkey. Naloxane had no discernible effect on the washout of radioactivity from any of the examined brain regions (FIG. 11). Thus, it was conclude that specific binding to opiate receptors was not responsible for the strong retention of radioactivity in brain. Likewise, the nalaxone had effect on washout of radioactivity from pituitary (FIG. 12), even though pituitary is known to contain high levels of opiate receptors. The uptake of radioactivity into pituitary was independent of P-gp inhibition or amount of inhibitor (DCPQ) administered, showing uptake is not influenced by P-gp. We also considered that [$^{11}$C]dLop might have been binding to one of the other sites for which it has high affinity. The lack of displacement of radioactivity from monkey brain by loperamide or dLop showed that [$^{11}$C]dLop does not have saturable receptor binding in monkey brain. Most probably the sustained uptake of radioactivity in brain and pituitary represents non-specific binding to high concentration non-saturable sites, or is perhaps due to some other mechanism (e.g., entrapment by protonation).

Example 14

Emergence of Radiometabolites of [$^{11}$C]N-Desmethyl-loperamide ([$^{11}$C]dLop) in Monkey Plasma After the administration of [$^{11}$C]dLop to monkey (A) under baseline and P-gp blocked condition (achieved with DCPQ at 8 mg/kg, i.v.), eight arterial blood samples (0.5 mL each) were drawn into heparin-treated syringes at 15 s intervals until 2 min, followed by 1 mL aliquots at 3, 5, 10, 20, 30, 45, 60, 75, 90, and (in DCPQ-treated monkey only) 120 min. Samples were measured for radioactivity. Plasma [$^{11}$C]dLop was separated, measured for radioactivity, deproteinized and the [$^{11}$C]dLop and radiometabolite contents quantified with radio-HPLC (Example 1).

Figure 13:
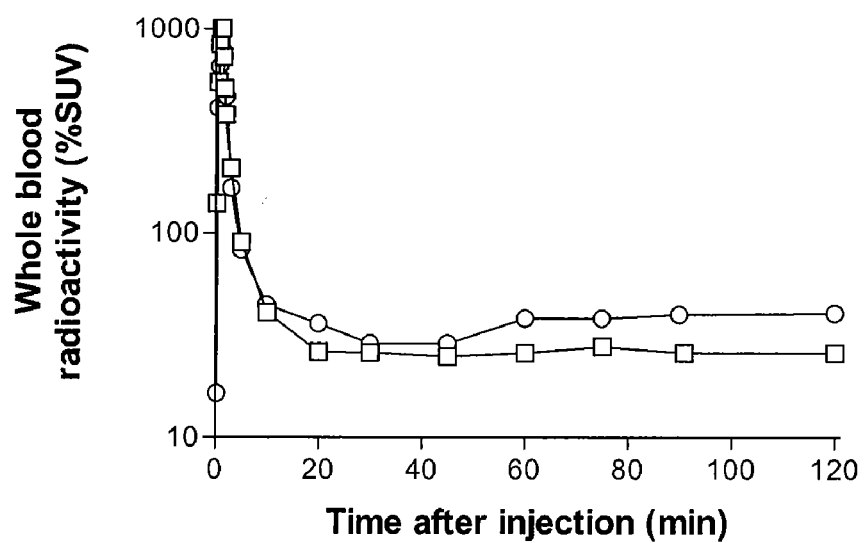
FIG. 13 depicts whole blood radioactivity concentration after administration of [$^{11}$C]dLop to monkey under baseline conditions (□) or at 20 min after administration of DCPQ (8 mg/kg, i.v.) (○). Details are described in Example 15.

After intravenous injection of [$^{11}$C]dLop into monkey under baseline or P-gp blocked conditions, radioactivity concentration in whole blood decreased rapidly and at similar rates from whole blood (FIG. 13), reaching a very low and stable radioactivity level at 20 min. This rate of decrease was unaffected by pre-administration of DCPQ (FIG. 13). Likewise, parent radiotracer concentration in blood decreased fast initially and then continued to decline slowly.

Figure 14:
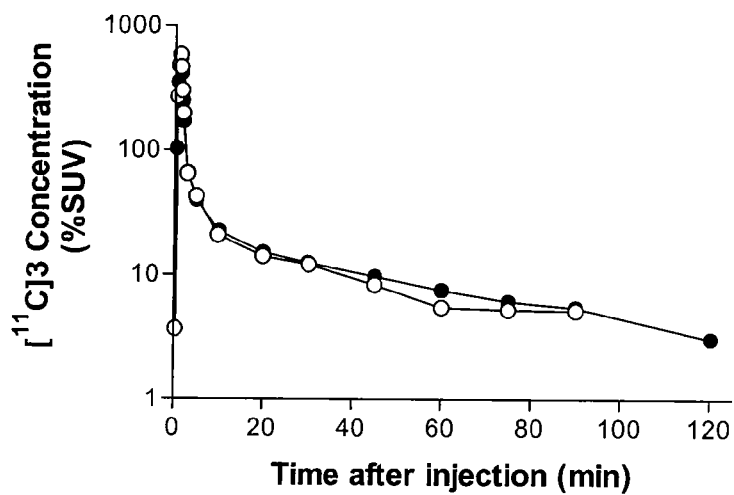
FIG. 14 depicts concentration of unchanged [$^{11}$C]dLop in plasma after administration to monkey under baseline condition (○) and at 20 min after inhibition of P-gp with DCPQ (8 mg/kg, i.v.) (●). Details are described in Example 15.

The recovery of radioactivity from plasma into supernatant acetonitrile for radio-HPLC analysis was efficient; only very low percentages of radioactivity co-precipitated with protein. As in mice, [$^{11}$C]dLop and three less polar radiometabolites were detected in plasma. The concentration of unchanged [$^{11}$C]dLop in plasma decreased to half of its initial value within 2 min, and was unaffected by pre-administration of DCPQ (FIG. 14).

Three radiometabolites were found in monkey blood after administration of [$^{11}$C]dLop. These radiometabolites, [$^{11}$C]A-C, were all less lipophilic than [$^{11}$C]dLop and had similar retention times to those observed in mouse plasma and brain ([$^{11}$C]A-C, $t_R$s=2.1, 4.5 and 6.9, min, respectively; FIG. 8).

Figure 15:
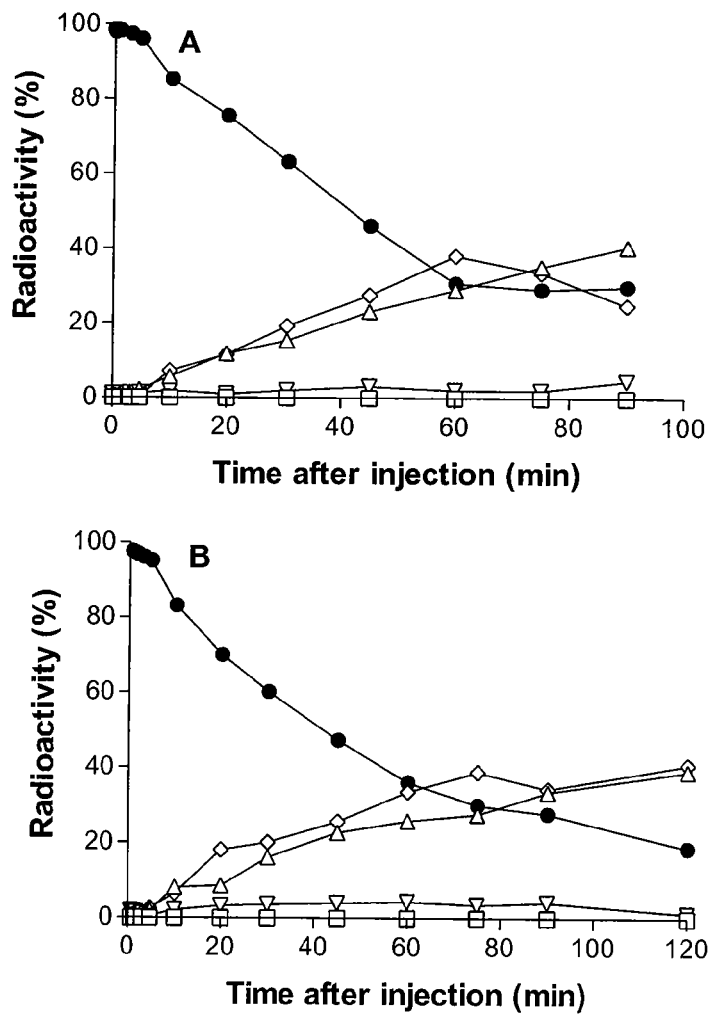
FIG. 15 depicts a time course of composition of radioactivity in plasma after intravenous administration of [$^{11}$C] dLop into monkey under baseline conditions (Panel A) and at 20 min after administration of DCPQ (8 mg/kg, i.v.) (Panel B). Key: compound [$^{11}$C]dLop (●); [$^{11}$C]A (Δ); [$^{11}$C]B (∇); [$^{11}$C]C (◇); unextracted for analysis (□). Details are described in Example 15.

Although not proven, the monkey radiometabolites are likely to be the same radiochemical species as those in mice. The pattern for the emergence of these radiometabolites in monkey plasma was unaffected by DCPQ pre-treatment (FIG. 15). Radiometabolite [$^{11}$C]B only ever became a low percentage of radioactivity in monkey plasma, but radiometabolites [$^{11}$C]A and [$^{11}$C]C gradually increased as a percentage of total radioactivity (FIG. 15). In the baseline and P-gp blocked experiments, the time taken for plasma radiometabolite activity to equal that of [$^{11}$C]dLop was about 45 min which is significantly slower than for [$^{11}$C]loperamide (Zoghbi et al., 2008, *J Nucl Med* 49:649-656). Further, as described in Example 4, [$^{11}$C]loperamide generated significantly more metabolites.

[$^{11}$C]dLop was confirmed to be an avid substrate for brain P-gp in mouse and monkey. Although [$^{11}$C]dLop was metabolized to three less polar radiometabolites, radioactivity uptake into brain was greatly increased under conditions in which P-gp was absent or blocked. In P-gp knockout mouse the vast majority of radioactivity entering brain was unchanged [$^{11}$C]dLop in high ratio to its concentration in plasma. These findings show that [$^{11}$C]dLop is a new radiotracer with favorable properties for quantifying brain P-gp function with PET.

Example 15

[$^{11}$C]Loperamide and Its N-desmethyl Radiometabolites are Avid Substrates for Brain P-Glycoprotein Additional experiments similar to those described in Example 4 were performed. Monkey brain PET scans were obtained with [$^{11}$C]loperamide (~7.2 mCi) on an HRRT camera over 120 min. The baseline scans were followed by one with pre-administration of the P-gp inhibitor, tariquidar (8 mg/kg, i.v.). Arterial plasma parent input function and plasma free fraction ($f_f$) were determined in monkey.

In this set of experiments it was observed that (i) the pharmacological inhibition of P-gp in monkey gave an about 3.7 fold increase of brain activity (from 40 to 146% standard uptake value); (ii) $f_f$ with tariquidar treatment was 12% less than control; (iii) plasma parent area under curve was 21% larger than control; (iv) again, as described above, six radiometabolites were detected in monkey plasma; and (v) parent plasma composition decreased to 50% over 17 min baseline, and over 20 min in tariquidar (data not shown).

Scans (439 μCi) were also obtained in 3 P-gp knockout (KO) and 3 wild-type (WT) mice for 90 min. The genetic absence of P-gp gave 2-3 fold higher PET measures of brain activity uptake and about 15-fold higher I total ex vivo brain activity (data not shown).

Similar to the experiments described in Example 7, ex vivo mice (2 KO, 2 WR) forebrain, cerebellum and plasma were analyzed with reverse phase radio-HPLC at 30 min after intraveneous injection of radiotracer (423 μCi). As described in Example 7, four radiometabolites were detected in mice plasma and brain tissues. The most lipophilic radiometabolite was identified by radio-HPLC co-elution as N-desmethyl-loperamide (dLop) (data not shown). Brain composition in WT mice was 26% parent (i.e., loperamide) and 4.3% dLop while in the KO mice 63% parent and 21% dLop was observed. Only parent and dLop concentrations increased 30- and 59-fold over control, respectively. Parent was selective to forebrain while dLop distributed evenly in cerebellum and forebrain. dLop was inhibited by P-gp more than loperamide (data not shown).

Thus, both loperamide and its radiometabolite dLop were found to be avid P-gp substrates. [$^{11}$C]dLop was found to be superior to [$^{11}$C]loperamide since it had fewer radiometabolites in brain and further, because it appeared to lack significant affinity for the opiate receptors.

Example 16

Inhibition of Metabolism of [$^{11}$C]Loperamide in Mouse by the Potent CYP3A4 Inhibitor, Ketoconazole The antidiarrheal drug, loperamide is an opiate receptor agonist that acts on the gastrointestinal tract. Loperamide has no central nervous system effect because it is excluded from brain by the efflux transporter, P-gp. [$^{11}$C]Loperamide ([$^{11}$C]Lop) has therefore been proposed as a PET radiotracer of brain P gp function (Passchier et al., 2003, *Mol Imaging Biol* 5:121). However, it was found that [$^{11}$C]loperamide is heavily metabolized to radiometabolites that are troublesome for quantitation of brain P-gp function (Zoghbi et al., 2008, *J Nucl Med* 49:649-656; Example 4). The primary route of metabolism for loperamide is via demethylation to N-desmethyl-loperamide (Kim et al., 2004, *Eur J Clin Pharmacol* 60:575-581). Cytochrome P450 isoforms, especially CYP3A4, play a crucial role in this metabolism. The following study describes the testing of whether the metabolism of [$^{11}$C]Lop in mice may be usefully inhibited by pretreatment with a potent CYP3A4 inhibitor, namely ketoconazole.

Ex vivo studies were performed in wild-type (WT) and P-gp knockout (KO) mice. During each of four study sessions, two mice (1 WT and 1 KO) were pretreated with ketoconazole (50 mg/kg, i.p.) and two mice (1 WT and 1 KO) were untreated. Mice were sacrificed at 30 min after injection of [$^{11}$C]Lop (519±31 µCi). Whole brain and plasma sample radioactivity were measured with γ-counting and HPLC analysis.

Figure 16:
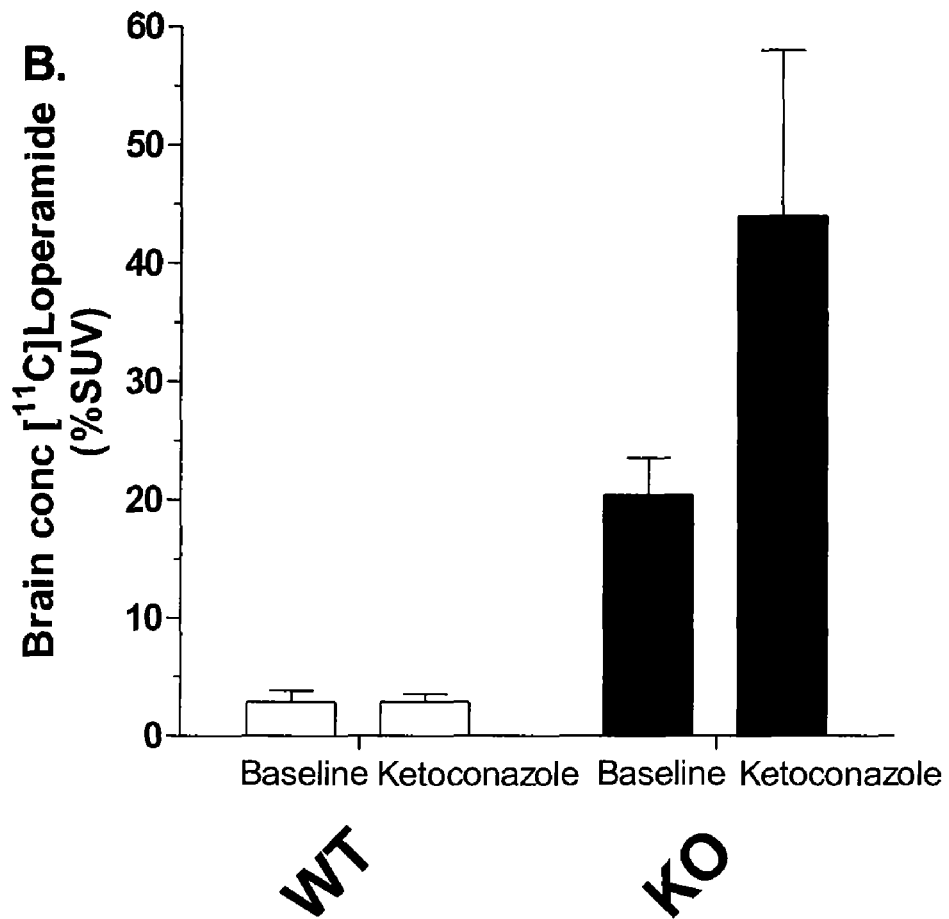
FIG. 16 depicts that pretreatment with ketoconazole increased brain uptake of [$^{11}$C]loperamide~two fold in P-gp KO mice, but had no effect in WT mice. Details are described in Example 17.

It was found that pretreatment of mice with ketoconazole increased the brain concentrations of [$^{11}$C]loperamide and [$^{11}$C]dLop about two-fold in KO mice, but had no effect in WT mice (FIG. 16). In addition, ketoconazole pretreatment significantly decreased the major and least lipophilic radiometabolite, dLop, in the brains of both WT and KO mice (by ~80 and 50%, respectively). In plasma of WT and KO mice, ketoconazole increased [$^{11}$C]loperamide and [$^{11}$C]dLop concentrations (by ~100 and 240%, respectively), but significantly decreased radiometabolite dLop (by ~70%).

Thus, ketoconazole pretreatment of mice resulted in higher levels of [$^{11}$C]loperamide in plasma, and in KO mice about two-fold increase of [$^{11}$C]loperamide in brain (FIG. 16). These increases were due to ketoconazole inhibition of CYP3A4, but not P-gp. Thus, for a radiotracer that is prone to N demethylation (such as [$^{11}$C]loperamide) pre-administration of a cytochrome P450 inhibitor (e.g., ketoconazole) may beneficially reduce such metabolism and improve radiotracer quantification.

Example 17

P-Glycoprotein Function Imaged with [$^{11}$C]N-desmethyl-Loperamide in Monkeys As described herein, [$^{11}$C]loperamide, an avid substrate for P-glycoprotein (P-gp), has been used to measure the function of this efflux transporter at the blood-brain barrier of monkey and rat. Unfortunately, [$^{11}$C]loperamide is rapidly metabolized to [$^{11}$C]dLop, which was determined to also be a substrate for P-gp. Since [$^{11}$C]dLop does not generate any further radiometabolites that are P-gp substrates, [$^{11}$C]dLop as a measure of P-gp function at the blood-brain barrier in monkeys was further evaluated. In anticipation of using [$^{11}$C]dLop in human subjects, whole body imaging in monkeys were performed to estimate radiation exposure.

For the brain study, six monkeys underwent 12 PET scans of the brain, with 5 at baseline and 7 after P-gp blockade using DCPQ (8 or 16 mg/kg i.v.) at 30 min prior to radiotracer injection. Four of the monkeys underwent PET imaging with P-gp blockade followed by displacement with either naloxone (5 mg/kg) or loperamide (1 mg/kg). Displacement agents were given at 30 min after the radiotracer. A subset of monkeys also had arterial blood sampling (n=5) and [$^{15}$O]H$_2$O PET scans (n=4) to measure the concentration of parent radiotracer in plasma and cerebral blood flow, respectively.

Figure 17:
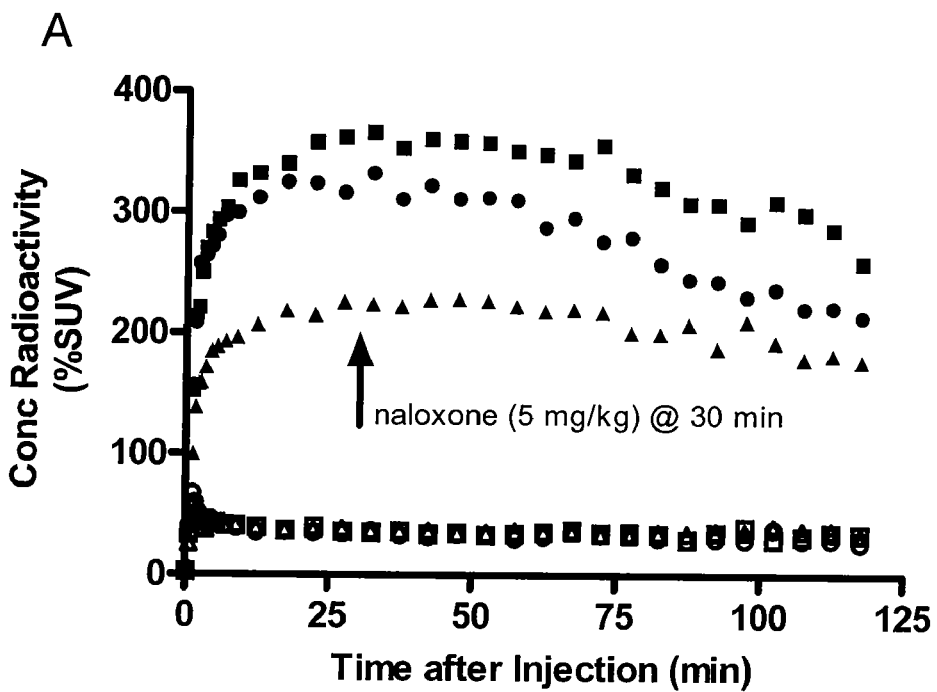
FIG. 17 depicts brain time activity curves of [$^{11}$C[dLop. (A) Brain time-activity curves of [$^{11}$C]dLop at baseline (open) and after P-gp blockade (filled) in frontal cortex (▲), putamen (■) and cerebellum (●) followed by naloxone displacement. (B) Correlation between relative cerebral blood flow (CBF) and mean brain radioactivity (25-50 min) after injection of [$^{11}$C]dLop. The symbols represent 8 regions from each of 4 monkeys. Relative CBF was measured as the concentration of radioactivity in each brain region for 1 min after injection of [$^{15}$O]H$_2$O. Details are described in Example 18.
Figure 17:
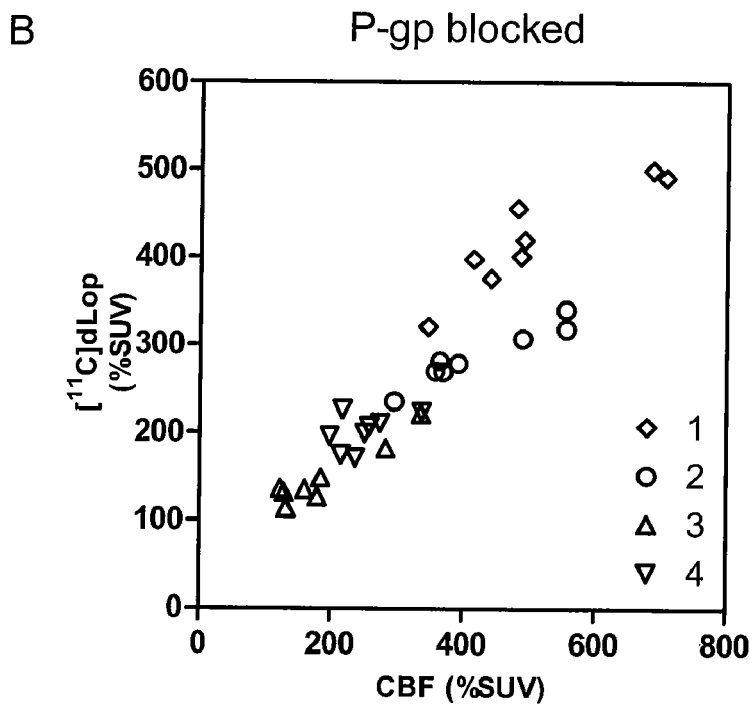

In the brain studies, it was observed that P-gp blockade increased brain uptake of [$^{11}$C]dLop 5- to 9-fold (FIG. 17A). Neither naloxone nor loperamide caused any apparent displacement of the radiotracer. Mean K, of the different brain regions was large (0.26 mL·cm$^{-3}$·min$^{-1}$), resulting in a high estimated single pass extraction (~50%). Because of the high single pass extraction, it was suspected that blood flow significantly affected [$^{11}$C]dLop uptake after P-gp blockade. Uptake of [$^{11}$C]dLop after P-gp blockade differed by brain region, and this differential uptake correlated linearly with regional cerebral blood flow (FIG. 17B). That is, after correcting for blood flow, the uptake of [$^{11}$C]dLop was similar in all brain regions.

For the whole body study, four monkeys were scanned dynamically with [$^{11}$C]dLop for 2 h, each at baseline and after P-gp blockade. In these whole body studies, it was observed that the organs with highest radiation exposure were thyroid (67 µSv/MBq), kidney (34 µSv/MBq) and liver (32 µSv/MBq). P-gp blockade had significant effects only in brain, for which radiation exposure increased from 3 to 5 µSv/MBq. The effective dose (µSv/MBq) was 9.4 and 8.9 at baseline and after P-gp blockade, respectively.

The above data confirmed that [$^{11}$C]dLop is a substrate for P-gp in monkey, since P-gp blockade in monkey increased brain uptake 5 to 9 fold. The rapid brain uptake after P-gp blockade was caused by a high single-pass extraction, which itself caused regional differences based on blood flow. Nevertheless, correction of [$^{11}$C]dLop brain uptake for regional blood flow showed that P-gp function was largely uniform through monkey brain. The radiation exposure of [$^{11}$C]dLop was similar to other $^{11}$C-labeled radiotracers. These results confirmed that [$^{11}$C]dLop will be a useful and safe radiotracer to measure P-gp function in human subjects.

Example 18

[$^{11}$C]N-Desmethyl-Loperamide Uptake in Human and Monkey Brain

Encouraged by the data obtained in monkeys, PET experiments in humans (similar to those described in Example 18) were pursued. [$^{11}$C]Loperamide was administered by injection to eight healthy human subjects.

Essentially administering [$^{11}$C]dLop to human subjects was performed as described in Example 18, except that the human subjects were not anesthetized and no inhibitors were administered. Further, a higher amount of radioactivity (typically between 5 and 15 mCi) was administered to account for the higher human body weight when compared to that of monkeys. The radioactivity amount of [$^{11}$C]dLop injected in any particular experiment is immaterial-the results will be the same, since [¹¹C]dLop is a radiotracer. Only enough radiotracer needs to be injected to provide enough radioactivity for external detection by whatever PET camera, imaging system, or other gamma-ray detection system is being used.

Figure 18:
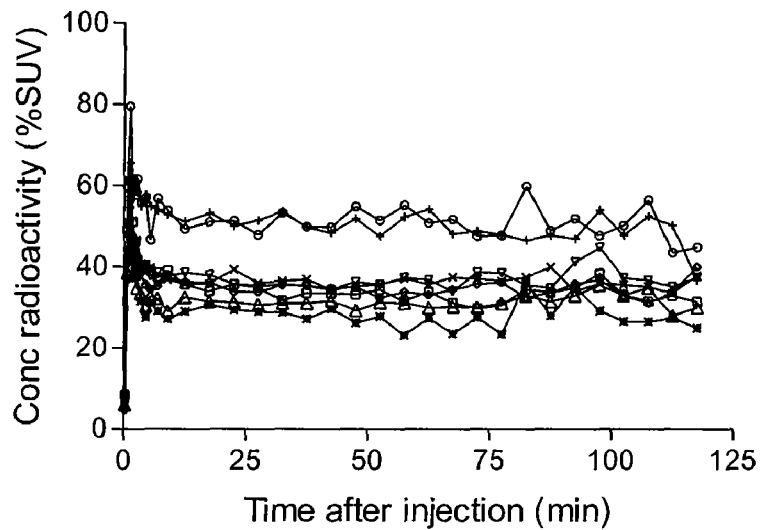
FIG. 18 depicts a comparison of [$^{11}$C]dLop uptake in monkey (A) and whole human brain (B). The distribution of radioactivity at various times after the administration of [$^{11}$C]dLop is shown. Key: (Panel A) frontal cortex (○), anterior cingulate (+), temporal cortex (▽), parietal cortex (◇), hippocampus (*), occipital cortex (□), putamen (△) and cerebellum (x). Details are described in Example 19.
Figure 18:
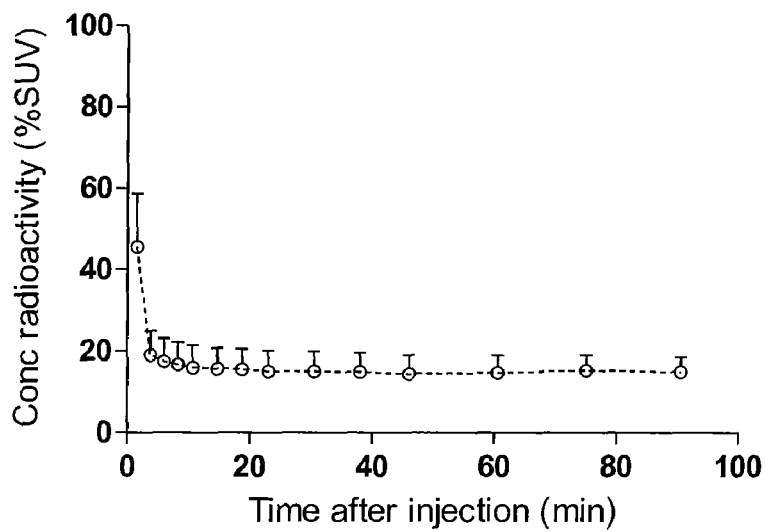

As described herein, PET imaging was used to determine the distribution of the radiotracer over time. A comparative study of [¹¹C]dLop uptake in human and monkey brain is shown in FIG. 18. As expected from the studies in vivo studies performed in mice and monkeys, uptake of the [¹¹C]dLop radiotracer into human brain is minimal because it is prevented by the action of P-gp at the blood-brain barrier (FIG. 18). The initial rapid brain uptake was followed by a rapid decrease to a stable level until the end of the scan (FIG. 18).

As a guidance, 100% SUV would be the concentration that one would expect in any organ if the radioactivity were completely distributed evenly throughout the body. A higher value in a particular organ would represent enrichment of radioactivity in that organ, and a lower value exclusion from that organ. Thus, for example in FIG. 19, the concentration of radioactivity in lungs, thyroid, kidney, spleen, liver, and eventually bladder can be seen.

The brain uptake was always well below 100% SUV, where SUV is standardized uptake value as defined herein. % SUV normalizes for radioactive dose and body weight and, thus, enables comparisons between species such as monkeys and human. The results obtained in the monkey studies and human studies, when expressed as % SUV in brain vs time were very similar. This indicated that the radiotracers appeared to be working in humans as it did in monkeys.

Example 19

Whole Body Imaging Using [¹¹C]dLop in Humans

In order to determine distribution of the radiotracer [¹¹C]dLop in the body of a human, [¹¹C]dLop was administered to eight healthy human subjects.

Figure 19:
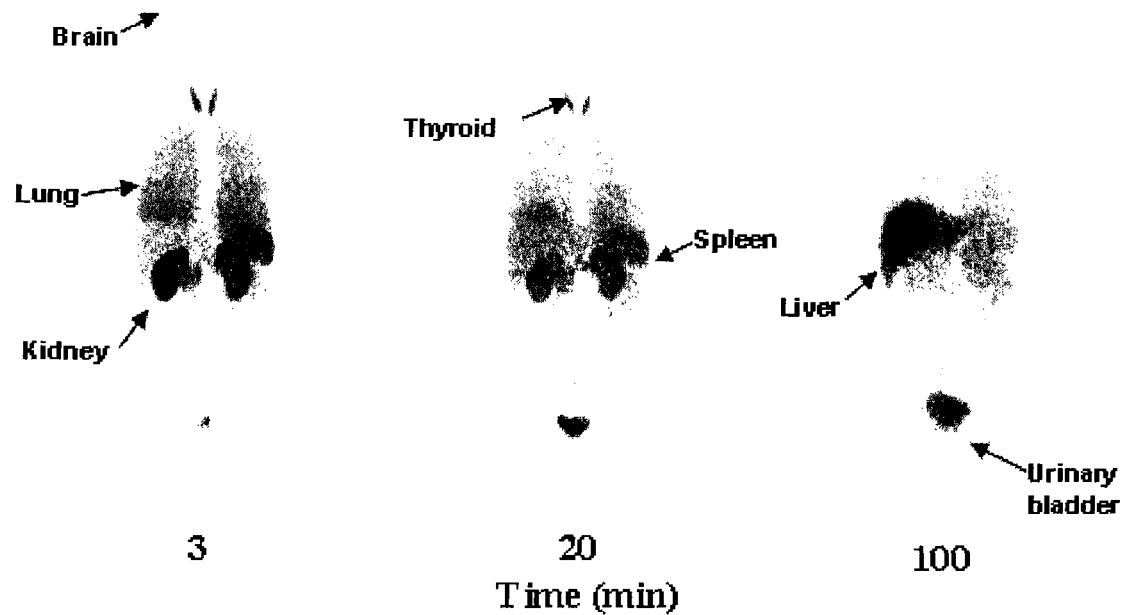
FIG. 19 depicts distribution of radioactivity in healthy male after administration of [$^{11}$C]dLop. Details are described in Example 20.

The distribution of radioactivity at various times after the administration (by injection) of [¹¹C]dLop to healthy male is shown in FIG. 19. Notably, the radioactivity is essentially excluded from the brain at all times, and is eventually excreted through urine.

Example 20

[¹¹C]dLop is an Improved Radiotracer for Measuring Brain P-gp Function

[¹¹C]Loperamide ([¹¹C]Lop) has been proposed as a PET radiotracer for assessing permeability-glycoprotein (P-gp) efflux pump function in vivo (Passchier et al., 2003, *Mol Imaging Biol* 5:121). As shown herein [¹¹C]Lop is heavily metabolized. At 30 min after the injection of [¹¹C]Lop into knockout (KO; mdr-1a/b(−/−)) mice, only 50% of the brain radioactivity is unchanged [¹¹C]Lop, while 30% of the brain radioactivity is [¹¹C]N-desmethyl-loperamide ([¹¹C]dLop) (Zoghbi et al., 2008, *J Nucl Med* 49:649-656; Example 4). These radiometabolites would confound any attempt to use biomathematical modeling to measure brain P-gp function with [¹¹C]Lop. It was shown herein that [¹¹C]dLop poorly penetrates the blood-brain barrier in wild type (WT) mice, and hence that [¹¹C]dLop itself is a substrate for P-gp (see also, Zoghbi et al., 2008, *J Nucl Med* 49:649-656). It was appreciated that [¹¹C]dLop is superior to [¹¹C]Lop as a radiotracer of P-gp function, since [¹¹C]dLop metabolism is also expected to be primarily by demethylation, but leads only to polar non-troublesome radiometabolites (Examples 4 and 8; Zoghbi et al., 2008, *J Nucl Med* 49:649-656). Consequently, we prepared [¹¹C]dLop and tested its behavior as a PET radiotracer.

[¹¹C]dLop was prepared as described herein by methylation of a synthesized primary amide precursor with [¹¹C] iodomethane.

The brains of three P-gp KO and three WT mice were scanned for 90 min after administration of [¹¹C]dLop (~580 μCi, i.v.). Mice injected with [¹¹C]dLop (600 μCi, i.v.) were also sacrificed at 30 min, and acetonitrile extracts of blood and brain analyzed with reverse phase HPLC. The brains of rhesus monkeys were scanned with [¹¹C]dLop (~10 mCi) at baseline and at 20 min after treatment with a dose of the P-gp inhibitor, DCPQ (4, 8, or 16 mg/kg i.v.)

[¹¹C]dLop was readily prepared in high activities. After administration of [¹¹C]dLop, PET showed 3-4-fold higher brain radioactivity uptake in KO than in WT mice. Ex vivo analysis showed that 90% of the brain radioactivity in KO mice was unchanged [¹¹C]dLop and at a 16-fold higher level than in WT mice. Only less lipophilic radiometabolites were detected in mice plasma and brain tissues. After administration of [¹¹C]dLop to monkey, PET showed a low level of brain radioactivity under baseline conditions, but this level dose-dependently increased in monkeys pre-treated with DCPQ (by more than 7-fold at 16 mg/kg)

This experiment confirmed that [¹¹C]dLop is an avid substrate forbrain P-gp in mouse and monkey. Radioactivity entering KO mouse brain is predominantly unchanged [¹¹C]dLop, indicating the potential of this radiotracer for measuring brain P-gp function and it superiority over [¹¹C]Lop for this purpose.

What is claimed is:

1. A compound according to formula:

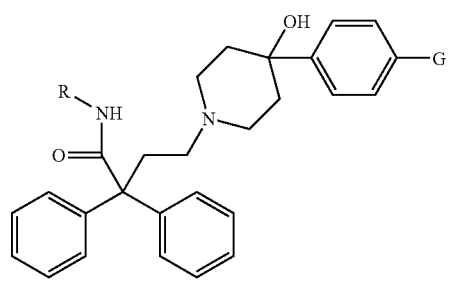

wherein:
R is ¹¹CH₃;
G is chlorine
and all stereoisomers or pharmaceutically acceptable salts thereof, in isolated and purified form.

2. A pharmaceutical composition comprising:
(i) the compound of claim 1; and
(ii) a pharmaceutically acceptable carrier or excipient.

* * * * *